US007148325B2

(12) United States Patent
Sakalian et al.

(10) Patent No.: US 7,148,325 B2
(45) Date of Patent: Dec. 12, 2006

(54) CHIMERIC RETROVIRAL GAG GENES AND SCREENING ASSAYS

(75) Inventors: Michael Sakalian, Oklahoma City, OK (US); Eric Hunter, Vestavia Hills, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/968,355

(22) Filed: Sep. 28, 2001

(65) Prior Publication Data

US 2002/0094523 A1 Jul. 18, 2002

Related U.S. Application Data

(60) Provisional application No. 60/236,273, filed on Sep. 28, 2000.

(51) Int. Cl.
*C07K 2/00* (2006.01)
*C07K 17/00* (2006.01)
*C07K 14/00* (2006.01)
*C07K 14/155* (2006.01)

(52) U.S. Cl. ............... 530/350; 530/300; 435/5; 435/69.1; 424/204.1; 424/207.1; 424/208.1

(58) Field of Classification Search ............... 530/300, 530/350; 424/204.1, 207.1, 208.1; 435/5, 435/69.1
See application file for complete search history.

(56) References Cited

U.S. PATENT DOCUMENTS 4,816,567 A 3/1989 Cabilly
4,918,166 A * 4/1990 Kingsman et al. .......... 530/350

FOREIGN PATENT DOCUMENTS

EP 0 803 574 A2 10/1997

OTHER PUBLICATIONS

Sakalian J Virology 1996, vol. 70, pp. 3706-3715.*
Sakalian and Hunter 1999 J of Virology vol. 73, pp. 8073-8082.*
Ausubel, F.M. et al., *Current protocols in Molecular Biology*, 1989, John Wiley and Sons, New York City. (Book).
Bennett, R. P., Nelle, T. D., and Wills, J. W., "Functional chimeras of the Rous sarcoma virus and human immunodeficiency virus gag proteins," *Journal of Virology*, 1993, p. 6487-6498, vol. 67, No. 11.
Berkowitz, R., Fisher, J., and Goff, S. P., "RNA packaging," *Current Topics in Microbiology and Immunology*, 1996, p. 177-218, vol. 214.
Berkowitz, R. D., Luban, J., and Goff, S. P., "Specific binding of human immunodeficiency virus type 1 *gag* polyprotein and nucleocapsid protein to viral RNAs detected by RNA mobility shift assays," *Journal of Virology*, 1993, p. 7190-7200, vol. 67 No. 12.
Blake, J., Johnston, J. V., Hellström, K. E., Marquardt, H., and Chen, L., "Use of combinatorial peptide libraries to construct functional mimics of tumor epitopes recognized by MHC class I-restricted cytolytic T lymphocytes," *J. Exp. Med.*, 1996, p. 121-130, vol. 184.
Bolognesi, D. P., Luftig, R., and Shaper, J. H., "Localization of RNA tumor virus polypeptides. I. Isolation of further virus substructures," *Virology*, 1973, p. 549-564, vol. 56.
Böttcher, B., Wynne, S. A., and Crowther, R. A. "Determination of the fold of the core protein of hepatitis B virus by electron cryomicroscopy," *Nature*, 1997, p. 88-91, vol. 386.
Bryant, M., and Ratner, L., "Myristoylation-dependent replication and assembly of human immunodeficiency virus 1," *Proc. Natl. Acad. Sci. USA* 1990, p. 523-527, vol. 87.
Campbell, S., and Vogt, V. M., "Self-assembly *in vitro* of purified CA-NC proteins from Rous sarcoma virus and human immunodeficiency virus type 1," *Journal of Virology*, 1995, p. 6487-6497, vol. 69, No. 10.
Campbell, S., and Vogt, V. M., "*In vitro* assembly for virus-like particles with Rous sarcoma virus gag deletion mutants: Identification of the p10 domain as a morphological determinant in the formation of spherical particles," *Journal of Virology*, 1997, p. 4425-4435, vol. 71, No. 6.
Chien, C. T., Bartel, P. L., Sternglanz, R., and Fields, S., "The two-hybrid system: A method to identify and clone genes for proteins that interact with a protein of interest," *Proc. Natl. Acad. Sci. USA*, 1991, p. 9578-9582, vol. 88.
Clackson, T., Hoogenboom, H. R., Griffiths, A. D., and Winter, G., "Making antibody fragments using phage display libraries," *Nature*, 1991, p. 624-628, vol. 352.
Coffin, J. M., Hughes, S. H., and Varmus, H. E., eds., *Retroviruses*, 1997, Cold Spring Harbor Laboratory Press, Cold Spring Harbor, NY. (Book).
Conte, M. R., Klikova, M., Hunter, E., Ruml, T., and Matthews, S., "The three-dimensional solution structure of the matrix protein from the type D retrovirus, the Mason-Pfizer Monkey virus, and implications for the morphology of retroviral assembly," *Embo J.*, 1997, p. 5819-5826, vol. 16, No. 19.
Conway, J. F., Cheng, N., Zlotnick, A., Wingfield, P. T., Stahl, S. J., and Steven, A. C., "Visualization of a 4-helix bundle in the hepatitis B virus capsid by cryo-electron microscopy," *Nature*, 1997, p. 91-94, vol. 386.
Craven, R. C., and Parent, L. J., "Dynamic interactions of the Gag polyprotein," *Current Topics in Microbiology and Immunology*, 1996, p. 65-94, vol. 214.
Delchambre, M., Gheysen, D., Thines, D., Thiriart C., Jacobs, E., Verdin, E., Horth, M., Burny, A., and Bex, F., "The Gag precursor of simian immunodeficiency virus assembles into virus-like particles," *EMBO J.*, 1989, p. 2653-2660, vol. 8, No. 9.

(Continued)

*Primary Examiner*—Bruce R. Campell
*Assistant Examiner*—Myron G. Hill
(74) *Attorney, Agent, or Firm*—Saliwanchik, Lloyd & Saliwanchik

(57) ABSTRACT

The subject invention provides novel and advantageous methods for identifying amino acid sequences in random peptide libraries that can bind to Gag polypeptides. The subject invention also establishes a novel in vitro system that can be used to test competitive inhibitors of retrovrial capsid assembly. Also provided are peptides, and compositions containing these peptides, which are inhibitors of the retrovirus Gag protein(s) function. Chimeric Gag polypeptides are also provided.

27 Claims, 11 Drawing Sheets

OTHER PUBLICATIONS

Dickson, C., Eisenman, R., Fan, H., Hunter, E., and Teich, N., "Protein biosynthesis and assembly," *RNA tumor viruses*, R. Weiss, N. Teich, H. Varmus, and J. Coffin, eds., 1984, p. 513-648, vol. 1, Cold Spring Harbor Laboratory, Cold Spring Harbor, NY.

Eisenman, R., Vogt, V. M., and Diggelmann, H., "Synthesis of avian RNA tumor virus structural proteins," *Cold Spring Harbor Symp. Quant. Biol.*, 1974, p. 1067-1075, vol. 39.

Fields, S., and Song, O., "A novel genetic system to detect protein-protein interactions," *Nature*, 1989, p. 245-246, vol. 340.

Fields, S., and Sternglanz, R., "The two-hybrid system: an assay for protein-protein interactions," *Trends Genet.*, 1994, p. 286-292, vol. 10, No. 8.

Garnier, L., Wills, J. W., Verderame, M. F., and Sudol, M., "WW domains and retrovirus budding," *Nature*, 1996, p. 744-745, vol. 381.

Gebhardt, A., Bosch, J. V., Ziemiecki, A., and Friis, R. R., "Rous sarcoma virus p19 and gp35 can be chemically crosslinked to high molecular weight complexes: An insight into virus assembly," *J. Mol. Biol.*, 1984, p. 297-317, vol. 174.

Gelderblom, H., "Morphogenesis, maturation, and fine structure of lentiviruses," *Retroviral Proteases: Control of Maturation and Morphogenesis*, L. H. Pearl, ed., 1990, p. 159-180, Stockton Press, New York, NY. (Book).

Gelderblom, H. R., "Assembly and morphology of HIV: potential effect of structure on viral function," *AIDS*, 1991, p. 617-638, vol. 5.

Gelderblom, H. R., Hausmann, E. H. S., Özel, M., Pauli, G., and Koch, M. A., "Fine structure of human immunodeficiency virus (HIV) and immunolocalization of structural proteins," *Virology*, 1987, p. 171-176. vol. 156.

Gheysen, D., Jacobs, E., De Foresta, F., Thiriart, C., Francotte, M., Thines, D., and De Wilde, M., "Assembly and release of HIV-1 precursor Pr55gag virus-like particles from recombinant baculovirus-infected insect cells," *Cell*, 1989, p. 103-112. vol. 59.

Gitti, R. K., Lee, B. M., Walker, J., Summers, M. F., Yoo, S., and Sundquist, W. I., "Structure of the amino-terminal core domain of the HIV-1 capsid protein," *Science*, 1996, p. 231-235, vol. 273.

Goding, J.W., *Monoclonal Antibodies: Principles and Practice*, 1983, Academic Press, New York. (Book).

Gonzalez, S. A., Affranchino, J. L., Gelderblom, H. R., and Burny, A., "Assembly of the matrix protein of simian immunodeficiency virus into virus-like particles," *Virology*, 1993, p. 548-556, vol. 194.

Gorelick, R. J., Nigida, S. M., Bess, J. W., Arthur, L. O., Henderson, L. E., and Rein, A., "Non-infectious human immunodeficiency virus type 1 mutants deficient in genomic RNA," *Journal of Virology*, 1990, p. 3207-3211, vol. 64, No. 7.

Gorelick, R. J., Henderson, L. E., Hanser, J. P., and Rein, A., "Point mutants of Moloney murine leukemia virus that fail to package viral RNA: Evidence for specific RNA recognition by a "zinc-finger-like" protein sequence," *Proc. Natl. Acad. Sci. USA*, 1988, p. 8420-8424, vol. 85.

Göttlinger, H. G., Dorfman, T., Sodroski; J. G., and Haseltine, W. A., "Effect of mutations affecting the p6 *gag* protein on human immunodeficiency virus particle release," *Proc. Natl. Acad. Sci. USA*, 1991, p. 3195-3199, vol. 88.

Göttlinger, H. G., Sodroski, J. G., and Haseltine, W. A., "Role of capsid precursor processing and myristoylation in morphogenesis and infectivity of human immunodeficiency virus type 1," *Proc. Natl. Acad. Sci. USA*, 1989, p. 5781-5785, vol. 86.

Haffar, O., Garrigues, J., Travis, B., Moran, P., Zarling, J., and Hu, S. -L., "Human immunodeficiency virus-like, non-replication, Gag-Env particles assemble in a recombinant vaccinia virus expression system," *Journal of Virology*, 1990, p. 2653-2659, vol. 64, No. 6.

Hill, C. P., Worthylake, D., Bancroft, D. P., Christensen, A. M., and Sundquist, W. I., "Crystal structures of the trimeric human immunodeficiency virus type 1 matrix protein: implications for membrane association and assembly," *Proc. Natl. Acad. Sci. USA*, 1996, p. 3099-3104, vol. 93.

Houghten, R. A., "The broad utility of soluble peptide libraries for drug discovery," *Gene*, 1993, p. 7-11, vol. 137.

Houghten, R. A., "Combinatorial libraries. Finding the needle in the haystack," *Curr. Biol.*, 1994, p. 564-567, vol. 4.

Houghten, R. A. Pinilla, C., Blondelle, S. E., Appel, J. R., Dooley, C. T., and Cuervo, J. H., "Generation and use of synthetic peptide combinatorial libraries for basic research and drug discovery," *Nature*, 1991, p. 84-86, vol. 354.

Hudson, L., Hay, F. C., *Practical Immunology*, 1980, Blackwell Scientific, Boston. (Book).

Hunter, E., "Macromolecular interactions in the assembly of HIV and other retroviruses," *Sem in Virology*, 1994, p. 71-83, vol. 5.

Hunter, E., Casey, J., Hahn, B., Hayami, M., Korber, B., Kurth, R., Neil, J., Rethwilm, A., Sonigo, P., and Stoye, J., "Retroviridae," *Virus Taxonomy. Seventh Report of the International Committee on Taxonomy of Viruses*, van Regenmortel, M. H. V., et al., eds., 1999, p. 369-387, Academic Press, San Diego.

Hurrell, J. G. R., *Monoclonal Hybridoma Antibodies: Techniques and Applications*, 1982, CRC Press, Boca Raton, FL. (Book).

Jones, T. A., Blaug, G., Hansen, M., and Barklis, E., "Assembly of gag-β-galactosidase proteins into retrovirus particles," *Journal of Virology*, 1990, p. 2265-2279, vol. 64, No. 5.

Jowett, J. B. M., Hockley, D. J., Nermut, M. V., and Jones, I. M., "Distict signals in human immunodeficiency virus type 1 Pr55 necessary for RNA binding and particle formation," *Journal of General Virology*, 1992, p. 3079-3086, vol. 73.

Katz, R. A., and Jentoft, J. E., "What is the role of the *cys-his* motif in retroviral nucleocapsid (NC) proteins?" *BioEssays*, 1989, p. 176-181, vol. 11, No. 6.

Klikova, M., Rhee, S. S., Hunter, E., and Ruml, T., "Efficient *in vivo* and *in vitro* assembly of retroviral capsids from Gag precursor proteins expressed in bacteria," *Journal of Virology*, 1995, p. 1093-1098, vol. 69, No. 2.

Köhler, G., and Milstein C., "Continuous cultures of fused cells secreting antibody of predefined specificity," *Nature*, 1975, p. 495-497, vol. 256.

Kräusslich, H. -G., and Welker, R., "Intracellular transport of retroviral capsid components," *Current Topics in Microbiology and Immunology*, 1996, p. 25-64, vol. 214.

Lam, K.S., Salmon, S. E., Hersh, E. M., Hruby, V. J., Kazmierski, W. M., and Knapp, R. J., "A new type of synthetic peptide library for identifying ligand-binding activity," *Nature*, 1991, p. 82-84, vol. 354, [published errata appeared in *Nature* 1992, p. 434, vol. 358 and 1992, p. 768, vol. 360].

Lebl, M., KrchňáK, V., Sepetov, N. F., Seligmann, B., Štrop, P., Felder, S., and Lam, K. S., "One-bead-one-structure combinatorial libraries," *Biopolymers*, 1995, p. 177-198, vol. 37.

Lebl, M., Pátek, M., Kočiš, P., Krchňák, V., Hruby, V. J., Salmon, S. E., and Lam, K. S., "Multiple release of equimolar amounts of peptides from a polymeric carrier using orthogonal linkage-cleavage chemistry," *In.t J. Peptide Protein Res.*, 1993, p. 201-203, vol. 41.

Lefkovits, I., and Pernis, B., eds., *Immunological Methods*, 1981, vol. II, Academic Press, New York. (Book).

Leis, J., Baltimore, D., Bishop, J. M., Coffin, J., Fleissner, E., Goff, S. P., Oroszlan, S., Robinson, H., Skalka, A. M., Temin, H. M., and Vogt, V., "Standardized and simplified nomenclature for proteins common to all retroviruses," *Journal of Virology*, 1988, p. 1808-1809, vol. 62, No. 5.

Linial, M. L., and Miller, A. D., "Retroviral RNA packaging: Sequence requirements and implications," *Curr. Top. Microbiol. And Immunol.*, 1990, p. 125-152, vol. 157.

Madisen, L., Travis, B., Hu, S. -L., and Purchio, A. F., "Expression of the human immunodeficiency virus *gag* gene in insect cells," *Virology*, 1987, p. 248-250, vol. 158.

Marks, J. D., Hoogenboom, H. R., Bonnert, T. P., McCafferty, J., Griffiths, A. D., and Winter, G., "By-passing immunization: Human antibodies from V-gene libraries displayed on phage," *J. Mol. Biol.*, 1991, p. 581-597, vol. 222.

Martin, E. W., *Remington's Pharmaceutical Science*, 1990, Mack Publishing Co., Easton, PA. (Book).

Matthews, S., Barlow, P., Boyd, J., Barton, G., Russell, R., Mills, H., Cunningham, M., Meyers, N., Burns, N., Clark, N., Kingsman, S., Kingsman, A., and Campbell, I., "Structural similarity between the p17 matrix protein of HIV-1 and interferon-γ," *Nature*, 1994, p. 666-668, vol. 370.

Matthews, S., Mikhailov, M., Burny, A., and Roy, P., "The solution structure of the bovine leukaemia virus matrix protein and similarity with lentiviral matrix proteins," *Embo J.*, 1996, p. 3267-3274, vol. 15, No. 13.

Méric, C., and Goff, S. P., "Characterization of Moloney murine leukemia virus mutants with single amino acid substitutions in the cys-his box of the nucleocapsid protein," *Journal of Virology*, 1989, p. 1558-1568, vol. 63, No. 4.

Méric, C., Gouilloud, E., and Spahr, P. -F., "Mutations in Rous sarcoma virus nucleocapsid protein p12 (NC): deletions of Cys-His boxes," *Journal of Virology*, 1988, p. 3328-3333, vol. 62, No. 9.

Mishell, B. B., and Shiigi, S. M., eds., *Selected Methods in Cellular Immunology*, 1980, W. H. Freeman, San Fransisco. (Book).

Momany, C., Kovari, L. C., Prongay, A. J., Keller, W., Gitti, R. K., Lee, B. M., Gorbalenya, A. E., Tong, L., McClure, J., Ehrlich, L. S., Summers, M. F., Carter, C., and Rossmann, M. G., "Crystal structure of dimeric HIV-1 capsid protein," *Nat Struct Biol*, 1996, p. 763-770, vol. 3.

Morrison, S. L., Johnson, M. J., Herzenberg, L. A., and Ol, V. T., "Chimeric human antibody molecules: Mouse antigen-binding domains with human constant region domains," *Proc. Natl. Acad. Sci. USA*, 1984.

Nermut, M. V., and Hockley, D. J., "Comparative morphology and structural classification of retroviruses," *Current Topics in Microbiology and Immunology*, 1996, p. 1-24, vol. 214.

Nermut, M. V., Hockley, D. J., Jowett, J. B. M., Jones, I. M., Garreau, M., and Thomas, D., "Fullerene-like organization of HIV gag-protein shell in virus-like particles produced by recombinant baculovirus," *Virology*, 1994, p. 288-296, vol. 198.

Niedrig, M., Gelderblom, H. R., Pauli, G., März, J., Bickhard, H., Wolf, H., and Modrow, S., "Inhibition of infectious human immunodeficiency virus type 1 particle formation by Gag protein-derived peptides," *Journal of General Virology*, 1994, p. 1469-1474, vol. 75.

Nikolaiev, V., Stierandová, A., Krchňák, V., Seligmann, B., Lam, K. S., Salmon, S. E., and Lebl, M., "Peptide-encoding for structure determination of nonsequenceable polymers within libraries synthesized and tested on solid-phase supports," *Peptide Research*, 1993, p. 161-170, vol. 6, No. 3.

Parent, L., Bennett, R., Craven, R., Nelle, T., Krishna, N., Bowzard, J., Wilson, C., Puffer, B., Montelaro, R., and Wills, J., "Positionally independent and exchangeable late budding functions of the Rous sarcoma virus and human immunodeficiency virus Gag proteins," *J. Virol.*, 1995, p. 5455-5460, vol. 69, No. 9.

Pepinsky, R. B., Cappiello, D., Wilkowski, C., and Vogt, V. M., "Chemical cross-linking of proteins in avian sarcoma and leukemia viruses," *Virology*, 1980, p. 205-210, vol. 102.

Pepinsky, R. B., and Vogt, V. M., "Identification of retrovirus matrix proteins by lipid-protein crosslinking," *J. Mol. Biol.*, 1979, p. 819-837, vol. 131.

Pluckthun in *The Pharmacology of Monoclonal Antibodies*, Rosenburg and Moore, eds., 1994, p. 269-315, vol. 113, Springer-Verlag, New York. (Book).

Rao, Z., Belyaev, A. S., Fry, E., Roy, P., Jones, I. M., and Stuart, D. I., "Crystal structure of SIV matrix antigen and implications for virus assembly," *Nature*, 1995, p. 743-747, vol. 378.

Rhee, S. S., and Hunter, E., "Myristylation is required for intracellular transport but not for assembly of D-type retrovirus capsids," *Journal of Virology*, 1987, p. 1045-1053, vol. 61, No. 4.

Rhee, S. S., and Hunter, E., "A single amino acid substitution within the matrix protein of a type D retrovirus converts its morphogenesis to that of a type C retrovirus," *Cell*, p. 77-86, vol. 63.

Rhee, S. S., and Hunter, E., "Amino acid substitutions within the matrix protein of type D retroviruses affect assembly, transport and membrane association of a capsid," *EMBO J*, 1991, p. 535-546, vol. 10, No. 3.

Sakalian, M., and Hunter, E., "Separate assembly and transport domains within the gag precursor of Mason-Pfizer monkey virus," *Journal of Virology*, 1999, p. 8073-8082, vol. 73, No. 10.

Sakalian, M., Parker, S. D., Weldon, R. A., Hunter, E., "Synthesis and assembly for retrovirus gag precursors into immature capsids *in vitro*," *Journal of Virology*, 1996, p. 3706-3715, vol. 70, No. 6.

Sakalian, M. Wills, J. W., and Vogt, V. M., "Efficiency and selectivity of RNA packaging by *Rous sarcoma* virus gag deletion mutants," *Journal of Virology*, 1994, p. 5969-5981, vol. 68, No. 9.

Salmon, S. E., Lam, K. S., Felder, S., Yeoman, H., Schlessinger, J., Ullrich, A., Krchňak, V., and Lebl, M., "One bead, one chemical compound: use of the selectide process for anticancer drug discovery," *Acta Oncologica*, 1994, p. 127-131, vol. 33, No. 2.

Salmon, S., Lam, K., Lebl, M., Kandola, A., Khattri, P., Wade, S., Patek, M., Kocis, P., Krchňak, V., Thorpe, D., and Felder, S., "Discovery of biologically active peptides in random libraries: solution-phase testing after staged orthogonal release from resin beds," *Proc. Natl. Acad. Sci. USA*, 1993, p. 11708-12, vol. 90.

Sambrook, J, et al., *Molecular Cloning: A Laboratory Manual*, 1989, Cold Spring Harbor Laboratory, Cold Spring Harbor, NY. (Book).

Schiestl, R. H., and Gietz, R. D., "High efficiency transformation of intact yeast cells using single stranded nucleic acids as a carrier," *Curr Genet*, 1989, p. 339-346, vol. 16.

Scott, J. K., and Craig, L., "Random peptide libraries," *Curr Opin Biotechnol*, 1994, p. 40-48, vol. 5.

Smith, A. J., Cho, M. -I., Hammerskjöld, M. -L., and Rekosh, D., "Human immunodeficiency virus type 1 Pr55gag and Pr160gag-pol expressed from a simian virus 40 late-replacement vector are efficiently processed and assembled into virus-like particles," *Journal of Virology*, 1990, p. 2743-2750, vol. 64, No. 6.

Smith, G. P., and Scott, J. K., "Libraries of peptides and proteins displayed on filamentous phage," *Methods Enzymol*, 1993, p. 228-257, vol. 217.

Sommerfelt, M. A., Rhee, S. S., and Hunter, E., "Importance of p12 protein in Mason-Pfizer monkey virus assembly and infectivity," *Journal of Virology*, 1992, p. 7005-7011, vol. 66, No. 12.

Spearman, P., Wang, J. J., Heyden N. V., and Ratner, L., "Identification of human immunodeficiency virus type 1 Gag protein domains essential to membrane binding and particle assembly," *Journal of Virology*, 1994, p. 3232-3242, vol. 68, No. 5.

Strambio-De-Castillia, C., and Hunter, E., "Mutational analysis of the major homology region of Mason-Pfizer monkeys virus by use of saturation mutagenesis," *Journal of Virology*, 1992, p. 7021-7032, vol. 66, No. 12.

Stromberg, K., Hurley, N. E., Davis, N. L., Rueckert, R. R., and Fleissner, E., "Structural studies of avian myeloblastosis virus: Comparison of polypeptides in virion and core component by dodecyl sulfate-polyacrylamide gel electrophoresis," *Journal of Virology*, 1974, p. 513-528, vol. 13, No. 2.

Teich, N., "Taxonomy of retroviruses," *RNA tumor viruses*, 2$^{nd}$ ed., A. Weiss, N. Teich, H. E. Varmus, and J. M. Coffin, eds., 1982, p. 25-207, Cold Spring Harbor Laboratory, NY. (Book).

Van Criekinge, W., and Beyaert, R., "Yeast two-hybrid: State of the art," *Biological Procedures Online*, 1999, p. 1-38, vol. 2, No. 1.

Veronese, F. M. and Morpurgo, M., "Bioconjugation in pharmaceutical chemistry," *Farmaco*, 1999, p. 497-516, vol. 54, No. 8.

Vidal, M., Brachmann, R. K., Fattaey, A., Harlow, E., and Boeke, J. D., "Reverse two-hybrid and one-hybrid systems to detect dissociation of protein-protein and DNA-protein interactions," *Proc. Natl. Acad. Sci. USA*, 1996, p. 10315-10320, vol. 93.

Vidal, M., Braun, P., Chen, E., Boeke, J. D., and Harlow, E., "Genetic characterization of a mammalian protein-protein interaction domain by using a yeast reverse two-hybrid system," *Proc. Natl. Acad. Sci. USA*, 1996, p. 10321-10326, vol. 93.

Weber, I. T., "Comparison of the crystal structures and intersubunit interactions of human immunodeficiency and *Rous sarcoma* virus proteases," *J. Biol. Chem.* 1990, p. 10492-10496, vol. 265, No. 18.

Weldon, R. A., and Wills, J. W., "Characterization of a small (25 kDa) derivative of the *Rous sarcoma* virus Gag protein competent for particle release," *Journal of Virology*, 1993, p. 5550-5561, vol. 67, No. 9.

White, M. A., "The yeast two-hybrid system: Forward and reverse," *Proc. Natl. Acad. Sci. USA*, 1996, p. 10001-10003, vol. 93.

Wild, C., Oas, T., McDanal, C., Bolognesi, D., and Mathews, T., "A synthetic peptide inhibitor of human immunodeficiency virus replication: Correlation between solution structure and viral inhibition," *Proc. Natl. Acad. Sci. USA*, 1992, p. 10537-10541, vol. 89.

Wills, J. W., Cameron, C. E., Wilson, C. B., Xiang, Y., Bennett, R. P., and Leis, J., "An assembly domain of the *Rous sarcoma* virus Gag protein required late in budding," *Journal of Virology*, 1994, p. 6605-6618, vol. 68, No. 10.

Wills, J. W., and Craven, R. C., "Form, function, and use of retroviral Gag proteins," *AIDS*, 1991, p. 639-654, vol. 5.

Wills, J. W., Craven, R. C., and Achacoso, J. A., "Creation and expression of myristylated forms of *Rous sarcoma* virus Gag protein in mammalian cells," *Journal of Virology*, 1989, p. 4331-4343, vol. 63, No. 10.

Yang, M., Wu, Z., and Fields, S., "Protein-peptide interactions analyzed with the yeast two-hybrid system," *Nucleic Acids Research*, 1995, p. 1152-1156, vol. 23, No. 7.

Yasuda, J., and Hunter E., "A proline-rich motif (PPPY) in the Gag polyprotein of Mason-Pfizer monkey virus plays a maturation-independent role in virion release," *Journal of Virology*, 1998, p. 4095-4103, vol. 72, No. 5.

Yu, X., Yuan, X., Matsuda, Z., Lee, T. H., and Essex, M., "The matrix protein of human immunodeficiency virus type 1 is required for incorporation of viral envelope protein into mature virions," *Journal of Virology*, 1992, p. 4966-4971, vol. 66, No. 8.

Yuan, X., Yu, X., Lee, T. H., and Essex, M., "Mutations in the N-terminal region of human immunodeficiency virus type 1 matrix protein block intracellular transport of the Gag precursor," *Journal of Virology*, 1993, p. 6387-6394, vol. 67, No. 11.

Zhou, W., Parent, L. J., Wills, J. W., and Resh, M. D., "Identification of a membrane-binding domain within the amino-terminal region of human immunodeficiency virus type 1 Gag protein which interacts with acidic phospholipids," *Journal of Virology*, 1994, p. 2556-2569, vol. 68, No. 4.

Sakalian, M. et al. "Delineation of separate assembly and transport functions within the Gag precursor of M-PMV" presented at the American Society for Virology 16th Annual Meeting at Bozeman, Montana; Jul. 19-23, 1997, abstract.

Sakalian, M. et al. "Separate assembly and transport domains with the Gag precursor of Mason-Pfizer monkey virus" presented at the 1999 Meeting on Retroviruses, Cold Spring Harbor, New York; May 25-30, 1999, abstract.

Sakalian, M. et al. "A system for the study of retrovirus assembly and its inhibition in vitro" presented at the International Conference on the Discovery and Clinical Development of Antiretroviral Therapies, St. Thomas, West Indies, US Virgin Islands; Dec. 13-17, 1998, abstract.

Sakalian, M. et al. "The Mason-Pfizer monkey virus internal scaffold domain enables in vitro assembly of human immunodeficiency virus type 1 Gag" *J. Virology*, 2002, 76(21):10811-10820.

Lanman, J. et al. "Kinetic analysis of the role of Intersubunit interactions in human immunodeficiency virus type 1 capsid protein assembly in vitro" *J. Virology*, 2002, 76(14):6900-6908.

Knejzlik, Z. et al. "Isolation and characterization of the Mason-Pfizer monkey virus p12 protein" *Virology*, 2004, 324:204-212.

Chen, B. et al. "Efficient assembly of an HIV-1.MLV Gag-chimeric virus in murine cells" *PNAS*, 2001, 98(26):15239-15244.

Deminie, C. and Emerman, M. "Functional exchange of an oncoretrovirus and a lentivirus matrix protein" *J. Virology*, 1994, 68(7):4442-4449.

Deminie, C. and Emerman, M. "Incorporation of human immunodeficiency virus type 1 Gag proteins into murine leukemia virus virions" *J. Virology*, 1993, 67(11):6499-6506.

Dupraz, P. and Spahr, P-F. "Specificity of *Rous sarcoma* virus nucleocapsid protein in genomic RNA packaging" *J. Virology*, 1992, 66(8):4662-4670.

Reed, M. et al. "Chimeric human immunodeficiency virus type 1 containing murine leukemia virus matrix assembles in murine cells" *J. Virology*, 2002, 76(1):436-443.

Zábransky, A. et al. "Self-interacting domains within betaretrovirus gag polyproteins" presented at the EMBO/HHMI Central European Scientists Meeting, Budapest, Hungary, Feb. 7-9, 2005, abstract.

Rumlova, M. et al., "Gag Domains of Mason-Pfizer Monkey Virus Mediating Assembly of Capsids and 'Core related' Particles in Bacteria", *Retrovirus Assembly Meeting*; Prague, Czech Republic: Oct. 14-18, 2000, p. 111, paragraph 2.

Sun, R. et al., "Transmissable Retrovirus in Epstein—Barr Virus-Producer B95-8 Cells", *Virology*, 1995, pp. 374-383, vol. 209, No. 2, Academic Press, Inc.

Zabransky A. et al., "Identification of a Minimal HIV-1 Gag Domain Sufficient for Self-Association", *Virology*, Mar. 1, 2002, pp. 141-150, vol. 294, No. 1, Elsevier Science.

\* cited by examiner

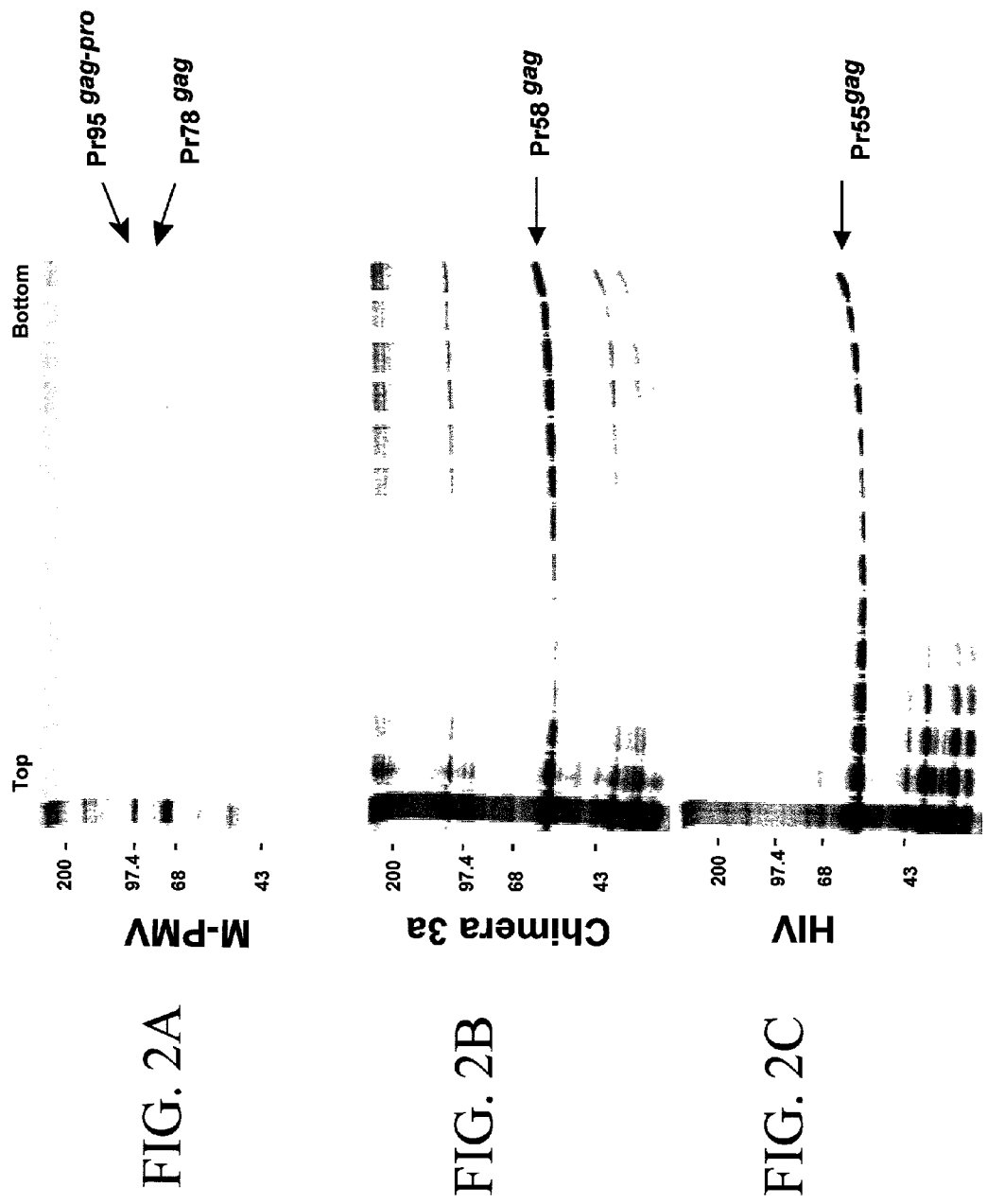

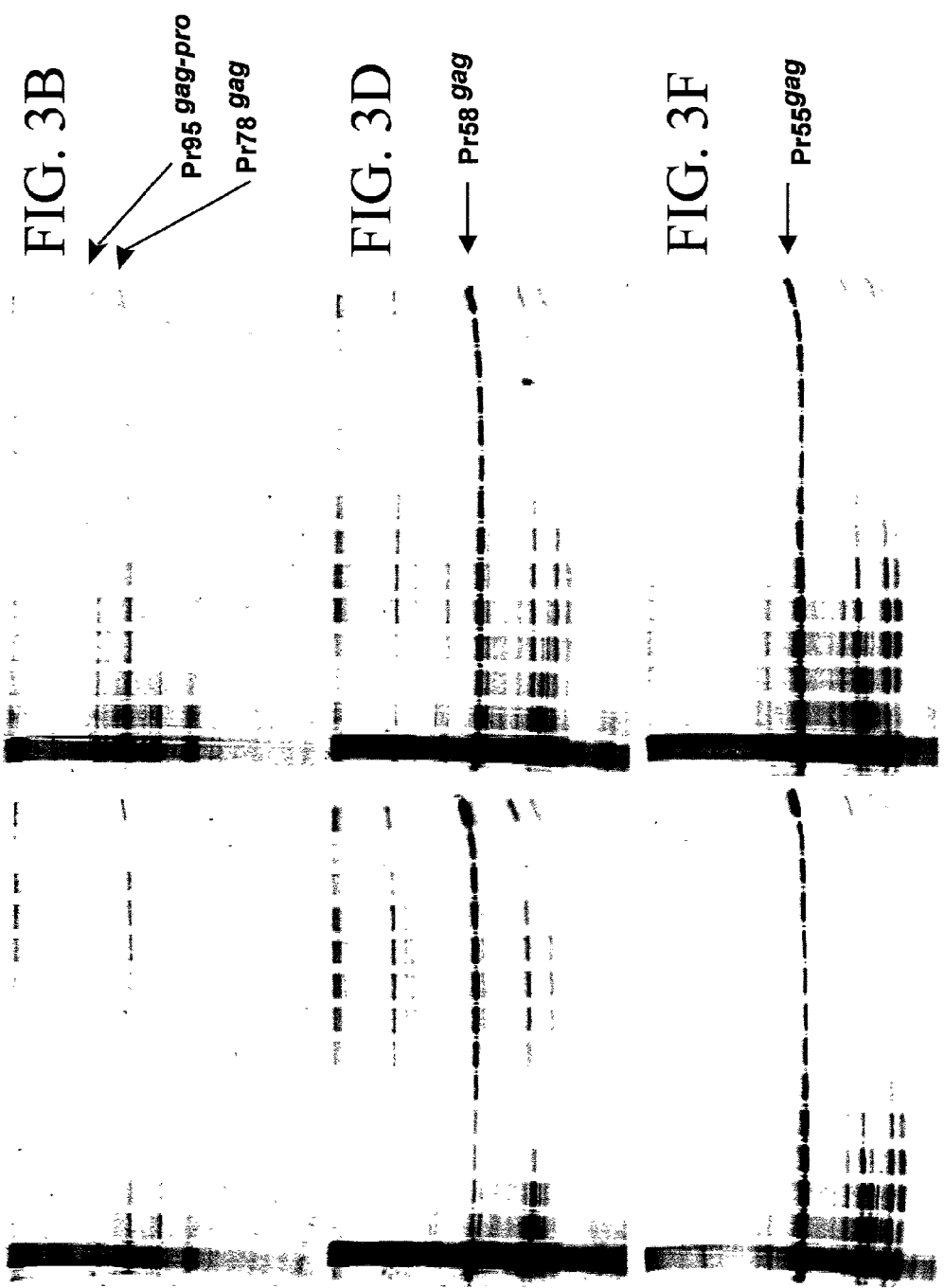
FIG. 3A FIG. 3B M-PMV — Pr95 gag-pro, Pr78 gag
FIG. 3C FIG. 3D Chimera 3a — Pr58 gag
FIG. 3E FIG. 3F HIV — Pr55 gag

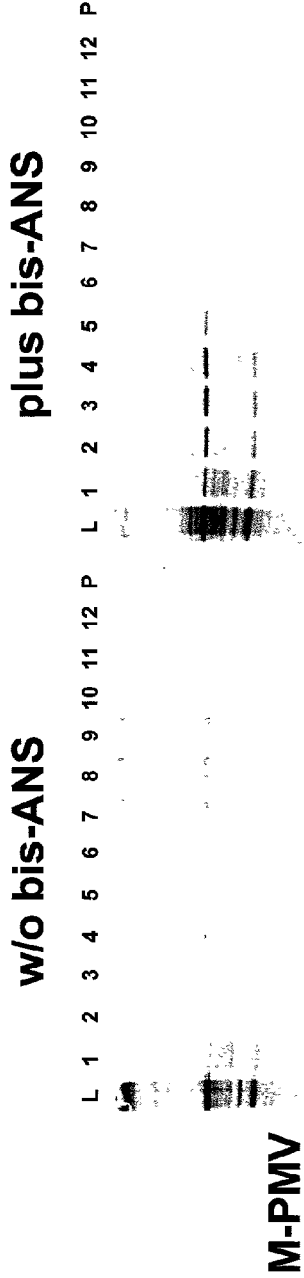
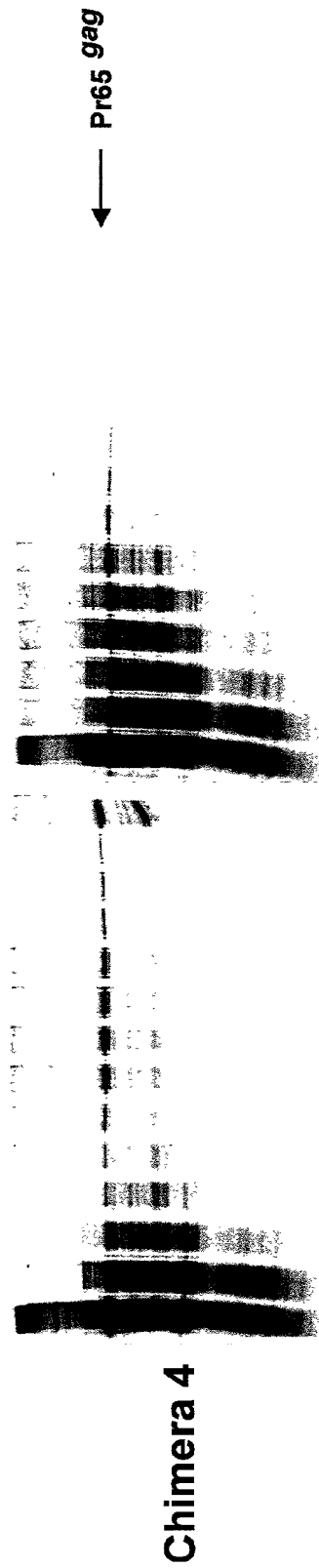
FIG. 4A  FIG. 4B
FIG. 4C  FIG. 4D

M-PMV

Chimera 4

Chimera 4

Chimera 4/
CA-M 185A

SEQUENCE LISTING

<160> NUMBER OF SEQ ID NOS: 26

<210> SEQ ID NO 1
<211> LENGTH: 12
<212> TYPE: RNA
<213> ORGANISM: Human immunodeficiency virus

<400> SEQUENCE: 1
aauuuuuuag gg                                                         12

<210> SEQ ID NO 2
<211> LENGTH: 29
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)..(29)
<223> OTHER INFORMATION: PCR primer

<400> SEQUENCE: 2
ggccagatct tcccgaggaa attagcctg                                       29

<210> SEQ ID NO 3
<211> LENGTH: 19
<212> TYPE: DNA
<213> ORGANISM: Artificial Sequence
<220> FEATURE:
<223> OTHER INFORMATION: PCR primer

<400> SEQUENCE: 3
ataagacaag gaccaaaag                                                  19

<210> SEQ ID NO 4
<211> LENGTH: 11
<212> TYPE: RNA
<213> ORGANISM: Artificial Sequence
<220> FEATURE:
<223> OTHER INFORMATION: Altered HIV frameshift signal sequence

<400> SEQUENCE: 4
aauuuccucg g                                                            11

<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
ataagacaag gaccaaagg                                                    19

<210> SEQ ID NO 6
<211> LENGTH: 17
<212> TYPE: DNA
<213> ORGANISM: Artificial Sequence
<220> FEATURE:
<223> OTHER INFORMATION: PCR primer

<400> SEQUENCE: 6
attagcctgt ctctcag                                                      17

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
gcggttgtta atccaaaaga gg                                                22

<210> SEQ ID NO 8
<211> LENGTH: 36
<212> TYPE: DNA
<213> ORGANISM: Artificial Sequence
<220> FEATURE:
<223> OTHER INFORMATION: PCR primer

<400> SEQUENCE: 8
atcaacggtc ccgggcactt agaaaatatc ttttgg                                 36

<210> SEQ ID NO 9
<211> LENGTH: 44
<212> TYPE: DNA
<213> ORGANISM: Artificial Sequence
<220> FEATURE:
<223> OTHER INFORMATION: PCR primer

<400> SEQUENCE: 9
ggggagaccc gggaattttg cggttgttaa tccaaaagag gagc                        44

<210> SEQ ID NO 10
<211> LENGTH: 46
<212> TYPE: DNA
<213> ORGANISM: Artificial Sequence
<220> FEATURE:
<223> OTHER INFORMATION: PCR primer

<400> SEQUENCE: 10
ggcaacgacc cctcgtcaca agcggttgtt aatccaaaag aggagc                      46

```
<210> SEQ ID NO 11
<211> LENGTH: 15
<212> TYPE: DNA
<213> ORGANISM: Artificial Sequence
<220> FEATURE:
<223> OTHER INFORMATION: PCR primer

<400> SEQUENCE: 11
ggcggttgtt aatcc                                                        15

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
cagctcgaga tacttgtgtg g                                                 21

<210> SEQ ID NO 13
<211> LENGTH: 17
<212> TYPE: DNA
<213> ORGANISM: Artificial Sequence
<220> FEATURE:
<223> OTHER INFORMATION: PCR primer

<400> SEQUENCE: 13
gatataccat ggggcaa                                                      17

<210> SEQ ID NO 14
<211> LENGTH: 16
<212> TYPE: DNA
<213> ORGANISM: Artificial Sequence
<220> FEATURE:
<223> OTHER INFORMATION: PCR primer

<400> SEQUENCE: 14
tcctctaatt gagcaa                                                       16

<210> SEQ ID NO 15
<211> LENGTH: 4594
<212> TYPE: DNA
<213> ORGANISM: Artificial Sequence
<220> FEATURE:
<223> OTHER INFORMATION: Plasmid pDABCh4

<400> SEQUENCE: 15
agcgcccaat acgcaaaccg cctctccccg cgcgttggcc gattcattaa tgcagctggc        60
acgacaggtt tcccgactgg aaagcgggca gtgagcgcaa cgcaattaat gtgagttagc       120
tcactcatta ggcaccccag gctttacact ttatgcttcc ggctcgtatg ttgtgtggaa       180
ttgtgagcgg ataacaattt cacacaggaa acagctatga ccatgattac gccaagctct       240
aatacgactc actataggga agcttaaac catgggtgcg agagcgtcag tattaagcgg       300
gggagaatta gatcgatggg aaaaaattcg gttaaggcca ggggaaaga aaaaatataa       360 attaaaacat atagtatggg caagcaggga gctagaacga ttcgcagtta atcctggcct       420
gttagaaaca tcagaaggct gtagacaaat actgggacag ctacaaccat cccttcagac       480
aggatcagaa gaacttagat cattatataa tacagtagca accctctatt gtgtgcatca       540
aaggatagag ataaaagaca ccaaggaagc tttagacaag atagaggaag agcaaaacaa       600
aagtaagaaa aaagcacagc aagcagcagc tgacacagga cacagcaatc aggtcagcca       660
```

-continued

| | |
|---|---|
| aaattaccct atagtgcaga acatccaggg gcaaatggta catcaggcca tatcacctag | 720 |
| aactttaaat gcatgggtaa aagtagtaga agagaaggct ttcagcccag aagtgatacc | 780 |
| catgttttca gcattatcag aaggagccac cccacaagat ttaaacacca tgctaaacac | 840 |
| agtgggggga catcaagcag ccatgcaaat gttaaaagag accatcaatg aggaagctgc | 900 |
| agaatgggat agagtacatc cagtgcatgc agggcctatt gcaccaggcc agatgagaga | 960 |
| accaagggga agtgacatag caggaactac tagtacccct caggaacaaa taggatggat | 1020 |
| gacaaataat ccacctatcc cagtaggaga aatttataaa agatggataa tcctgggatt | 1080 |
| aaataaaata gtaagaatgt atagccctac cagcattctg gacataagac aaggaccaaa | 1140 |
| agaacctttt agagactatg tagaccggtt ctataaaact ctaagagccg agcaagcttc | 1200 |
| acaggaggta aaaaattgga tgacagaaac cttgttggtc caaaatgcga acccagattg | 1260 |
| taagactatt ttaaaagcat tgggaccagc ggctacctta gaagaaatga tgacagcatg | 1320 |
| tcagggagta ggaggacccg gccataaggc aagagttttg gctgaagcaa tgagccaagt | 1380 |
| aacaaataca gctaccataa tgatgcagag aggcaatttt aggaaccaaa gaaagatggt | 1440 |
| taagtgtttc aattgtggca aagaagggca cacagccaga aattgcaggg cccctaggaa | 1500 |
| aaagggctgt tggaaatgtg gaaggaagg acaccaaatg aaagattgta ctgagagaca | 1560 |
| ggctaatttc ctcgggaaga tctgcccttc ctacaaggga aggccaggga attttcttca | 1620 |
| gagcagacca gagccaacag ccccaccaga agagagcttc aggtctgggg tagagacaac | 1680 |
| aactccccct cagaagcagg agccgataga caaggaactg tatcctttaa cttccctcag | 1740 |
| gtcactcttt ggcaacgacc cctcgtcaca ggcagttgtt aatccaaaag aggagctcaa | 1800 |
| agaaaaaatt gctcaattag aggaacagat taaattagaa gagttacacc aggcactaat | 1860 |
| ttccaaatta caaaaactaa aacagggaa tgaaactgta actcacccag acacagcagg | 1920 |
| aggcctttct cgcacgcctc actgcccagg gcaacatatc cctaaaggaa aatgttgcgc | 1980 |
| cagtcgagaa aaggaagaac aaatcccaaa agatattttc taagtgcccg ggtaccgagc | 2040 |
| tcgaattcac tggccgtcgt tttacaacgt cgtgactggg aaaaccctgg cgttacccaa | 2100 |
| cttaatcgcc ttgcagcaca tccccctttc gccagctggc gtaatagcga agaggcccgc | 2160 |
| accgatcgcc cttcccaaca gttgcgcagc ctgaatggcg aatgggaaat tgtaaacgtt | 2220 |
| aatattttgt taaaattcgc gttaaatttt tgttaaatca gctcattttt taaccaatag | 2280 |
| gccgaaatcg gcaaaatccc ttataaatca aagaataga ccgagatagg gttgagtgtt | 2340 |
| gttccagttt ggaacaagag tccactatta agaacgtgg actccaacgt caaagggcga | 2400 |
| aaaaccgtct atcagggcga tggcccacta cgtgaaccat caccctaatc aagttttttg | 2460 |
| gggtcgaggt gccgtaaagc actaaatcgg aaccctaaag ggagcccccg atttagagct | 2520 |
| tgacggggaa agccggcgaa cgtggcgaga aggaaggga agaaagcgaa aggagcgggc | 2580 |
| gctagggcgc tggcaagtgt agcggtcacg ctgcgcgtaa ccaccacacc cgccgcgctt | 2640 |
| aatgcgccgc tacagggcgc gtcaggtggc acttttcggg gaaatgtgcg cggaacccct | 2700 |
| atttgtttat ttttctaaat acattcaaat atgtatccgc tcatgagaca ataaccctga | 2760 |
| taaatgcttc aataatattg aaaaggaag agtatgagta ttcaacattt ccgtgtcgcc | 2820 |
| cttattccct ttttttgcggc atttttgcctt cctgtttttg ctcacccaga aacgctggtg | 2880 |
| aaagtaaaag atgctgaaga tcagttgggt gcacgagtgg gttacatcga actggatctc | 2940 |
| aacagcggta agatccttga gagttttcgc cccgaagaac gttttccaat gatgagcact | 3000 |
| tttaaagttc tgctatgtgg cgcggtatta tcccgtattg acgccgggca agagcaactc | 3060 |

| | |
|---|---|
| ggtcgccgca tacactattc tcagaatgac ttggttgagt actcaccagt cacagaaaag | 3120 |
| catcttacgg atggcatgac agtaagagaa ttatgcagtg ctgccataac catgagtgat | 3180 |
| aacactgcgg ccaacttact tctgacaacg atcggaggac cgaaggagct aaccgctttt | 3240 |
| ttgcacaaca tgggggatca tgtaactcgc cttgatcgtt gggaaccgga gctgaatgaa | 3300 |
| gccataccaa acgacgagcg tgacaccacg atgcctgtag caatggcaac aacgttgcgc | 3360 |
| aaactattaa ctggcgaact acttactcta gcttcccggc aacaattaat agactggatg | 3420 |
| gaggcggata agttgcagg accacttctg cgctcggccc ttccggctgg ctggtttatt | 3480 |
| gctgataaat ctggagccgg tgagcgtggg tctcgcggta tcattgcagc actggggcca | 3540 |
| gatggtaagc cctcccgtat cgtagttatc tacacgacgg ggagtcaggc aactatggat | 3600 |
| gaacgaaata gacagatcgc tgagataggt gcctcactga ttaagcattg gtaactgtca | 3660 |
| gaccaagttt actcatatat actttagatt gatttaaaac ttcattttta atttaaaagg | 3720 |
| atctaggtga agatcctttt tgataatctc atgaccaaaa tcccttaacg tgagttttcg | 3780 |
| ttccactgag cgtcagaccc cgtagaaaag atcaaaggat cttcttgaga tccttttttt | 3840 |
| ctgcgcgtaa tctgctgctt gcaaacaaaa aaaccaccgc taccagcggt ggtttgtttg | 3900 |
| ccggatcaag agctaccaac tcttttccg aaggtaactg gcttcagcag agcgcagata | 3960 |
| ccaaatactg tccttctagt gtagccgtag ttaggccacc acttcaagaa ctctgtagca | 4020 |
| ccgcctacat acctcgctct gctaatcctg ttaccagtgg ctgctgccag tggcgataag | 4080 |
| tcgtgtctta ccgggttgga ctcaagacga tagttaccgg ataaggcgca gcggtcgggc | 4140 |
| tgaacggggg gttcgtgcac acagcccagc ttggagcgaa cgacctacac cgaactgaga | 4200 |
| tacctacagc gtgagcattg agaaagcgcc acgcttcccg aagggagaaa ggcggacagg | 4260 |
| tatccggtaa gcggcagggt cggaacagga gagcgcacga gggagcttcc agggggaaac | 4320 |
| gcctggtatc tttatagtcc tgtcgggttt cgccacctct gacttgagcg tcgatttttg | 4380 |
| tgatgctcgt cagggggggcg gagcctatgg aaaaacgcca gcaacgcggc cttttacgg | 4440 |
| ttcctggcct tttgctggcc ttttgctcac atgttctttc ctgcgttatc ccctgattct | 4500 |
| gtggataacc gtattaccgc ctttgagtga gctgataccg ctcgccgcag ccgaacgacc | 4560 |
| gagcgcagcg agtcagtgag cgaggaagcg gaag | 4594 |

<210> SEQ ID NO 16
<211> LENGTH: 1752
<212> TYPE: DNA
<213> ORGANISM: Artificial Sequence
<220> FEATURE:
<223> OTHER INFORMATION: Chimera 4 sequence

<400> SEQUENCE: 16

| | |
|---|---|
| atgggtgcga gagcgtcagt attaagcggg ggagaattag atcgatggga aaaaattcgg | 60 |
| ttaaggccag ggggaaagaa aaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |

```
ccacaagatt taaacaccat gctaaacaca gtgggggggac atcaagcagc catgcaaatg    600
ttaaaagaga ccatcaatga ggaagctgca gaatgggata gagtacatcc agtgcatgca    660
gggcctattg caccaggcca gatgagagaa ccaaggggaa gtgacatagc aggaactact    720
agtacccttc aggaacaaat aggatggatg acaaataatc acctatccc agtaggagaa     780 atttataaaa gatggataat cctgggatta aataaaatag taagaatgta tagccctacc    840
agcattctgg acataagaca aggaccaaaa gaacctttta gagactatgt agaccggttc    900
tataaaactc taagagccga gcaagcttca caggaggtaa aaaattggat gacagaaacc    960
ttgttggtcc aaaatgcgaa cccagattgt aagactattt taaaagcatt gggaccagcg    1020
gctaccttag aagaaatgat gacagcatgt cagggagtag gaggacccgg ccataaggca    1080
agagttttgg ctgaagcaat gagccaagta acaaatacag ctaccataat gatgcagaga    1140 ggcaattttta ggaaccaaag aaagatggtt aagtgtttca attgtggcaa agaagggcac    1200
acagccagaa attgcagggc ccctaggaaa aagggctgtt ggaaatgtgg aaaggaagga    1260
caccaaatga aagattgtac tgagagacag gctaatttcc tcgggaagat ctggccttcc    1320
tacaagggaa ggccagggaa ttttcttcag agcagaccag agccaacagc cccaccagaa    1380
gagagcttca ggtctggggt agagacaaca actccccctc agaagcagga gccgatagac    1440
aaggaactgt atcctttaac ttccctcagg tcactctttg gcaacgaccc ctcgtcacag    1500
gcagttgtta atccaaaaga ggagctcaaa gaaaaaattg ctcaattaga ggaacagatt    1560
aaattagaag agttacacca ggcactaatt tccaaattac aaaaactaaa acagggaat    1620 gaaactgtaa ctcacccaga cacagcagga ggcctttctc gcacgcctca ctggccaggg    1680
caacatatcc ctaaaggaaa atgttgcgcc agtcgagaaa aggaagaaca atcccaaaa    1740 gatattttct aa                                                        1752
```

<210> SEQ ID NO 17
<211> LENGTH: 583
<212> TYPE: PRT
<213> ORGANISM: Artificial Sequence
<220> FEATURE:
<221> NAME/KEY: MISC_FEATURE
<222> LOCATION: (1)..(583)
<223> OTHER INFORMATION: Chimera 4 amino acid sequence

<400> SEQUENCE: 17

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125
```

-continued

```
Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Thr Ala Thr Ile Met Met Gln Arg Gly Asn Phe Arg
    370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln Ala Val Val Asn Pro Lys Glu Glu Leu Lys Glu Lys
            500                 505                 510

Ile Ala Gln Leu Glu Glu Gln Ile Lys Leu Glu Glu Leu His Gln Ala
        515                 520                 525

Leu Ile Ser Lys Leu Gln Lys Leu Lys Thr Gly Asn Glu Thr Val Thr
    530                 535                 540
```

```
His Pro Asp Thr Ala Gly Gly Leu Ser Arg Thr Pro His Trp Pro Gly
545                 550                 555                 560

Gln His Ile Pro Lys Gly Lys Cys Cys Ala Ser Arg Glu Lys Glu Glu
            565                 570                 575

Gln Ile Pro Lys Asp Ile Phe
            580

<210> SEQ ID NO 18
<211> LENGTH: 4390
<212> TYPE: DNA
<213> ORGANISM: Artificial Sequence
<220> FEATURE:
<223> OTHER INFORMATION: Plasmid pDABCh3a

<400> SEQUENCE: 18
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctct     240
aatacgactc actatagga aagcttaaac catgggtgcg agagcgtcag tattaagcgg     300
gggagaatta gatcgatggg aaaaaattcg gttaaggcca ggggggaaaga aaaatataa     360 attaaaacat atagtatggg caagcaggga gctagaacga ttcgcagtta atcctggcct     420
gttagaaaca tcagaaggct gtagacaaat actgggacag ctacaaccat cccttcagac     480
aggatcagaa gaacttagat cattatataa tacagtagca accctctatt gtgtgcatca     540
aaggatagag ataaaagaca ccaaggaagc tttagacaag atagaggaag agcaaaacaa     600
aagtaagaaa aagcacagc aagcagcagc tgacacagga cacagcaatc aggtcagcca     660
aaattaccct atagtgcaga acatccaggg gcaaatggta catcaggcca tatcacctag     720
aactttaaat gcatgggtaa agtagtagaa agagaaggct ttcagcccag aagtgatacc     780
catgttttca gcattatcag aaggagccac cccacaagat ttaaacacca tgctaaacac     840 agtggggga catcaagcag ccatgcaaat gttaaaagag accatcaatg aggaagctgc     900
agaatgggat agagtacatc cagtgcatgc agggcctatt gcaccaggcc agatgagaga     960
accaagggga agtgacatag caggaactac tagtaccctt caggaacaaa taggatggat    1020
gacaaataat ccacctatcc cagtaggaga aatttataaa agatggataa tcctgggatt    1080
aaataaaata gtaagaatgt atagccctac cagcattctg gacataagac aaggaccaaa    1140
agaaaccttt agagactatg tagaccggtt ctataaaact ctaagagccg agcaagcttc    1200
acaggaggta aaaaattgga tgacagaaac cttgttggtc caaaatgcga acccagattg    1260
taagactatt ttaaaagcat tgggaccagc ggctacctta aagaaatga tgacagcatg    1320 tcagggagta ggaggacccg gccataaggc aagagttttg gctgaagcaa tgagccaagt    1380
aacaaataca gctaccataa tgatgcagag aggcaatttt aggaaccaaa gaaagatggt    1440
taagtgtttc aattgtggca agagggca cacagccaga aattgcaggg ccctaggaa      1500 aaagggctgt tggaaatgtg gaaggaagg acaccaaatg aaagattgta ctgagagaca    1560
ggctaatgca gttgttaatc caaagagga gctcaaagaa aaaattgctc aattagagga    1620
acagattaaa ttagaagagt tacaccaggc actaattcc aaattacaaa actaaaaac     1680 agggaatgaa actgtaactc acccagacac agcaggaggc ctttctcgca cgcctcactg    1740
gccagggcaa catatcccta aggaaaatg ttgcgccagt cgagaaaagg aagaacaat     1800
```

```
cccaaaagat attttctaag tgcccgggta ccgagctcga attcactggc cgtcgtttta   1860
caacgtcgtg actgggaaaa ccctggcgtt acccaactta atcgccttgc agcacatccc   1920
cctttcgcca gctggcgtaa tagcgaagag gcccgcaccg atcgcccttc ccaacagttg   1980
cgcagcctga atggcgaatg ggaaattgta acgttaata ttttgttaaa attcgcgtta   2040
aatttttgtt aaatcagctc attttttaac caataggccg aaatcggcaa atcccttat   2100
aaatcaaaag aatagaccga gatagggttg agtgttgttc cagtttggaa caagagtcca   2160
ctattaaaga acgtggactc caacgtcaaa gggcgaaaaa ccgtctatca gggcgatggc   2220
ccactacgtg aaccatcacc ctaatcaagt tttttggggt cgaggtgccg taaagcacta   2280
aatcggaacc ctaaagggag cccccgattt agagcttgac ggggaaagcc ggcgaacgtg   2340
gcgagaaagg aagggaagaa agcgaaagga gcgggcgcta gggcgctggc aagtgtagcg   2400
gtcacgctgc gcgtaaccac cacacccgcc gcgcttaatg cgccgctaca gggcgcgtca   2460
ggtggcactt ttcggggaaa tgtgcgcgga acccctattt gtttattttt ctaaatacat   2520
tcaaatatgt atccgctcat gagacaataa ccctgataaa tgcttcaata atattgaaaa   2580
aggaagagta tgagtattca acatttccgt gtcgccctta ttccctttt tgcggcattt   2640
tgccttcctg ttttgctca cccagaaacg ctggtgaaag taaaagatgc tgaagatcag   2700
ttgggtgcac gagtgggtta catcgaactg gatctcaaca gcggtaagat ccttgagagt   2760
tttcgccccg aagaacgttt tccaatgatg agcacttta aagttctgct atgtggcgcg   2820
gtattatccc gtattgacgc cgggcaagag caactcggtc gccgcataca ctattctcag   2880
aatgacttgg ttgagtactc accagtcaca gaaaagcatc ttacggatgg catgacagta   2940
agagaattat gcagtgctgc cataaccatg agtgataaca ctgcggccaa cttacttctg   3000
acaacgatcg gaggaccgaa ggagctaacc gcttttttgc acaacatggg ggatcatgta   3060
actcgccttg atcgttggga accggagctg aatgaagcca taccaaacga cgagcgtgac   3120
accacgatgc ctgtagcaat ggcaacaacg ttgcgcaaac tattaactgg cgaactactt   3180
actctagctt cccggcaaca attaatagac tggatggagg cggataaagt tgcaggacca   3240
cttctgcgct cggcccttcc ggctggctgg tttattgctg ataaatctgg agccggtgag   3300
cgtgggtctc gcggtatcat tgcagcactg gggccagatg gtaagccctc ccgtatcgta   3360
gttatctaca cgacggggag tcaggcaact atggatgaac gaaatagaca gatcgctgag   3420
ataggtgcct cactgattaa gcattggtaa ctgtcagacc aagtttactc atatatactt   3480
tagattgatt taaaacttca tttttaattt aaaaggatct aggtgaagat cctttttgat   3540
aatctcatga ccaaaatccc ttaacgtgag ttttcgttcc actgagcgtc agacccgta   3600
gaaaagatca aggatcttc ttgagatcct ttttttctgc gcgtaatctg ctgcttgcaa   3660
acaaaaaaac caccgctacc agcggtggtt tgtttgccgg atcaagagct accaactctt   3720
tttccgaagg taactggctt cagcagagcg cagataccaa atactgtcct tctagtgtag   3780
ccgtagttag gccaccactt caagaactct gtagcaccgc ctacatacct cgctctgcta   3840
atcctgttac cagtggctgc tgccagtggc gataagtcgt gtcttaccgg gttggactca   3900
agacgatagt taccggataa ggcgcagcgg tcgggctgaa cggggggttc gtgcacacag   3960
cccagcttgg agcgaacgac ctacaccgaa ctgagatacc tacagcgtga gcattgagaa   4020
agcgccacgc ttcccgaagg gagaaaggcg gacaggtatc cggtaagcgg cagggtcgga   4080
acaggagagc gcacgaggga gcttccaggg ggaaacgcct ggtatcttta tagtcctgtc   4140
gggtttcgcc acctctgact tgagcgtcga ttttttgtgat gctcgtcagg gggcggagc   4200
```

| | |
|---|---|
| ctatggaaaa acgccagcaa cgcggccttt ttacggttcc tggccttttg ctggcctttt | 4260 |
| gctcacatgt tctttcctgc gttatcccct gattctgtgg ataaccgtat taccgccttt | 4320 |
| gagtgagctg ataccgctcg ccgcagccga acgaccgagc gcagcgagtc agtgagcgag | 4380 |
| gaagcggaag | 4390 |

<210> SEQ ID NO 19
<211> LENGTH: 1548
<212> TYPE: DNA
<213> ORGANISM: Artificial Sequence
<220> FEATURE:
<223> OTHER INFORMATION: Chimera Ch3a sequence

<400> SEQUENCE: 19

| | |
|---|---|
| atgggtgcga gagcgtcagt attaagcggg ggagaattag atcgatggga aaaaattcgg | 60 |
| ttaaggccag ggggaaagaa aaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtacatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |
| agcattctgg acataagaca aggaccaaaa gaaccttta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctaccttag aagaaatgat gacagcatgt cagggagtag gaggacccgg ccataaggca | 1080 |
| agagttttgg ctgaagcaat gagccaagta acaaatacag ctaccataat gatgcagaga | 1140 |
| ggcaatttta ggaaccaaag aaagatggtt aagtgtttca attgtggcaa agaagggcac | 1200 |
| acagccagaa attgcagggc ccctaggaaa aagggctgtt ggaaatgtgg aaaggaagga | 1260 |
| caccaaatga aagattgtac tgagagacag gctaatgcag ttgttaatcc aaaagaggag | 1320 |
| ctcaaagaaa aaattgctca attagaggaa cagattaaat tagaagagtt acaccaggca | 1380 |
| ctaatttcca aattacaaaa actaaaaaca gggaatgaaa ctgtaactca cccagacaca | 1440 |
| gcaggaggcc tttctcgcac gcctcactgg ccagggcaac atatccctaa aggaaaatgt | 1500 |
| tgcgccagtc gagaaaagga agaacaaatc ccaaaagata ttttctaa | 1548 |

<210> SEQ ID NO 20
<211> LENGTH: 515
<212> TYPE: PRT
<213> ORGANISM: Artificial Sequence
<220> FEATURE:
<221> NAME/KEY: MISC_FEATURE
<222> LOCATION: (1)..(515)
<223> OTHER INFORMATION: Ch3a amino acid sequence

<400> SEQUENCE: 20

```
Met Gly Ala Arg Ala Ser Val Leu Ser Gly Gly Glu Leu Asp Arg Trp
 1               5                  10                  15
Glu Lys Ile Arg Leu Arg Pro Gly Gly Lys Lys Tyr Lys Leu Lys
             20                  25                  30
His Ile Val Trp Ala Ser Arg Glu Leu Glu Arg Phe Ala Val Asn Pro
             35                  40                  45
Gly Leu Leu Glu Thr Ser Glu Gly Cys Arg Gln Ile Leu Gly Gln Leu
 50                  55                  60
Gln Pro Ser Leu Gln Thr Gly Ser Glu Glu Leu Arg Ser Leu Tyr Asn
 65                  70                  75                  80
Thr Val Ala Thr Leu Tyr Cys Val His Gln Arg Ile Glu Ile Lys Asp
                 85                  90                  95
Thr Lys Glu Ala Leu Asp Lys Ile Glu Glu Gln Asn Lys Ser Lys
             100                 105                 110
Lys Lys Ala Gln Gln Ala Ala Asp Thr Gly His Ser Asn Gln Val
             115                 120                 125
Ser Gln Asn Tyr Pro Ile Val Gln Asn Ile Gln Gly Gln Met Val His
130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                 165                 170                 175
Glu Gly Ala Thr Pro Gln Asp Leu Asn Thr Met Leu Asn Thr Val Gly
             180                 185                 190
Gly His Gln Ala Ala Met Gln Met Leu Lys Glu Thr Ile Asn Glu Glu
             195                 200                 205
Ala Ala Glu Trp Asp Arg Val His Pro Val His Ala Gly Pro Ile Ala
210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                 245                 250                 255
Pro Val Gly Glu Ile Tyr Lys Arg Trp Ile Ile Leu Gly Leu Asn Lys
             260                 265                 270
Ile Val Arg Met Tyr Ser Pro Thr Ser Ile Leu Asp Ile Arg Gln Gly
             275                 280                 285
Pro Lys Glu Pro Phe Arg Asp Tyr Val Asp Arg Phe Tyr Lys Thr Leu
290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                 325                 330                 335
Leu Gly Pro Ala Ala Thr Leu Glu Glu Met Met Thr Ala Cys Gln Gly
             340                 345                 350
Val Gly Gly Pro Gly His Lys Ala Arg Val Leu Ala Glu Ala Met Ser
             355                 360                 365
Gln Val Thr Asn Thr Ala Thr Ile Met Met Gln Arg Gly Asn Phe Arg
370                 375                 380
Asn Gln Arg Lys Met Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
                 405                 410                 415
```

```
Gly Lys Glu Gly His Gln Met Lys Asp Cys Thr Arg Gln Ala Asn
            420                 425                 430
Ala Val Val Asn Pro Lys Glu Leu Lys Glu Lys Ile Ala Gln Leu
            435                 440                 445
Glu Glu Gln Ile Lys Leu Glu Leu His Gln Ala Leu Ile Ser Lys
            450                 455                 460
Leu Gln Lys Leu Lys Thr Gly Asn Glu Thr Val Thr His Pro Asp Thr
465                 470                 475                 480
Ala Gly Gly Leu Ser Arg Thr Pro His Trp Pro Gly Gln His Ile Pro
                485                 490                 495
Lys Gly Lys Cys Cys Ala Ser Arg Glu Lys Glu Gln Ile Pro Lys
            500                 505                 510
Asp Ile Phe
        515

<210> SEQ ID NO 21
<211> LENGTH: 4438
<212> TYPE: DNA
<213> ORGANISM: Artificial Sequence
<220> FEATURE:
<223> OTHER INFORMATION: Plasmid pDABCh3

<400> SEQUENCE: 21
```

| | | | | |
|---|---|---|---|---|
| agcgcccaat | acgcaaaccg | cctctccccg | cgcgttggcc | gattcattaa tgcagctggc | 60 |
| acgacaggtt | tcccgactgg | aaagcgggca | gtgagcgcaa | cgcaattaat gtgagttagc | 120 |
| tcactcatta | ggcaccccag | gctttacact | ttatgcttcc | ggctcgtatg ttgtgtggaa | 180 |
| ttgtgagcgg | ataacaattt | cacacaggaa | acagctatga | ccatgattac gccaagctct | 240 |
| aatacgactc | actataggga | aagcttaaac | catgggtgcg | agagcgtcag tattaagcgg | 300 |
| gggagaatta | gatcgatggg | aaaaaattcg | gttaaggcca | gggggaaaga aaaaatataa | 360 |
| attaaaacat | atagtatggg | caagcaggga | gctagaacga | ttcgcagtta atcctggcct | 420 |
| gttagaaaca | tcagaaggct | gtagacaaat | actgggacag | ctacaaccat cccttcagac | 480 |
| aggatcagaa | gaacttagat | cattatataa | tacagtagca | accctctatt gtgtgcatca | 540 |
| aaggatagag | ataaaagaca | ccaaggaagc | tttagacaag | atagaggaag agcaaaacaa | 600 |
| aagtaagaaa | aaagcacagc | aagcagcagc | tgacacagga | cacagcaatc aggtcagcca | 660 |
| aaattaccct | atagtgcaga | acatccaggg | gcaaatggta | catcaggcca tatcacctag | 720 |
| aactttaaat | gcatgggtaa | aagtagtaga | agagaaggct | ttcagcccag aagtgatacc | 780 |
| catgttttca | gcattatcag | aaggagccac | cccacaagat | ttaaacacca tgctaaacac | 840 |
| agtgggggga | catcaagcag | ccatgcaaat | gttaaaagag | accatcaatg aggaagctgc | 900 |
| agaatgggat | agagtacatc | cagtgcatgc | agggcctatt | gcaccaggcc agatgagaga | 960 |
| accaagggga | agtgacatag | caggaactac | tagtacccct | caggaacaaa taggatggat | 1020 |
| gacaaataat | ccacctatcc | cagtaggaga | aatttataaa | agatggataa tcctgggatt | 1080 |
| aaataaaata | gtaagaatgt | atagccctac | cagcattctg | gacataagac aaggaccaaa | 1140 |
| agaacctttt | agagactatg | tagaccggtt | ctataaaact | ctaagagccg agcaagcttc | 1200 |
| acaggaggta | aaaaattgga | tgacagaaac | cttgttggtc | caaatgcgaa cccagattg | 1260 |
| taagactatt | ttaaaagcat | tgggaccagc | ggctaccttaa | gaagaaatga tgacagcatg | 1320 |
| tcagggagta | ggaggacccg | gccataaggc | aagagttttg | gctgaagcaa tgagccaagt | 1380 |
| aacaaataca | gctaccataa | tgatgcagag | aggcaatttt | aggaaccaaa gaaagatggt | 1440 |

```
taagtgtttc aattgtggca agaagggca cacagccaga aattgcaggg ccctaggaa    1500
aaagggctgt tggaaatgtg gaaaggaagg acaccaaatg aaagattgta ctgagagaca   1560
ggctaatttc ctcgggaaga tctggccctc atacaagggg agaccaggga attttgcggt   1620
tgttaatcca aaagaggagc tcaaagaaaa aattgctcaa ttagaggaac agattaaatt   1680
agaagagtta caccaggcac taatttccaa attacaaaaa ctaaaaacag ggaatgaaac   1740
tgtaactcac ccagacacag caggaggcct ttctcgcacg cctcactggc cagggcaaca   1800
tatccctaaa ggaaaatgtt gcgccagtcg agaaaaggaa gaacaaatcc caaaagatat   1860
tttctaagtg cccgggtacc gagctcgaat tcactggccg tcgttttaca acgtcgtgac   1920
tgggaaaacc ctggcgttac ccaacttaat cgccttgcag cacatccccc tttcgccagc   1980
tggcgtaata gcgaagaggc ccgcaccgat cgcccttccc aacagttgcg cagcctgaat   2040
ggcgaatggg aaattgtaaa cgttaatatt tgttaaaat tcgcgttaaa tttttgttaa    2100
atcagctcat tttttaacca ataggccgaa atcggcaaaa tcccttataa atcaaaagaa   2160
tagaccgaga tagggttgag tgttgttcca gtttggaaca agagtccact attaaagaac   2220
gtggactcca acgtcaaagg gcgaaaaacc gtctatcagg gcgatggccc actacgtgaa   2280
ccatcacccct aatcaagttt tttggggtcg aggtgccgta aagcactaaa tcggaaccct  2340
aaagggagcc cccgatttag agcttgacgg ggaaagccgg cgaacgtggc gagaaaggaa   2400
gggaagaaag cgaaaggagc gggcgctagg gcgctggcaa gtgtagcggt cacgctgcgc   2460
gtaaccacca caccccgccgc gcttaatgcg ccgctacagg gcgcgtcagg tggcactttt   2520
cggggaaatg tgcgcggaac ccctatttgt ttattttct aaatacattc aaatatgtat    2580
ccgctcatga caataaacc ctgataaatg cttcaataat attgaaaaag gaagagtatg    2640
agtattcaac atttccgtgt cgcccttatt cccttttttg cggcattttg ccttcctgtt   2700
tttgctcacc cagaaacgct ggtgaaagta aaagatgctg aagatcagtt gggtgcacga   2760
gtgggttaca tcgaactgga tctcaacagc ggtaagatcc ttgagagttt cgccccgaa    2820
gaacgttttc caatgatgag cacttttaaa gttctgctat gtggcgcggt attatcccgt   2880
attgacgccg ggcaagagca actcggtcgc cgcatacact attctcagaa tgacttggtt   2940
gagtactcac cagtcacaga aaagcatctt acggatggca tgacagtaag agaattatgc   3000
agtgctgcca taaccatgag tgataacact gcggccaact tacttctgac aacgatcgga   3060
ggaccgaagg agctaaccgc ttttttgcac aacatggggg atcatgtaac tcgccttgat   3120
cgttgggaac cggagctgaa tgaagccata ccaaacgacg agcgtgacac cacgatgcct   3180
gtagcaatgg caacaacgtt gcgcaaacta ttaactggcg aactacttac tctagcttcc   3240
cggcaacaat taatagactg gatggaggcg gataaagttg caggaccact tctgcgctcg   3300
gcccttccgg ctggctggtt tattgctgat aaatctggag ccggtgagcg tgggtctcgc   3360
ggtatcattg cagcactggg gccagatggt aagccctccc gtatcgtagt tatctacacg   3420
acggggagtc aggcaactat ggatgaacga atagacaga tcgctgagat aggtgcctca   3480
ctgattaagc attggtaact gtcagaccaa gtttactcat atatacttta gattgattta   3540
aaacttcatt tttaatttaa aaggatctag gtgaagatcc ttttttgataa tctcatgacc   3600
aaaatccctt aacgtgagtt ttcgttccac tgagcgtcag accccgtaga aaagatcaaa   3660
ggatcttctt gagatccttt ttttctgcgc gtaatctgct gcttgcaaac aaaaaaacca   3720
ccgctaccag cggtggtttg tttgccggat caagagctac caactctttt tccgaaggta   3780
actggcttca gcagagcgca gataccaaat actgtccttc tagtgtagcc gtagttaggc   3840
```

| | | | | |
|---|---|---|---|---|
| caccacttca | agaactctgt | agcaccgcct | acatacctcg | ctctgctaat cctgttacca | 3900 |
| gtggctgctg | ccagtggcga | taagtcgtgt | cttaccgggt | tggactcaag acgatagtta | 3960 |
| ccggataagg | cgcagcggtc | gggctgaacg | gggggttcgt | gcacacagcc cagcttggag | 4020 |
| cgaacgacct | acaccgaact | gagataccta | cagcgtgagc | attgagaaag cgccacgctt | 4080 |
| cccgaaggga | gaaaggcgga | caggtatccg | gtaagcggca | gggtcggaac aggagagcgc | 4140 |
| acgagggagc | ttccagggg | aaacgcctgg | tatctttata | gtcctgtcgg gtttcgccac | 4200 |
| ctctgacttg | agcgtcgatt | tttgtgatgc | tcgtcagggg | gcggagcct atggaaaaac | 4260 |
| gccagcaacg | cggccttttt | acggttcctg | gccttttgct | ggccttttgc tcacatgttc | 4320 |
| tttcctgcgt | tatcccctga | ttctgtggat | aaccgtatta | ccgcctttga gtgagctgat | 4380 |
| accgctcgcc | gcagccgaac | gaccgagcgc | agcgagtcag | tgagcgagga agcggaag | 4438 |

<210> SEQ ID NO 22
<211> LENGTH: 1596
<212> TYPE: DNA
<213> ORGANISM: Artificial Sequence
<220> FEATURE:
<223> OTHER INFORMATION: Ch3 DNA sequence

<400> SEQUENCE: 22

| | | | | |
|---|---|---|---|---|
| atgggtgcga | gagcgtcagt | attaagcggg | ggagaattag | atcgatggga aaaaattcgg | 60 |
| ttaaggccag | ggggaaagaa | aaatataaa | ttaaaacata | tagtatgggc aagcagggag | 120 |
| ctagaacgat | tcgcagttaa | tcctggcctg | ttagaaacat | cagaaggctg tagacaaata | 180 |
| ctgggacagc | tacaaccatc | ccttcagaca | ggatcagaag | aacttagatc attatataat | 240 |
| acagtagcaa | ccctctattg | tgtgcatcaa | aggatagaga | taaaagacac caaggaagct | 300 |
| ttagacaaga | tagaggaaga | gcaaaacaaa | agtaagaaaa | agcacagca agcagcagct | 360 |
| gacacaggac | acagcaatca | ggtcagccaa | aattacccta | tagtgcagaa catccagggg | 420 |
| caaatggtac | atcaggccat | atcacctaga | actttaaatg | catgggtaaa agtagtagaa | 480 |
| gagaaggctt | tcagcccaga | agtgataccc | atgttttcag | cattatcaga aggagccacc | 540 |
| ccacaagatt | taaacaccat | gctaaacaca | gtggggggac | atcaagcagc catgcaaatg | 600 |
| ttaaaagaga | ccatcaatga | ggaagctgca | gaatgggata | gagtacatcc agtgcatgca | 660 |
| gggcctattg | caccaggcca | gatgagagaa | ccaaggggaa | gtgacatagc aggaactact | 720 |
| agtacccttc | aggaacaaat | aggatggatg | acaaataatc | cacctatccc agtaggagaa | 780 |
| atttataaaa | gatggataat | cctgggatta | aataaaatag | taagaatgta tagccctacc | 840 |
| agcattctgg | acataagaca | aggaccaaaa | gaaccttta | gagactatgt agaccggttc | 900 |
| tataaaactc | taagagccga | gcaagcttca | caggaggtaa | aaaattggat gacagaaacc | 960 |
| ttgttggtcc | aaaatgcgaa | cccagattgt | aagactattt | taaaagcatt gggaccagcg | 1020 |
| gctaccttag | aagaaatgat | gacagcatgt | cagggagtag | gaggacccgg ccataaggca | 1080 |
| agagttttgg | ctgaagcaat | gagccaagta | acaaatacag | ctaccataat gatgcagaga | 1140 |
| ggcaatttta | ggaaccaaag | aaagatggtt | aagtgtttca | attgtggcaa agaagggcac | 1200 |
| acagccagaa | attgcagggc | ccctaggaaa | aagggctgtt | ggaaatgtgg aaggaagga | 1260 |
| caccaaatga | aagattgtac | tgagagacag | gctaatttcc | tcgggaagat ctggccctca | 1320 |
| tacaagggga | gaccagggaa | ttttgcggtt | gttaatccaa | agaggagct caaagaaaaa | 1380 |
| attgctcaat | tagaggaaca | gattaaatta | gaagagttac | accaggcact aatttccaaa | 1440 |
| ttacaaaaac | taaaaacagg | gaatgaaact | gtaactcacc | cagacacagc aggaggcctt | 1500 |

```
tctcgcacgc tcactggcc agggcaacat atccctaaag gaaatgttg cgccagtcga    1560 gaaaaggaag aacaaatccc aaagatatt ttctaa                              1596
```

<210> SEQ ID NO 23
<211> LENGTH: 531
<212> TYPE: PRT
<213> ORGANISM: Artificial Sequence
<220> FEATURE:
<221> NAME/KEY: MISC_FEATURE
<222> LOCATION: (1)..(531)
<223> OTHER INFORMATION: Ch3 amino acid sequence

<400> SEQUENCE: 23

```
Met Gly Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
    115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
    195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
    275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335
```

```
Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Thr Ala Thr Ile Met Met Gln Arg Gly Asn Phe Arg
        370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Ala Val Val Asn Pro Lys Glu Glu Leu Lys Glu Lys Ile Ala Gln Leu
    450                 455                 460

Glu Glu Gln Ile Lys Leu Glu Leu His Gln Ala Leu Ile Ser Lys
465                 470                 475                 480

Leu Gln Lys Leu Lys Thr Gly Asn Glu Thr Val Thr His Pro Asp Thr
                485                 490                 495

Ala Gly Gly Leu Ser Arg Thr Pro His Trp Pro Gly Gln His Ile Pro
            500                 505                 510

Lys Gly Lys Cys Cys Ala Ser Arg Glu Lys Glu Glu Gln Ile Pro Lys
        515                 520                 525

Asp Ile Phe
    530

<210> SEQ ID NO 24
<211> LENGTH: 4516
<212> TYPE: DNA
<213> ORGANISM: Artificial Sequence
<220> FEATURE:
<223> OTHER INFORMATION: Plasmid pDAB72 (FS-)

<400> SEQUENCE: 24
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctct     240
aatacgactc actatagggA agcttaaac catgggtgcg agagcgtcag tattaagcgg     300
gggagaatta gatcgatggg aaaaaattcg gttaaggcca gggggaaaga aaaaatataa     360
attaaaacat atagtatggg caagcaggga gctagaacga ttcgcagtta atcctggcct     420
gttagaaaca tcagaaggct gtagacaaat actgggacag ctacaaccat cccttcagac     480
aggatcagaa gaacttagat cattatataa tacagtagca accctctatt gtgtgcatca     540
aaggatagag ataaaagaca ccaaggaagc tttagacaag atagaggaag agcaaaacaa     600
aagtaagaaa aaagcacagc aagcagcagc tgacacagga cacagcaatc aggtcagcca     660
aaattaccct atagtgcaga acatccaggg gcaaatggta catcaggcca tatcacctag     720
aactttaaat gcatgggtaa aagtagtaga agagaaggct ttcagcccag aagtgatacc     780
catgttttca gcattatcag aaggagccac cccacaagat ttaaacacca tgctaaacac     840
agtgggggga catcaagcag ccatgcaaat gttaaaagag accatcaatg aggaagctgc     900
```

-continued

| | |
|---|---|
| agaatgggat agagtacatc cagtgcatgc agggcctatt gcaccaggcc agatgagaga | 960 |
| accaagggga agtgacatag caggaactac tagtacccTt caggaacaaa taggatggat | 1020 |
| gacaaataat ccacctatcc cagtaggaga aatttataaa agatggataa tcctgggatt | 1080 |
| aaataaaata gtaagaatgt atagccctac cagcattctg acataagac aaggaccaaa | 1140 |
| agaaccttTt agagactatg tagaccggtt ctataaaact ctaagagccg agcaagcttc | 1200 |
| acaggaggta aaaaattgga tgacagaaac cttgttggtc caaaatgcga acccagattg | 1260 |
| taagactatt ttaaaagcat tgggaccagc ggctacctta aagaaatga tgacagcatg | 1320 |
| tcagggagta ggaggacccg gccataaggc aagagttttg gctgaagcaa tgagccaagt | 1380 |
| aacaaataca gctaccataa tgatgcagag aggcaatttt aggaaccaaa gaaagatggt | 1440 |
| taagtgtttc aattgtggca aagaagggca cacagccaga aattgcaggg cccctaggaa | 1500 |
| aaagggctgt tggaaatgtg gaaggaagg acaccaaatg aaagattgta ctgagagaca | 1560 |
| ggctaatttc ctcgggaaga tctggccttc ctacaaggga aggccaggga attttcttca | 1620 |
| gagcagacca gagccaacag ccccaccaga agagagcttc aggtctgggg tagagacaac | 1680 |
| aactccccct cagaagcagg agccgataga caaggaactg tatccttTaa cttccctcag | 1740 |
| gtcactcttt ggcaacgacc cctcgtcaca ataaagatag gggggcaact aaaggaagct | 1800 |
| ctattagata caggagcaga tgatacagta ttagaagaaa tgagtttgcc aggaagatgg | 1860 |
| aaaccaaaaa tgatagggg aattggaggt tttatcaaag taagacagta tgatcagata | 1920 |
| ctcatagaaa tctgtggact tggggatccc cgggtaccga gctcgaattc actggccgtc | 1980 |
| gttttacaac gtcgtgactg ggaaaaccct ggcgttaccc aacttaatcg ccttgcagca | 2040 |
| catccccctt tcgccagctg gcgtaatagc gaagaggccc gcaccgatcg cccttcccaa | 2100 |
| cagttgcgca gcctgaatgg cgaatgggaa attgtaaacg ttaatattTt gttaaaattc | 2160 |
| gcgttaaatt ttTgttaaat cagctcatTt tttaaccaat aggccgaaat cggcaaaatc | 2220 |
| ccttataaat caaagaata gaccgagata gggttgagtg ttgttccagt ttggaacaag | 2280 |
| agtccactat taagaacgt ggactccaac gtcaaagggc gaaaaaccgt ctatcagggc | 2340 |
| gatggcccac tacgtgaacc atcaccctaa tcaagttttt tggggtcgag gtgccgtaaa | 2400 |
| gcactaaatc ggaaccctaa agggagcccc cgatttagag cttgacgggg aaagccggcg | 2460 |
| aacgtggcga gaaaggaagg gaagaaagcg aaaggagcgg gcgctagggc gctggcaagt | 2520 |
| gtagcggtca cgctgcgcgt aaccaccaca cccgccgcgc ttaatgcgcc gctacagggc | 2580 |
| gcgtcaggtg cacttttcg gggaaatgtg cgcggaaccc ctattTgttt attTtttctaa | 2640 |
| atacattcaa atatgtatcc gctcatgaga caataaccct gataaatgct tcaataatat | 2700 |
| tgaaaaagga agagtatgag tattcaacat tTccgtgtcg cccttattcc cttTttTtgcg | 2760 |
| gcattTtgcc ttcctgttTt tgctcaccca gaaacgctgg tgaaagtaaa agatgctgaa | 2820 |
| gatcagttgg gtgcacagt gggttacatc gaactggatc tcaacagcgg taagatcctt | 2880 |
| gagagtttTc gccccgaaga acgttTtcca atgatgagca cttTtaaagt tctgctatgt | 2940 |
| ggcgcggtat tatcccgtat tgacgccggg caagagcaac tcggtcgccg catacactat | 3000 |
| tctcagaatg acttggtTga gtactcacca gtcacagaaa agcatcttac ggatggcatg | 3060 |
| acagtaagag aattatgcag tgctgccata accatgagt ataacactgc ggccaactta | 3120 |
| cttctgacaa cgatcggagg accgaaggag ctaaccgctt ttTtgcacaa catgggggat | 3180 |
| catgtaactc gccttgatcg ttgggaaccg gagctgaatg aagccatacc aaacgacgag | 3240 |
| cgtgacacca cgatgcctgt agcaatggca acaacgttgc gcaaactatt aactggcgaa | 3300 |

| | |
|---|---|
| ctacttactc tagcttcccg gcaacaatta atagactgga tggaggcgga taaagttgca | 3360 |
| ggaccacttc tgcgctcggc ccttccggct ggctggttta ttgctgataa atctggagcc | 3420 |
| ggtgagcgtg gtctcgcgg tatcattgca gcactgggc cagatggtaa gccctcccgt | 3480 |
| atcgtagtta tctacacgac ggggagtcag gcaactatgg atgaacgaaa tagacagatc | 3540 |
| gctgagatag gtgcctcact gattaagcat tggtaactgt cagaccaagt ttactcatat | 3600 |
| atactttaga ttgatttaaa acttcatttt taatttaaaa ggatctaggt gaagatcctt | 3660 |
| tttgataatc tcatgaccaa atcccttaa cgtgagtttt cgttccactg agcgtcagac | 3720 |
| cccgtagaaa agatcaaagg atcttcttga gatccttttt ttctgcgcgt aatctgctgc | 3780 |
| ttgcaaacaa aaaaccacc gctaccagcg gtggtttgtt tgccggatca agagctacca | 3840 |
| actcttttc cgaaggtaac tggcttcagc agagcgcaga taccaaatac tgtccttcta | 3900 |
| gtgtagccgt agttaggcca ccacttcaag aactctgtag caccgcctac atacctcgct | 3960 |
| ctgctaatcc tgttaccagt ggctgctgcc agtggcgata gtcgtgtct taccgggttg | 4020 |
| gactcaagac gatagttacc ggataaggcg cagcggtcgg gctgaacggg gggttcgtgc | 4080 |
| acacagccca gcttggagcg aacgacctac accgaactga atacctaca gcgtgagcat | 4140 |
| tgagaaagcg ccacgcttcc gaagggaga aaggcggaca ggtatccggt aagcggcagg | 4200 |
| gtcggaacag gagagcgcac gagggagctt ccagggggaa acgcctggta tctttatagt | 4260 |
| cctgtcgggt ttcgccacct ctgacttgag cgtcgatttt tgtgatgctc gtcaggggg | 4320 |
| cggagcctat ggaaaaacgc cagcaacgcg gcctttttac ggttcctggc cttttgctgg | 4380 |
| ccttttgctc acatgttctt tcctgcgtta tcccctgatt ctgtggataa ccgtattacc | 4440 |
| gcctttgagt gagctgatac cgctcgccgc agccgaacga ccgagcgcag cgagtcagtg | 4500 |
| agcgaggaag cggaag | 4516 |

<210> SEQ ID NO 25
<211> LENGTH: 1503
<212> TYPE: DNA
<213> ORGANISM: Human immunodeficiency virus
<220> FEATURE:
<221> NAME/KEY: misc_feature
<222> LOCATION: (1)..(1503)
<223> OTHER INFORMATION: HIV Gag (FS-) DNA sequence

<400> SEQUENCE: 25

| | |
|---|---|
| atgggtgcga gagcgtcagt attaagcggg ggagaattag atcgatggga aaaaattcgg | 60 |
| ttaaggccag ggggaaagaa aaatataaa ttaaaacata tagtatggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta gtgtcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtacatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc gtaggagaa | 780 |

-continued

```
atttataaaa gatggataat cctgggatta aataaaatag taagaatgta tagccctacc    840
agcattctgg acataagaca aggaccaaaa gaaccttta gagactatgt agaccggttc    900
tataaaactc taagagccga gcaagcttca caggaggtaa aaattggat gacagaaacc    960 ttgttggtcc aaaatgcgaa cccagattgt aagactattt taaaagcatt gggaccagcg    1020
gctaccttag aagaaatgat gacagcatgt cagggagtag gaggacccgg ccataaggca    1080
agagttttgg ctgaagcaat gagccaagta acaaatacag ctaccataat gatgcagaga    1140
ggcaatttta ggaaccaaag aaagatggtt aagtgtttca attgtggcaa agaagggcac    1200
acagccagaa attgcagggc ccctaggaaa aagggctgtt ggaaatgtgg aaaggaagga    1260
caccaaatga aagattgtac tgagagacag gctaatttcc tcgggaagat ctggccttcc    1320
tacaagggaa ggccagggaa tttcttcag agcagaccag agccaacagc cccaccagaa    1380
gagagcttca ggtctggggt agagacaaca actccccctc agaagcagga gccgatagac    1440
aaggaactgt atcctttaac ttccctcagg tcactctttg gcaacgaccc ctcgtcacaa    1500
taa                                                                 1503
```

<210> SEQ ID NO 26
<211> LENGTH: 500
<212> TYPE: PRT
<213> ORGANISM: Human immunodeficiency virus
<220> FEATURE:
<221> NAME/KEY: MISC_FEATURE
<222> LOCATION: (1)..(500)
<223> OTHER INFORMATION: HIV (FS-) GAG amino acid sequence

<400> SEQUENCE: 26

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220
```

-continued

```
Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
        290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
            355                 360                 365

Gln Val Thr Asn Thr Ala Thr Ile Met Met Gln Arg Gly Asn Phe Arg
        370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
            435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500
```

CHIMERIC RETROVIRAL GAG GENES AND SCREENING ASSAYS

CROSS-REFERENCE TO RELATED APPLICATION

This application claims priority to U.S. Provisional Application Ser. No. 60/236,273, filed Sep. 28, 2000, which is hereby incorporated by reference in its entirety, including all sequences, figures, and tables.

The subject invention was made with government support under a research project supported by NIH Grant No. 43230. The government may have certain rights in this invention.

BACKGROUND OF THE INVENTION

Retrovirus assembly, a key step in the viral replication cycle, involves a process in which a large number of chemically distinct macromolecules are transported through different pathways to a single point at the plasma membrane of the cell where they are assembled into a nascent viral particle. The internal protein shell or capsid of the virus is assembled from a large number of polyprotein precursors that must be transported through the cytoplasm, either preassembled, in small groups, or as monomers to the underside of the plasma membrane. The membrane-spanning viral glycoproteins, on the other hand, must be transported through the secretory pathway of the cell to the plasma membrane where they co-localize with the nascent, membrane-extruding capsid. At a point still undetermined in the capsid assembly process, genome-length viral RNA molecules, along with necessary smaller cell-derived RNAs, must become associated with both capsid and polymerase components. Thus interactions between viral proteins themselves, between proteins of viral and cell origin, as well as those between viral proteins, nucleic acids, and lipids are at the heart of the assembly process.

All replication competent retroviruses contain four genes that encode the structural and enzymatic components of the virion. These are gag (capsid protein), pro (aspartyl proteinase), pol (reverse transcriptase and integrase enzymes) and env (envelope glycoprotein). Unlike most other enveloped RNA viruses, in which the viral glycoproteins appear to catalyze virus particle formation, assembly and release of retrovirus particles occurs when capsid proteins are produced in the absence of the other gene products. Several studies have shown that expression of the gag gene alone in a number of systems results in the efficient assembly and release of membrane enveloped virions (Craven, R. C., et al. (1996). Dynamic interactions of the Gag polyprotein. *Current Topics in Microbiology and Immunology* 214, pp. 65–94; Delchambre, M., et al. (1989). The Gag precursors of simian immunodeficiency virus assembles into virus-like particles. *EMBO* 8, pp. 2653–60; Dickson, C., et al. (1984). "Protein biosynthesis and assembly," *RNA tumor viruses* (R. Weiss, N. Teich, H. Varmus, and J. Coffin, Eds.), Vol. 1, pp. 513–648. 2 vols. Cold Spring Harbor Laboratory, Cold Spring Harbor, N.Y.; Gheysen, H. P., et al. (1989), "Assembly and release of HIV-1 precursor Pr55 gag virus-like particles from recombinant baculovirus-infected insect cells," *Cell* 59, pp. 103–12; Haffar, O., et al. (1990), "Human immunodeficiency virus-like, non-replication, Gag-Env particles assemble in a recombinant vaccinia virus expression system," *J. Virol.* 64, pp. 2653–59; Hunter, E. (1994), "Macromolecular interactions in the assembly of HIV and other retroviruses," *Sem. in Virology* 5, pp. 71–83; Krausslich, H.-G., et al. (1996), "Intracellular transport of retroviral capsid components," *Current Topics in Microbiology and Immunology* 214, pp. 25–64; Madisen, L., et al. (1987), "Expression of the human immunodeficiency virus gag gene in insect cells," *Virology* 158, pp. 248–250; Smith, A. J., et al. (1990), "Human immunodeficiency virus type 1 Pr55 gag and Pr160 gag-pol expressed from a simian virus 40 late-replacement vector are efficiently processed and assembled into virus-like particles," *J. Virol.* 64, pp. 2743–50; Sommerfelt, M. A., et al. (1992), "Importance of the p12 protein in Mason-Pfizer monkey virus assembly and infectivity," *J. Virol.* 66, pp. 7005–11; Wills, J. W., et al. (1989), "Creation and expression of myristylated forms of Rous sarcoma virus Gag protein in mammalian cells," *J. Virol.* 63, pp. 4331–43). Thus, the product of this gene has the necessary structural information to mediate intracellular transport, to direct assembly into the capsid shell, and to catalyze the process of membrane extrusion known as budding.

The gag gene product, a polyprotein precursor, is translated on free polyribosomes from an unspliced, genome length mRNA (Eisenman, R. N., et al. (1974), "Synthesis of avian RNA tumor virus structural proteins," *Cold Spring Harbor Symp. Quant. Biol.* 39, pp. 1067–1075). Such precursors will generally follow one of two pathways during the process of viral morphogenesis (Gelderblom, H. (1990), "Morphogenesis, maturation, and fine structure of lentiviruses," *Retroviral Proteases: Control of Maturation and Morphogenesis* (L. H. Pearl, Ed.), pp. 159–80. Stockton Press, New York, N.Y.). In most retroviruses, the nascent Gag polyproteins are transported directly to the plasma membrane where assembly of the immature capsid shell and membrane extrusion occur simultaneously. Viruses that undergo this form of morphogenesis are known as type-C viruses and include the avian and mammalian leukemia/sarcoma viruses (e.g., Rous sarcoma, avian leukosis and murine leukemia virus) (Teich, N. (1982), "Taxonomy of retroviruses," 2nd ed., *RNA tumor viruses* (A. Weiss, N. Teich, H. E. Varmus, and J. M. Coffin, Eds.), pp. 25–207, Cold Spring Harbor Laboratory, New York). The pathogenic human viruses, human T-cell leukemia virus and human immunodeficiency virus (HTLV-I and HIV), assemble their capsids in a similar fashion. In the second morphogenic class of viruses, the Gag precursors appear to be targeted to an intracytoplasmic site where immature capsid assembly occurs (Rhee, S. S., et al. (1990), "A single amino acid substitution within the matrix protein of a type D retrovirus converts its morphogenesis to that of a type C retrovirus," *Cell* 63, pp. 77–86; Rhee, S. S., etal. (1991), "Amino acid substitutions within the matrix protein of type D retroviruses affect assembly, transport and membrane association of a capsid," *EMBO J.* 10, pp. 535–46). These preassembled immature capsids are then transported to the plasma membrane where they undergo budding and envelopment. Viruses that undergo this process of assembly and release include the type-B, mouse mammary tumor virus (MMTV), the type-D, Mason-Pfizer monkey virus (M-PMV) and related simian retroviruses (SRV1–5), as well as members of the spumavirus family (Gelderblom, H. (1990), "Morphogenesis, maturation, and fine structure of lentiviruses," *Retroviral Proteases: Control of Maturation and Morphogenesis* (L. H. Pearl, Ed.), pp. 159–80, Stockton Press, New York, N.Y.; Teich, N. (1982), "Taxonomy of retroviruses," 2nd ed., *RNA tumor viruses* (A. Weiss, N. Teich, H. E. Varmus, and J. M. Coffin, Eds.), pp. 25–207. Cold Spring Harbor Laboratory, New York). Despite the different morphogenic pathways, the process by which Gag precursors assemble into immature capsids is probably similar for the type-C and type-B/D viruses, since a single amino acid change within the gag gene product of M-PMV can divert Gag to the type-C morphogenic pathway (Rhee, S. S., et al. (1990), "A single amino acid substitution within the matrix protein of a type D retrovirus converts its morphogenesis to that of a type C retrovirus," *Cell* 63, pp. 77–86). Irrespective of the pathway to virus release, the newly budded virions have a common immature morphology. In thin-section electron microscopy, the immature capsid shell appears as an electron opaque band in tight apposition to the membrane with an electron lucent center. During the process of virus maturation, the capsid polyprotein precursors are cleaved by the virus-encoded aspartyl proteinase, which leads to collapse of the structure into an electron dense core with a morphology characteristic of the virus family (Gelderblom, H. R. (1991), "Assembly and morphology of HIV: potential effect of structure on viral function," *AIDS* 5, pp. 617–38; Nermut, M. V., et al. (1996), "Comparative morphology and structural classification of retroviruses," *Current Topics in Microbiology and Immunology* 214, pp. 1–24).

The Gag polyprotein precursor functions as the primary building block in virus capsid assembly that is cleaved during maturation by the viral proteinase to yield a number of individual proteins that make up the mature virion. The translation of these products as a precursor protein thus ensures that equimolar amounts of each of the structural proteins are incorporated into the virus. While the size and protein content of the precursor varies between different retroviral families, at least three gag -encoded proteins are found in all retroviruses; these are the matrix protein (MA), the capsid protein (CA), and the nucleocapsid protein (NC) (Leis, J., et al. (1988), "Standardized and simplified nomenclature for proteins common to all retroviruses," *J. Virol.* 62, pp. 1808–9). The matrix protein is closely associated with the viral membrane with which it can be chemically crosslinked (Gebhardt, A., et al. (1984), "Rous sarcoma virus p19 and gp35 can be chemically crosslinked to high molecular weight complexes: An insight into virus assembly," *J. Mol. Biol.* 174, pp. 297–317; Gelderblom, H. R., et al. (1987), "Fine structure of human immunodeficiency virus (HIV) and immunolocalization of structural proteins," *Virology* 156, pp. 171–176; Pepinsky, R. B., et al. (1979), "Identification of retrovirus matrix proteins by lipid-protein crosslinking," *J. Mol. Biol.* 131, pp. 819–837). This amino-terminal domain of the Gag precursor plays a major role in directing the protein to the site of assembly and may be important for the process of membrane extrusion itself, since the MA domain of simian immunodeficiency virus (SIV) expressed in the absence of other Gag domains can direct the budding process (Gonzalez, S. A., et al. (1993), "Assembly of the matrix protein of simian immunodeficiency virus into virus-like particles," *Virology* 194, pp. 548–56). As in most retroviruses, the HIV MA is modified co-translationally by the N-terminal addition of a myristic acid residue that is critical for its function (Bryant, M., et al. (1990), "Myristoylation-dependent replication and assembly of human immunodeficiency virus 1," *Proc. Natl. Acad. Sci. USA* 87, pp. 523–527; Göttlinger, H.G., et al. (1989), "Role of capsid precursor processing and myristoylation in morphogenesis and infectivity of human immunodeficiency virus type I," *Proc. Natl. Acad. Sci. USA* 86, pp. 5781–85). The crystal structure of MA from both HIV and SIV has been determined. Individual MA molecules are composed of 5 major helices capped by a three-stranded P-sheet. The protein assembles into trimers that could create a large, bipartite membrane-binding surface in which exposed basic residues, together with the myristyl moiety, could anchor the protein on the acidic inner side of the viral membrane (Hill, C.P., et al. (1996), "Crystal structures of the trimeric human immunodeficiency virus type 1 matrix protein: implications for membrane association and assembly," *Proc. Natl. Acad. Sci. U.S.A.* 93, pp. 3099–104; Rao, Z., et al. (1995), "Crystal structure of SIV matrix antigen and implications for virus assembly," *Nature* 378, pp. 743–7).

The CA protein forms the major protein component of the electron dense core in mature virions, where it appears to form a protein shell into which the virion RNA genome and replicative enzymes are packed (Bolognesi, D. P., et al. (1973), "Localization of RNA tumor virus polypeptides. I. isolation of further virus substrates," *Virology* 56, pp. 549–64; Gelderblom, H. R. (1991), "Assembly and morphology of HIV: potential effect of structure on viral function," *AIDS* 5, pp. 617–38; Gelderblom, H. R., et al. (1987), "Fine structure of human immunodeficiency virus (HIV) and immunolocalization of structural proteins," *Virology* 156, pp. 171–176). The structure of the N-terminal domain of CA, determined recently by NMR and crystallography, is unlike those of most previously characterized viral coat proteins in that it is predominantly helical—each monomer within the crystallized dimer consists of seven alpha-helices, five of which are arranged in a coil-like structure. The domain is shaped like an arrowhead, with two beta hairpins and a surface-loop exposed at the trailing edge, and the carboxyl-terminal helix projecting from the tip (Gitti, R. K., et al. (1996), "Structure of the amino-terminal core domain of the HIV-1 capsid protein," *Science* 273, pp. 231–5; Momany, C., et al. (1996), "Crystal structure of dimeric HIV-1 capsid protein," *Nat Struct Biol* 3, pp. 763–70). The core protein of the hepatitis B virus is also composed of helices, two of which contribute to an intermolecular 4-helix bundle to form a dimer (Böttcher, B., et al. (1997), "Determination of the fold of the core protein of hepatitis B virus by electron cryomicroscopy," *Nature* 386, pp. 88–91; Conway, J. F., et al. (1997), "Visualization of a 4-helix bundle in the hepatitis B virus capsid by cryo-electron microscopy," *Nature* 386, pp. 91–94).

The NC protein is located within the CA-derived shell where it is found associated with the viral RNA genome (Linial, M. L., et al. (1990), "Retroviral RNA packaging: Sequence requirements and implications," *Curr. Top. Microbiol. and Immunol.* 157, pp. 125–152). This domain of the Gag precursor, in all retroviruses but the spumaviridae, contains a conserved cysteine-histidine rich, zinc finger-like region (Cys-$X_2$-Cys-$X_4$-His-$X_4$-Cys) that is thought to play an important role in the specific packaging of viral RNA into the assembling virus (Berkowitz, R., et al. (1996), "RNA packaging," *Current Topics in Microbiology and Immunology* 214, pp. 177–218; Berkowitz, R. D., et al. (1993), "Specific binding of human immunodeficiency virus type 1 gag polyprotein and nucleocapsid protein to viral RNAs detected by RNA mobility shift assays," *J. Virol.* 67, pp. 7190–7200; Gorelick, R., et al. (1990), "Non-infectious human immunodeficiency virus type 1 mutants deficient in genomic RNA," *J. Virol.* 64, pp. 3207–11; Gorelick, R. J., et al. (1988), "Point mutants of Moloney murine leukemia virus that fail to package viral RNA: Evidence for specific RNA recognition by a "zinc-finger-like" protein sequence," *Proc. Natl. Acad. Sci. USA* 85, pp. 8420–24; Katz, R. A., et al. (1989), "What is the role of the cys-his motif in retroviral nucleocapsid (NC) proteins?", *BioEssays* 11, pp. 176–81; Meric, C., et al. (1989), "Characterization of Moloney murine leukemia virus mutants with single amino acid substitutions in the cys-his box of the nucleocapsid protein," *J. Virol.* 63, pp. 1558–68; Meric, C., et al. (1988), "Mutations in Rous sarcoma virus nucleocapsid protein p12 (NC):

deletions of Cys-His boxes," *J. Virol.* 62, pp. 3328–33; Sakalian, M., et al. (1994), "Efficiency and selectivity of RNA packaging by Rous sarcoma virus Gag deletion mutants," *J. Virol.* 68, pp. 5969–81).

The arrangement of the proteins on the precursor ($NH_2$-MA- CA- NC—COOH) reflects their position in the virion, where they appear to form concentric shells of protein after cleavage from the precursor. This interpretation is supported by immuno-electron microscopy, detergent fractionation studies, and chemical cross-linking analyses (Gelderblom, H. R., et al. (1987), "Fine structure of human immunodeficiency virus (HIV) and immunolocalization of structural proteins," *Virology* 156, pp. 171–176; Pepinsky, R. B., et al. (1980), "Chemical cross-linking of proteins in avian sarcoma and leukemia viruses," *Virology* 102, pp. 205–10; Stromberg, K., et al. (1974), "Structural studies of avian myeloblastosis virus: comparison of polypeptides in virion and core component by dodecyl sulfate-polyacrylamide gel electrophoresis," *J. Virol.* 13, pp. 513–28). Despite a common organization, Gag precursors from different retroviruses share little amino acid sequence homology except for a conserved region of approximately 20 amino acids in CA, termed the major homology region (MHR, Wills, J. W., et al. (1991), "Form, function, and use of retroviral Gag proteins," *AIDS* 5, pp. 639–54), and the conserved cysteine-histidine motifs in the NC domain. Functional homologies must thus be reflected at the level of three-dimensional structure, as has been observed between retroviral proteinases (Weber, I. (1990), "Comparison of the crystal structures and intersubunit interactions of human immunodeficiency and Rous sarcoma virus proteases," *J. Biol. Chem.* 265, pp. 10492–96) and among the MA protein structures of HIV, SIV, BLV (Matthews, S., et al. (1996), "The solution structure of the bovine leukaemia virus matrix protein and similarity with lentiviral matrix proteins," *Embo J* 15, pp. 3267–74), and M-PMV (Conte, M. R., et al. (1997), "The three-dimensional solution structure of the matrix protein from the type D retrovirus, the Mason-Pfizer Monkey virus," submitted), which share little sequence homology but which maintain very similar three-dimensional structures.

Production of a nascent particle with a defined size, density, and morphology requires that Gag proteins 1) find each other, 2) interact in a regular and stable manner to form the spherical, immature capsid, 3) associate with the plasma membrane, and 4) drive the budding process. The amino acid sequences of Gag that are involved in these processes, as well as those which might have other functions in the virus replication cycle, are being ascertained through mutational analyses. This approach, which has been explored in a variety of retroviruses, is reviewed in detail by Craven and Parent (Craven, R. C., et al. (1996), "Dynamic interactions of the Gag polyprotein," *Current Topics in Microbiology and Immunology* 214, pp. 65–94). It is important to keep in mind that the assembly domains within the Gag precursor may not necessarily reside within the boundaries of the mature cleavage products of Gag but may span the cleavage sites. Thus, PR-mediated processing of the Gag precursor destroys these assembly functions and defines the transition from an assembly function of Gag to an entry/infection one where there is a requirement for efficient disassembly and release of a transcriptionally active core upon infection of a new cell.

Evidence for the existence of assembly domains within Gag proteins has been obtained by mutational analysis. Of the different Gag proteins that have been examined with regard to the specific amino acids involved in particle formation, the RSV Gag protein is by far the best defined. This type of analysis has yielded striking results where several assembly domains, comprising less than 30% of the total Gag precursor have been defined and partially characterized.

All Gag proteins appear to require their amino termini for membrane association. In RSV, the amino-terminal assembly domain (M) appears to include the first half of the MA domain, since small deletions in this region destroy capsid assembly, and budding and the precursors fail to localize at the plasma membrane. These results are similar to those from studies with mammalian retroviruses in which myristylation has been blocked. The membrane binding domain of Gag proteins from other retroviruses are also contained in their amino terminal sequences (Bennett, R. P., et al. (1993), "Functional chimeras of the Rous sarcoma virus and human immunodeficiency virus gag proteins," *J. Virol.* 67, pp. 6487–98; Rhee, S. S., et al. (1987), "Myristylation is required for intracellular transport but not for assembly of D-type retrovirus capsids," *J. Virol.* 61, pp. 1045–53; Rhee, S. S., et al. (1991), "Amino acid substitutions within the matrix protein of type D retroviruses affect assembly, transport and membrane association of a capsid," *EMBO J.* 10, pp. 535–46; Spearman, P., et al. (1994), "Identification of human immunodeficiency virus type 1 Gag protein domains essential to membrane binding and particle assembly," *J. Virol.* 68, pp. 3232–42; Yu, X., et al. (1992), "The matrix protein of human immunodeficiency virus type 1 is required for incorporation of viral envelope protein into mature virions," *J. Virol.* 66, pp. 4966–71; Zhou, W., et al. (1994), "Identification of a membrane-binding domain within the amino-terminal region of human immunodeficiency virus type 1 Gag protein which interacts with acidic phospholipids," *J. Virol.* 68, pp. 2556–69). Recent NMR and crystallographic studies of bacterially expressed HIV MA protein (p17) have provided insights into the three dimensional structure of this normally membrane-associated molecule (Conte, M. R., et al. (1997), "The three-dimensional solution structure of the matrix protein from the type D retrovirus, the Mason-Pfizer Monkey virus," submitted; Hill, C. P., et al. (1996), "Crystal structures of the trimeric human immunodeficiency virus type 1 matrix protein: implications for membrane association and assembly," *Proc. Natl. Acad. Sci. U.S.A.* 93, pp. 3099–104; Matthews, S., et al. (1994), "Structural similarity between the p 17 matrix protein of HIV-1 and interferon-Gamma," *Nature* 370, pp. 666–8; Rao, Z., et al. (1995), "Crystal structure of SIV matrix antigen and implications for virus assembly," *Nature* 378, pp. 743–7). Although predominantly helical, a prominent feature of p17MA is an irregular β-sheet, the solvent-exposed side of which provides a surface that could associate with the inner face of the membrane, since several basic side chains (K8, R20, R22, K26–28, K30, K32, K95) are available for inter with phospholipid head groups (Matthews, S., et al. (1994), "Structural similarity between the p17 matrix protein of HIV-1 and interferon-Gamma," *Nature* 370, pp. 666–8). Indeed, mutations which alter the charge distribution in this region have significant effects on virus assembly (Gonzalez, S. A., et al. (1993), "Assembly of the matrix protein of simian immunodeficiency virus into virus-like particles," *Virology* 194, pp. 548–56; Yuan, X., et al. (1993), "Mutations in the N-terminal region of human immunodeficiency virus type 1 matrix protein block intracellular transport of the Gag precursor," *J. Virol.* 67, pp. 6387–94; Zhou, W., et al. (1994), "Identification of a membrane-binding domain within the amino-terminal region of human immunodeficiency virus type 1 Gag protein which interacts with acidic phospholipids," *J. Virol.* 68, pp. 2556–69).

A second assembly domain (L) has been identified for RSV that appears to mediate a late stage in the budding process. This domain includes a PPPY (WW-binding) motif that is physically located within the carboxy-terminus of the "spacer peptide" p2 (Garnier, L., et al. (1996), "WW domains and retrovirus budding," *Nature* 381, pp. 744–745). Mutations within this region appear to block the final stages of budding (Wills, J. W., et al. (1994), "An assembly domain of the Rous sarcoma virus Gag protein required late in budding," *J Virol* 68, pp. 6605–18). A similar motif is found within the pp16 region of M-PMV where mutagenesis studies yielded a similar phenotype (Yasuda, J., et al. (1997), "A proline-rich motif (PPPY) in the Gag polyprotein of Mason-Pfizer monkey virus plays a maturation-independent role in virion release," *J. Virol., Submitted for publication*). In HIV, the carboxy-terminal peptide sequence, p6, appears to play an analogous role. Truncations or deletions of this domain result in the accumulation of immature particles still attached to the plasma membrane by a thin stalk (Göttlinger, H. G., et al. (1991), "Effect of mutations affecting the p6 gag protein on human immunodeficiency virus particle release," *Proc. Natl. Acad. Sci. U.S.A.* 88, pp. 3195–99). Curiously, the L domain may be moved in position within the Gag precursor molecule and still function, and domains from one retrovirus may function in another (Parent, L. J., et al. (1995), "Positionally independent and exchangeable late budding functions of the Rous sarcoma virus and human immunodeficiency virus Gag proteins," *Journal of Virology* 69, pp. 5455–60).

For those Gag proteins that have been examined in detail, there appears to be a specific domain that is essential for the production of particles with the correct density and size. In RSV, this domain (I) spans the carboxy-terminal end of the CA domain and half of the NC domain, and is essential for the production of particles with the correct density (Weldon, R. A., Jr., et al. (1993), "Characterization of a small (25 kDa) derivative if the Rous sarcoma virus Gag protein competent for particle release," *J. Virol.*, In Press). HIV and MuLV Gag proteins also require analogous regions for the production of particles with the correct density (Jones, T. A., et al. (1990), "Assembly of gag -β-galactosidase proteins into retrovirus particles," *J. Virol.* 64, pp. 2229–65; Jowett, J. B. M., et al. (1992), "Distinct signals in human immunodeficiency virus type 1 Pr55 necessary for RNA binding and particle formation," *J. Gen. Virol.* 73, pp. 3079–86). Furthermore, addition of this domain from HIV to a mutant RSV Gag protein that assembles into low-density particles can restore dense particle formation (Bennett, R. P., et al. (1993), "Functional chimeras of the Rous sarcoma virus and human immunodeficiency virus gag proteins," *J. Virol.* 67, pp. 6487–98). Although the mechanism by which this domain influences particle density is not known, it could establish the correct protein-protein interactions that allow the tight packing of Gag molecules during particle formation. Alternatively, since this region contains sequences implicated in RNA packaging, this domain may influence particle density by directly mediating RNA encapsidation (Weldon, R. A., Jr., et al. (1993), "Characterization of a small (25 kDa) derivative if the Rous sarcoma virus Gag protein competent for particle release," *J. Virol.*, In Press). Thus, RNA could serve as a necessary scaffold upon which Gag proteins tightly pack during particle assembly.

Finally, there appears to be a region in Gag that influences particle size. In RSV, this region is located within the p10 and amino-terminal two-thirds of the CA domains. Mutants lacking this region can assemble into particles of the correct density, but these particles are heterogeneous in size (Weldon, R. A., Jr., et al. (1993), "Characterization of a small (25 kDa) derivative if the Rous sarcoma virus Gag protein competent for particle release," *J. Virol.*, In Press). Similarly several mutations in the highly- conserved MHR region of M-PMV yield particles of aberrant size (Strambio-de-Castillia, C., et al. (1992), "Mutational analysis of the major homology region of Mason-Pfizer monkey virus by use of saturation mutagenesis," *J. Virol.* 66, pp. 7021–32). Thus, if Gag proteins fold into rod-like or cone-shaped structures (Nermut, M. V., et al. (1996), "Comparative morphology and structural classification of retroviruses," *Current Topics in Microbiology and Immunology* 214, pp. 1–24; Nermut, M. V., et al. (1994), "Fullerene-like organization of HIV gag -protein shell in virus-like particles produced by recombinant baculovirus," *Virology* 198, pp. 288–96) and interact with one another through amino and carboxy-terminal sequences, then this region may act as a spacer that establishes the curvature of the assembling capsid and thus influences the size (or shape) of the capsid.

Expression of the M-PMV gag gene in bacteria results in the rapid formation of inclusion bodies that, in thin section electron microscopy, contain assembled capsid structures that are indistinguishable from capsids assembled in HeLa cells. These results indicate that in vivo the environment of the bacterial cytoplasm is permissive for capsid assembly. Following purification of the inclusion bodies and solubilization in 8M urea, the soluble Gag precursors can, following removal of the denaturant, assemble in vitro into immature capsid-like structures. Negative-stain electron microscopy following sucrose gradient sedimentation showed large numbers of uniform-sized capsids (Klikova, M., et al. (1995), "Efficient in vivo and in vitro assembly of retroviral capsids from Gag precursor proteins expressed in bacteria," *J. Virol.* 69, pp. 1093–98). Similarly, Campbell and Vogt (Campbell, S., et al. (1995), "Self-assembly in vitro of purified CA-NC proteins from Rous sarcoma virus and human immunodeficiency virus type 1," *J. Virol* 69, pp. 6487–97) expressed a CA-NC fragment of the RSV and HIV Gag precursors in *E. coli*. These proteins were purified in native form and, after adjustment of the pH and salt concentration, each was found to assemble at a low level of efficiency into structures that resembled circular sheets and roughly spherical particles. The presence of RNA dramatically increased the efficiency of assembly, and, in this case, the proteins formed hollow, cylindrical particles whose lengths were determined by the size of the RNA. It is possible that this latter assembly process might mimic the interactions that occur during maturation of the virus particle where the NC and CA proteins condense around the viral genome. More recent experiments by Campbell and Vogt, with more complete portions of the RSV Gag precursor, have demonstrated the assembly of spherical immature-like particles when the protein was combined with RNA under the proper conditions (Campbell, S., et al. (1997), "In vitro assembly of virus-like particles with Rous sarcoma virus gag deletion mutants: Identification of the p10 domain as a morphological determinant in the formation of spherical particles," *Journal of Virology* 71, pp. 4425–4435). This study also identified the p 10 region of Gag as the determinant for spherical particle formation and, thus, is consistent with previous results that indicated this region might act as a spacer to control the size of the assembling capsid.

Essentially all biochemical processes are initiated or maintained through highly specific and selective molecular interactions. Receptor molecules in cell membranes, antibodies, enzymes, and other macromolecules with a polypeptide character are capable of interacting with defined, specific peptide or nonpeptide structures on the basis of their binding sites. If one of the interactive sites is determined by a sequence of the peptide, it is possible to identify this site in a relatively straightforward way through the application of peptide libraries (Blake, J., et al. (1996), "Use of combinatorial peptide libraries to construct functional mimics of tumor epitopes recognized by MHC class I-restricted cytolytic T lymphocytes," *J Exp Med* 184, pp. 121–30; Houghten, R. A. (1993), "The broad utility of soluble peptide libraries for drug discovery," *Gene* 137, pp. 7–11; Houghten, R. A., et al. (1991), "Generation and use of synthetic peptide combinatorial libraries for basic research and drug discovery," *Nature* 354, pp. 84–6; Lam, K. S., et al. (1991), "A new type of synthetic peptide library for identifying ligand-binding activity" [published errata appear in Nature 1992 Jul. 30; 358(6385): 434 and 1992 Dec. 24–31; 360(6406): 768], *Nature* 354, pp. 82–4; Scott, J. K., et al. (1994), "Random peptide libraries," *Curr Opin Biotechnol* 5, pp. 40–8). As Houghten (Houghten, R. A. (1994), "Combinatorial libraries. Finding the needle in the haystack," *Curr Biol* 4, pp. 564–7) has pointed out, the construction of libraries consisting of millions of compounds provides a fundamental, practical advance in the study of the molecular interactions of pharmacologically relevant biochemical targets. Such libraries have been utilized in the study of antibody-antigen interactions, in the development of enzyme inhibitors and novel anti-microbial drugs, in the identification of biologically active peptides, and in the engineering of novel properties into antibodies. The use of peptide library technologies, followed by synthetic methodologies directed towards optimization, is a key route to obtaining peptides of desirable binding and stability properties. It facilitates the identification of small molecules that bind with high affinity to acceptor molecules and so mimic or block their interactions with the natural ligands.

The principle of libraries enables one to find, in a rapid, effective way, those particular molecules or structures that influence a particular biological system by testing a very large collection ($10^6$–$10^9$) of chemical structures simultaneously. Library-based methods that have been used so far fall into three broad categories, differing in the way in which the compounds making up the library have been synthesized and/or presented (Houghten, R. A. (1994), "Combinatorial libraries. Finding the needle in the haystack," *Curr Biol* 4, pp. 564–7). The first category includes so-called fusion-protein-displayed peptide libraries, in which random peptides or proteins are expressed on the surface of filamentous phage particles, or on proteins expressed from plasmids (Scott, J. K., et al. (1994), "Random peptide libraries," *Curr Opin Biotechnol* 5, pp. 40–8; Smith, G. P., et al. (1993), "Libraries of peptides and proteins displayed on filamentous phage," *Methods Enzymol* 217, pp. 228–57). This approach centers on the expression of a number of copies (from a few to thousands) of the same peptide sequence on the surface of the phage. A library is produced by preparing millions of oligonucleotides and inserting these random sequences into the gene encoding the phage coat protein. Those peptide-expressing phage particles that bind to the purified and immobilized target of interest can be enriched in a selection process referred to as "biopanning". After selection, the specific peptide sequence associated with the selected phage is determined by sequencing. The advantage of the above approach is that it involves widely available molecular biological techniques and can generate longer peptide or protein sequences than can be easily produced by chemical syntheses. The disadvantage is the restriction of peptide sequences to those containing the 20 genetically encoded amino acids as the building blocks of the library.

This fusion protein approach has also been adapted into the two-hybrid system for the identification of protein-protein interaction partners. This method originally developed by Fields and coworkers (Fields, S., et al. (1989), "A novel genetic system to detect protein-protein interactions," *Nature* 340, pp. 245–6; Fields, S., et al. (1994), "The two-hybrid system: an assay for protein-protein interactions," *Trends Genet* 10, pp. 286–92) is a yeast-based genetic assay to detect protein-protein interactions in vivo. The two-hybrid method is based on the restoration of transcriptional activation by the GAL4 protein. The GAL4 protein has two functions that are independent and physically separable in the linear sequence of the protein. One function is the specific binding of the protein to upstream activation sequences and the other is transcriptional activation; transcriptional activation of genes under GAL4 control requires that the GAL4 domains exhibiting these two functions be brought into spatial proximity. In the two-hybrid system, a strain of *Saccharomyces cerivisiae* with an integrated copy of the GAL1-lacZ fusion gene provides readout of GAL4 activity. This host is transformed with two plasmids encoding GAL4 fusion proteins: one plasmid encodes a fusion protein of the GAL4 DNA-binding domain and protein X, while the other encodes a fusion protein of the GAL4 activating domain and protein Y. If proteins X and Y interact, the GAL4 activation and DNA-binding regions are brought together, activating expression from the GAL1-lacZ fusion gene. Functional fusion proteins can be produced regardless of whether candidate domains are fused to the N or C terminus of the GAL4 fragment (Chien, C. T., et al. (1991), "The two-hybrid system: a method to identify and clone genes for proteins that interact with a protein of interest," *Proc Natl Acad Sci USA* 88, pp. 9578–82).

The above "forward" system for the selection of interactions has now been re-engineered into a "reverse" system for selection against protein-protein interactions (White, M. A. (1996), "The yeast two-hybrid system: Forward and reverse," *Proceedings of the National Academy of Sciences USA* 93, pp. 10001–3). A counter-selectable yeast strain carrying the URA3 gene behind a modified form of the SPO13 promoter containing GAL4 binding sites was constructed. Activation of URA3 expression by the interaction of proteins X and Y leads to the production of a toxic compound when this strain is grown in the presence of 5-fluoroorotic acid (FOA). Only cells expressing interaction-defective forms of X or Y would display the FOA-resistant phenotype (. This system was used to examine the subunit interactions of the retinoblastoma gene (pRB) product-associated transcription factor E2F/DP. Mutagenesis of E2F and analysis with DP in this system identified a previously uncharacterized interaction domain within E2F1 (Vidal, M., et al. (1996a), "Reverse two-hybrid and one-hybrid systems to detect dissociation of protein-protein and DNA-protein interactions," *Proceedings of the National Academy of Sciences USA* 93, pp. 10315–20; Vidal, M., et al. (1996b), "Genetic characterization of a mammalian protein-protein interaction domain by using a yeast reverse two-hybrid system," *Proceedings of the National Academy of Sciences USA* 93, pp. 10321–26).

In the second library-based category, diverse peptides have been generated and attached to solid supports by synthetic chemistry. Using the "one bead one-peptide" (Lam, K. S., et al. (1991), "A new type of synthetic peptide library for identifying ligand-binding activity" [published errata appear in Nature 1992 Jul. 30;358(6385): 434 and 1992 Dec. 24–31 ;360(6406): 768], Nature 354, pp. 82–4; Lebl, M., et al. (1995), "One-bead-one-structure combinatorial libraries," *Biopolymers* 37, pp. 177–98; Salmon, S. E., et al (1994), "One bead, one chemical compound: use of the selectide process for anticancer drug discovery," *Acta Oncol* 33, pp. 27–31) approach, a library containing one to many million individual peptides is generated on resin beads that are permeable to water-soluble target molecules. For example, all possible sequences of a pentapeptide from the twenty natural amino acids would yield 3.2 million different potential ligands. These libraries are prepared on small beads of a solid phase support with application of a split-synthesis method in such a way that each bead contains molecules of a peptide of only one sequence. A prepared library has a statistical distribution of peptide sequences such that all possible peptides are present in approximately the same quantities. A target molecule bound to a specific peptide that is attached to a single bead can be visualized by standard colorimetric methods that differentiate the bound bead from other beads in the library. These visually tagged beads can be removed with microforceps and the sequence of the attached peptides determined using Edman microsequencing. This approach has the potential to yield expanded libraries through the use of non-native amino acids, cyclic peptides, and other polymeric components (Nikolaiev, V., et al. (1993), "Peptide-encoding for structure determination of nonsequenceable polymers within libraries synthesized and tested on solid-phase supports," *Pept Res* 6, pp. 161–70).

The third category includes procedures in which mixtures of compounds are prepared and designated for direct testing in solution, i.e., they are not bound to any solid surface when being tested. These libraries are prepared in approximately the same way as libraries bound to solid phase supports (Houghten, R. A. (1993), "The broad utility of soluble peptide libraries for drug discovery," *Gene* 137, pp. 7–11). Subsequently, libraries are split off from the solid-phase support and further used as mixtures in aqueous solutions. An advantage of this group of libraries is the possibility of testing in solution using standard pharmacological procedures, and also the possibility of using arbitrary building elements. A disadvantage is the time-consuming iterative procedure of searching for active sequences. Interestingly, a modification of the one-bead/one-peptide approach has been developed in which peptides can be released from the bead-combining the advantages of both soluble and solid phase peptide libraries. In this system, each bead within a library of beads has one peptide sequence, but peptide molecules are attached to the bead with three types of chemical linkers, including two linkers cleavable at different pH optima. An uncleavable linker keeps some peptides attached to the bead for sequencing positives from the solution assay (Salmon, S. E., et al. (1993), "Discovery of biologically active peptides in random libraries: solution-phase testing after staged orthogonal release from resin beads," *Proc Natl Acad Sci USA* 90, pp. 11708–12).

BRIEF SUMMARY OF THE INVENTION

The subject invention provides novel and advantageous methods for identifying amino acid sequences in random peptide libraries that can bind to Gag polypeptides. The subject invention also establishes a novel in vitro system that can be used to test competitive inhibitors of retroviral capsid assembly. Also provided are peptides and compositions containing these peptides, which are inhibitors of the HIV capsid assembly process. Chimeric Gag polypeptides are also provided.

One embodiment of the invention is an isolated chimeric Gag polypeptide comprising: (a) at least a portion of the Mason-Pfizer Monkey Virus (M-PMV) p12 domain comprising residues 1–25 of said M-PMV p12 domain; and (b) at least a portion of an other retroviral Gag polypeptide comprising a functional CA domain, wherein the p12 domain, or the portion of the p12 domain, has an N terminus adjacent to the retroviral Gag polypeptide, and wherein the p12 domain, or the portion of the p12 domain, induces the spontaneous assembly of the chimeric Gag polypeptide into viral capsids within mammalian cells in vitro or under extra cellular in vitro conditions, in the absence of a capsid assembly inhibitor.

Another embodiment of the invention is a composition comprising a carrier and a chimeric Gag polypeptide, wherein said chimeric Gag polypeptide comprises: (a) at least a portion of the Mason-Pfizer Monkey Virus (M-PMV) p12 domain comprising residues 1–25 of said M-PMV p12 domain, and (b) at least a portion of another retroviral Gag polypeptide comprising a functional CA domain, wherein the p12 domain, or the portion of the p12 domain, has an N terminus adjacent to the retroviral Gag polypeptide, and wherein the p12 domain, or the portion of said p12 domain, induces the spontaneous assembly of the chimeric Gag polypeptide into viral capsids within mammalian cells in vitro or under extra cellular in vitro conditions, in the absence of a capsid assembly inhibitor.

Another embodiment of the invention is a viral capsid comprising assembled chimeric Gag polypeptides: wherein the chimeric Gag polypeptides comprise: (a) at least a portion of the Mason-Pfizer Monkey Virus (M-PMV) p12 domain comprising residues 1–25 of the M-PMV p12 domain, and (b) at least a portion of another retroviral Gag polypeptide comprising a functional CA domain, wherein the p12 domain, or the portion of the p12 domain, has an N terminus adjacent to the retroviral Gag polypeptide, and wherein the p12 domain, or the portion of the p12 domain, induces the spontaneous assembly of the chimeric Gag polypeptides into the viral capsid within mammalian cells in vitro or under extra cellular in vitro conditions in the absence of a capsid assembly inhibitor.

BRIEF DESCRIPTION OF THE DRAWINGS

FIGS. 2A–C—In vitro transcription and translation reactions using plasmids containing M-PMV (FIG. 2A), Chimera 3a (FIG. 2B), and HIV (FIG. 2C) gag genes. Assembled products were analyzed by sucrose density gradient fractionation and SDS-PAGE.

FIGS. 3A–E—In vitro transcription and translation reactions using plasmids containing M-PMV, HIV, and Chimera 3a gag genes. After 30 minutes of incubation, cyclohexamide (left panels, FIGS. 3A, 3C, and 3E) or cyclohexamide plus bis-ANS (right panels, FIGS. 3B, 3D, and 3F) were added to the reactions. The reactions were then allowed to continue for an additional 90 minutes. Assembled products were analyzed by sucrose density gradient fractionation and SDS-PAGE. Like M-PMV, but in contrast to HIV, the formation of sedimented material indicative of particle formation by Chimera 3a has been inhibited by the addition of bis-ANS.

FIGS. 4A–D—In vitro transcription and translation reactions using plasmids containing M-PMV and Chimera 4 gag genes. After 30 minutes of incubation, cyclohexamide (left panels, FIGS. 4A and 4C) or cyclohexamide plus bis-ANS (right panels, FIGS. 4B and 4D) were added to the reactions. The reactions were then allowed to continue for an additional 90 minutes. Assembled products were analyzed by sucrose density gradient fractionation and SDS-PAGE. Like M-PMV, the formation of sedimented material by Chimera 4 has been inhibited by the addition of bis-ANS. Lanes L and P indicate the loading material and re-suspended pellet, respectively.

FIG. 7A: Interaction of Gag with itself in the context of both the DNA Binding Domain fusion (BD) and the Transcriptional Activation Domain (AD) promotes growth, as does the positive control. The presence of Gag in either the BD vector or the AD vector alone fails to yield growth. Right Panel.

Figures 9A, 9B, 9C, 9D:
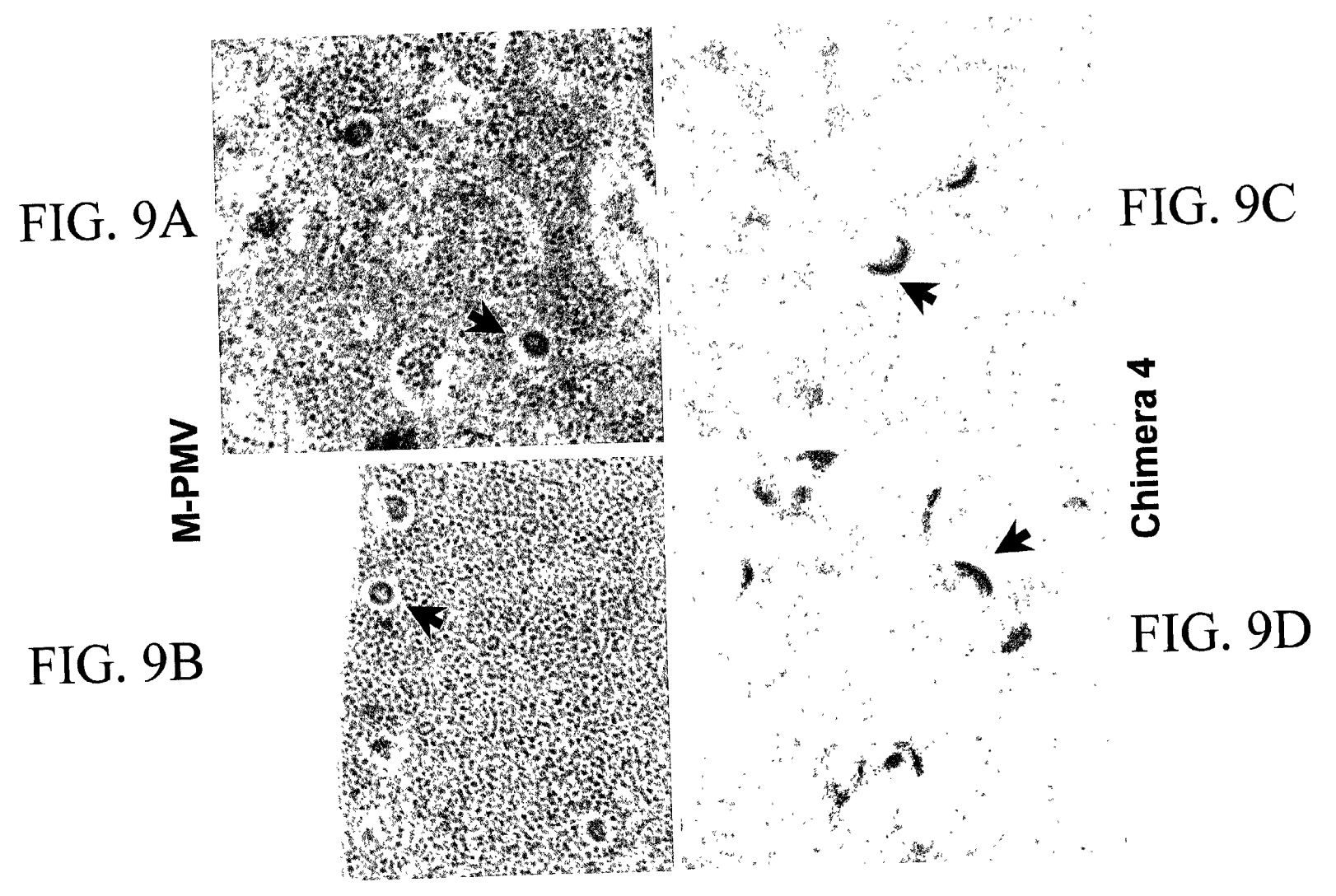

FIGS. 9A–D: Comparative Thin Section EM Analysis of M-PMV and Chimera 4 Gags Assembled In Vitro: Assembly reactions for Chimera 4 and M-PMV Gag were centrifuged at high speed and the resulting pellets were processed for thin section electron microscopy. Compared to M-PMV, which produces apparently completed spherical capsid structures (FIGS. 9A–B), Chimera 4 assembles into structures that appear as crescents (FIGS. 9C–D) with a morphology identical to that seen for wild type (wt) HIV Gag assembling under the plasma membrane of infected cells. Note the darkly staining concentric line (Ch4) or ring (M-PMV) indicative of immature retrovirus capsid morphology.

DETAILED DISCLOSURE OF THE INVENTION

Figure 1A:
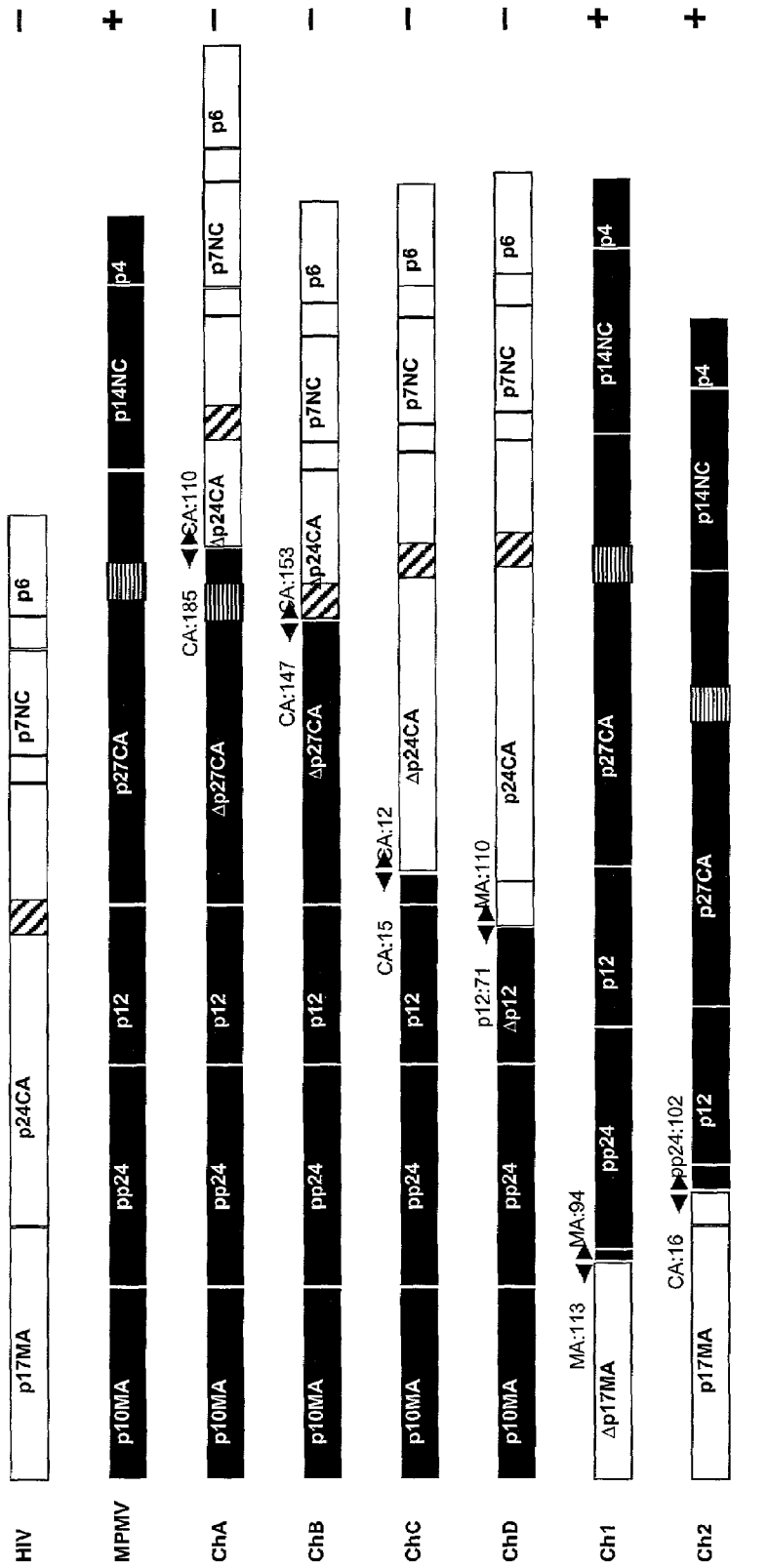
FIGS. 1A and 1B—Chimeric Gag constructs tested and analyzed in the in vitro synthesis and assembly systems. Assembly competence is indicated by plus/minus signs.
Figure 1B:
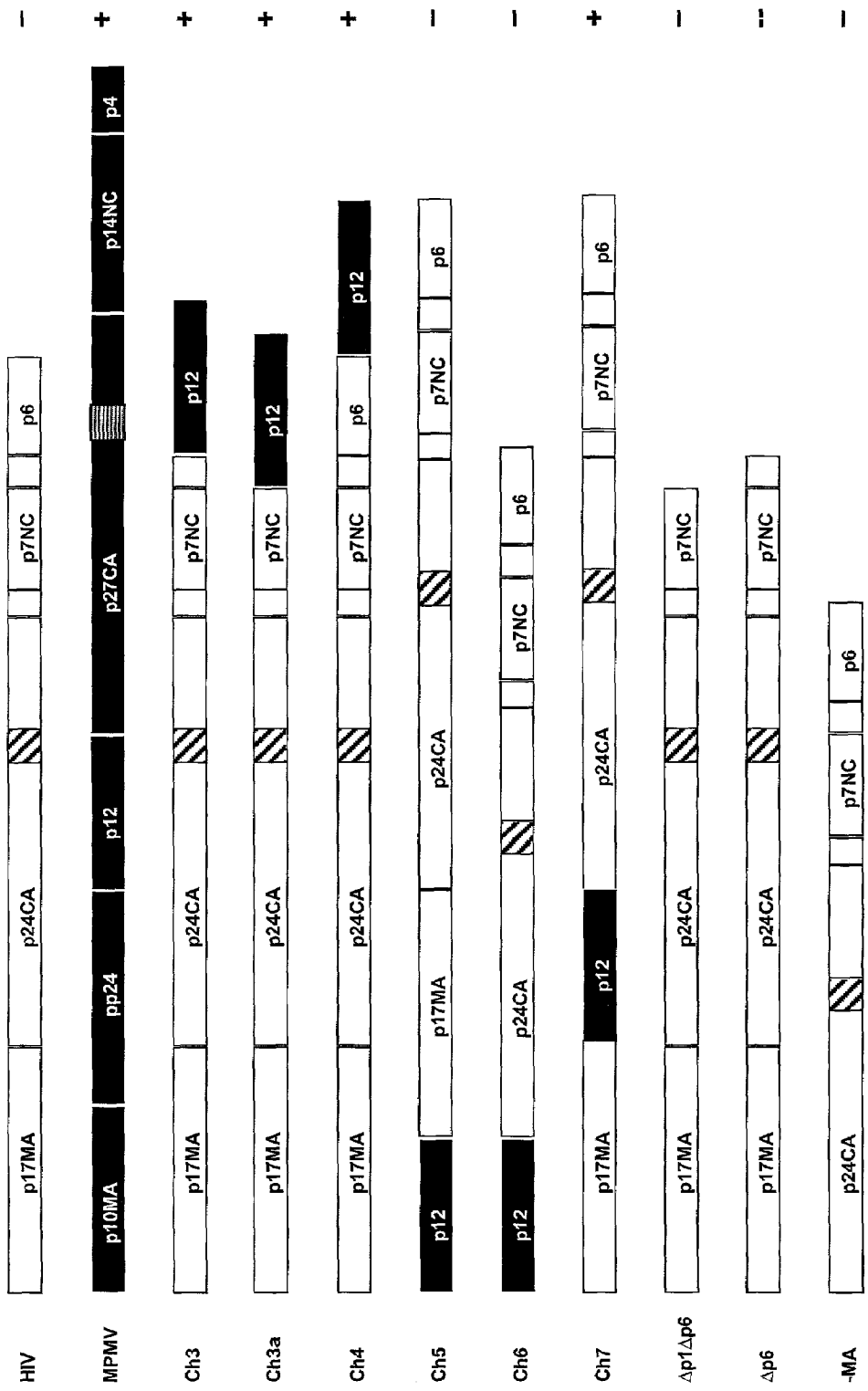
Figure 5:
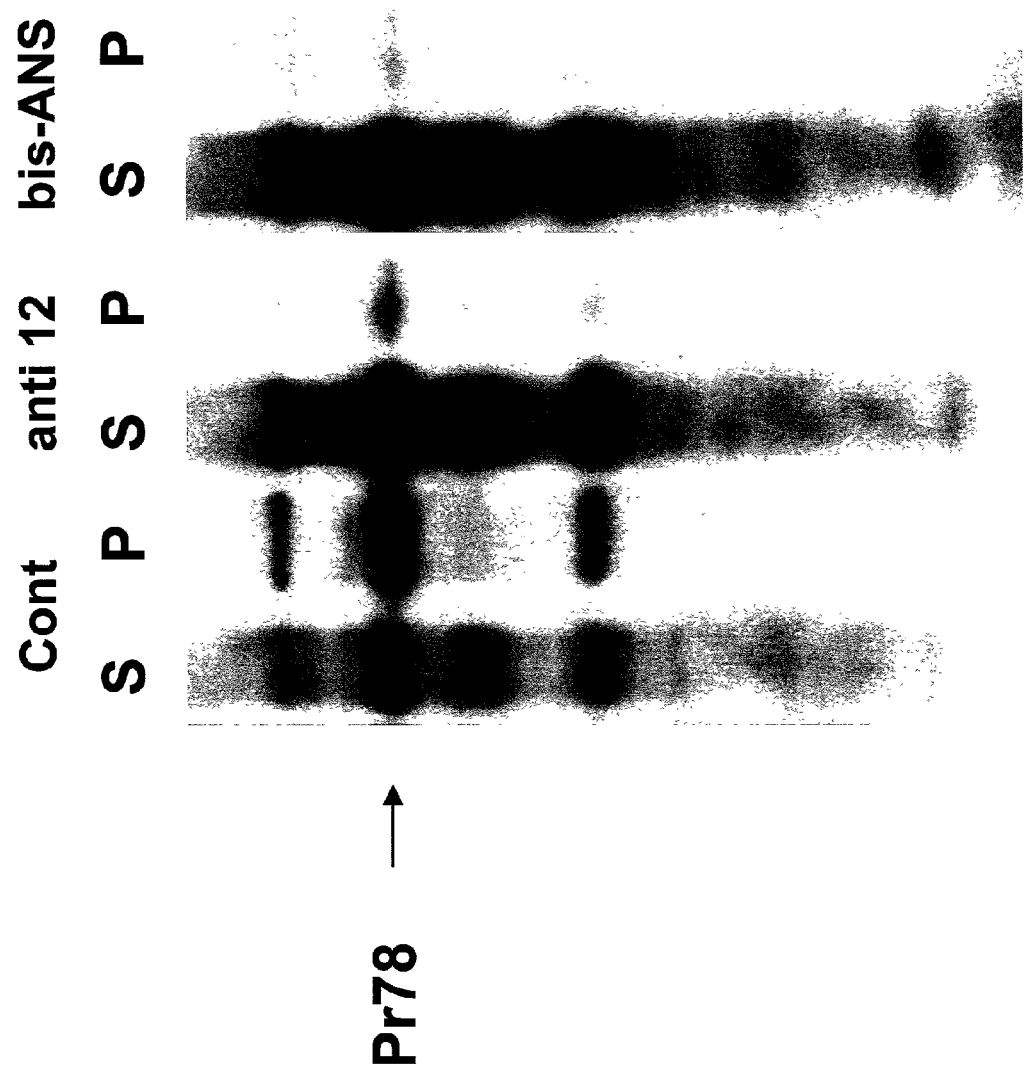
FIG. 5—In vitro transcription and translation reactions using plasmids containing M-PMV gag genes. After 30 minutes of incubation, anti-p 12 antibody or bis-ANS was added to the reactions. The reactions were then allowed to continue for an additional 90 minutes. Assembled products were analyzed by pelleting through a sucrose cushion (35% w/v). Synthesis reactions were pelleted through a sucrose cushion, and supernatant and pellet were then collected for gel analysis. As evidenced by comparison to the control lanes (Cont), both the anti-p12 antibody (anti 12) and bis-ANS were able to reduce or prevent the formation of pelletable material by M-PMV Gag. Lanes S and P indicate supernatant and pellet, respectively.

The subject invention provides novel and advantageous assays for screening of retrovirus capsid assembly inhibitors. Accordingly, a simple and rapid, in vitro assembly assay for chimeric Gag polypeptides provides for the screening of capsid assembly inhibitors. The subject invention provides chimeric Gag polypeptides, which contain Betaretrovirus Gag sequences, for use in the screening assays. Betaretrovirus Gag sequences maybe obtained from mouse mammary tumor virus, Mason-Pfizer monkey virus, simian retrovirus 1, simian retrovirus 2, squirrel monkey retrovirus, langur virus, Jaagsiekte sheep retrovirus, or ovine pulmonary adenocarcinoma virus (Hunter, E.; et al. (1999),. "Retroviridae," *Virus Taxonomy. Seventh Report of the International Committee on Taxonomy of Viruses*, pp. 369–387; Eds. van Regenmortel, M. H. V.; Fauquet, C. M.; Bishop, D. H. L.; Carstens, E.; Estes, M. K.; Lemon, S.; Maniloff, J. Mayo, M. A.; McGeoch, D.; Pringle, C. R.; and Wickner, R. B. London, San Diego: Academic Press).

In one embodiment of the screening assays, chimeric gag constructs are transcribed/translated in commercially available reticulocyte lysate systems and assayed for spontaneous assembly into capsid structures in the presence of peptide inhibitors. In another embodiment, the peptide inhibitors are expressed in a combinatorial library. In a preferred embodiment, the peptides are part of a synthetic peptide (combinatorial) library attached to beads. Libraries expressing peptide inhibitors of the invention may contain linkers that facilitate cleavage of the peptide inhibitors by a change of pH or by proteases. In another embodiment, the peptides are expressed on phage libraries. Peptides identified by one or more of the above screens to interact with Gag proteins, or fragments thereof (such as CA-NC or CA), will by secondarily screened for the ability to inhibit chimeric Gag assembly in the in vitro translation/assembly assay. Combinatorial peptide libraries for screening in the assay systems of the invention may be obtained from a variety of commercial sources.

The subject invention also provides for the identification of peptide-based inhibitors of Gag precursor association using a yeast two-hybrid system and random peptide expression libraries. Combinatorial libraries are used to identify peptides that interact with and inhibit the self-association of Gag and the chimeric Gag proteins of the invention. The inhibitory peptides may be further assayed for their ability to block the self-association of Gag proteins in the in vitro translation/assembly system. Tissue culture virus spread assays may also be utilized to determine the effect of the inhibitory peptides upon virus replication. Inhibitory peptides of the invention are at least about 5 amino acids in length. In one embodiment, the peptides are about 15 amino acids in length.

Another embodiment of the screening assay involves exposing chimeric Gag polypeptides of the invention to random peptide libraries and assessing the ability of the chimeric Gag polypeptides to assemble in vitro. In those instances where in vitro assembly is not observed, the peptide will be isolated, sequenced and further assayed for the ability to block assembly in other assay systems described herein. Tissue culture virus spread assays may also be utilized to determine the effect of the inhibitory peptides upon virus replication.

Also provided by the subject invention are compositions containing the novel peptides identified by the methods provided herein. These compositions may contain one or more of the novel peptides that modulate Gag function, such as Gag assembly and/or the ability to cause the formation of non-infectious viral particles, and a pharmaceutically acceptable excipient. These compositions may further contain other therapeutically effective agents such as AZT, monoclonal antibodies that bind to the Gag protein, interleukins, cytokines, or other inhibitors of retroviral replication. The compounds of the subject invention can be formulated according to known methods for preparing pharmaceutically useful compositions. Formulations are described in detail in a number of sources that are well known and readily available to those skilled in the art. For example, *Remington's Pharmaceutical Science* by E. W. Martin describes formulations that can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions may comprise, as an active ingredient, an effective amount of one or more of the compounds and one or more non-toxic, pharmaceutically-acceptable carrier or diluent. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories, and dispersible granules. A solid carrier can be one or more substances that may act as diluents, flavoring agents, solubilizers, lubricants, suspending agents, binders, preservatives, tablet disintegrating agents, or an encapsulating material.

The disclosed pharmaceutical compositions may be subdivided into unit doses containing appropriate quantities of the active component. The unit dosage form can be a packaged preparation, such as packeted tablets, capsules, or powders in paper or plastic containers or in vials or ampules. Also, the unit dosage can be a liquid-based preparation or formulated to be incorporated into solid food products, a chewing gum, or a lozenge.

Novel and advantageous chimeric Gag proteins, which contain M-PMV Gag sequences, are also provided by this invention. The chimeric Gag proteins of this invention contain, at least, a portion of the p12 domain of the M-PMV Gag protein fused to another Gag protein, or portion thereof. For the purposes of this invention, a "portion" of the M-PMV p12 domain is defined as that minimal part of the p12 polypeptide domain that facilitates the spontaneous assembly of Gag within HeLa cells or in vitro synthesis systems, such as reticulocyte lysates. These are conditions under which C-type Gag precursor proteins, for example HIV Gag, cannot assemble and are expression levels that generally mimic those observed during infection.

Gag proteins suitable for use in the construction of the chimeric proteins of this invention (i.e., fusion to at least a portion of the p12 domain of M-PMV or equivalent domain from another Betaretrovirus) may be selected from any of the viruses within the family Retroviridae which, at present, is comprised of the following retroviral genuses: Alpharetrovirus, Betaretrovirus, Gammaretrovirus, Deltaretrovirus, Epsilonretrovirus, Lentivirus, and Spumavirus (Hunter, E., et al. (1999), "Retroviridae," *Virus Taxonomy. Seventh Report of the International Committee on Taxonomy of Viruses*, pp. 369–87. Eds. van Regenmortel, M. H. V., Fauquet, C. M., Bishop, D. H. L., Carstens, E., Estes, M. K., Lemon, S., Maniloff, J. Mayo, M. A., McGeoch, D., Pringle, C. R., and Wickner, R. B. London, San Diego: Academic Press, 1104 pp). Specific retroviruses may be selected from the following examples: Rous sarcoma virus (RSV), Avian myeloblastosis virus (AMV), Avian erythroblastosis virus (AEV), Rous-associated virus (RAV)-1 to 50, RAV-0, Moloney murine leukemia virus (Mo-MLV), Harvey murine sarcoma virus (HA-MSV), Abelson murine leukemia virus (A-MuLV), AKR-MuLV, Feline leukemia virus (FeLV), Simian sarcoma virus, endogenous and exogenous viruses in mammals, Reticuloendotheliosis virus (REV), spleen necrosis virus (SNV), Mouse mammary tumor virus (MMTV), "SAIDS" viruses, Human T-cell leukemia (or lymphotropic) virus (HTLV), Bovine leukemia virus (BLV), Human immunodeficiency virus (HIV-1 and -2), Simian immunodeficiency virus (SIV), Feline immunodeficiency virus (FIV), SSV, REM, Visna/Maedi virus, Equine infectious anemia virus (EIAV), Caprine arthritis-encephalitis virus (CAEV), Progressive pneumonia virus, many human and primate isolates e.g., simian foamy virus (SFV). Chimeric constructions containing one or more of these Gag proteins are also provided.

Also, as described herein, fragments of the chimeric Gag proteins or inhibitory peptides are an aspect of the subject invention so long as such fragments retain substantially the same biological activity as full-length chimeric Gag protein or the inhibitory peptides of the invention. Such fragments can easily and routinely be produced by techniques well known in the art. For example, time-controlled Bal31 exonuclease digestion of the full-length DNA followed by expression of the resulting fragments and routine screening methods can be used to readily identify expression products having the desired activity. Additional information regarding Gag function may be found in Retroviruses (Coffin, J. M., Hughes, S. H., and Varmus, H. E., eds., [1997] Cold Spring Harbor Laboratory Press, Cold Spring Harbor, N.Y.).

The subject invention also provides polynucleotide sequences that encode the chimeric Gag proteins of this invention; polynucleotide sequences that encode the peptide inhibitors of the instant invention are also provided. Genetic constructs, vectors, expression cassettes, and transformed host cells comprising polynucleotide sequences encoding the chimeric Gag protein or peptides of the invention are likewise provided. These vectors include, for example, cloning vectors, expression vectors, and the like. Numerous vectors that can be used according to the present invention are known in the art. Genetic constructs, vectors, and expression cassettes according to this invention may also contain linker sequences, polylinker sequences, control elements, and/or regulatory sequences.

Also within the scope of the invention are polynucleotides complementary to those polynucleotides encoding the chimeric Gag polypeptides of the invention or the inhibitory peptides of the invention. Polynucleotides that hybridize with polynucleotides encoding the chimeric Gag polypeptides of the invention or the inhibitory peptides of the invention are also provided. Preferably, hybridizing polynucleotide sequences hybridize under stringent conditions.

As those of ordinary skill in the art will appreciate, any of a number of different nucleotide sequences can be used, based on the degeneracy of the genetic code, to produce the chimeric Gag proteins or inhibitory peptides described herein. Accordingly, any polynucleotide sequence which encodes the chimeric Gag proteins or inhibitory peptides described herein comes within the scope of this invention.

Also contemplated by the present invention are transformed host cells (microorganisms, viruses, and the like) that contain the polynucleotides and/or polypeptides of the invention. The cells can be either eukaryotic or prokaryotic cells. Prokaryotic cells include, for example, *E. coli, Bacillus* species, and others. Eukaryotic cells include, for example, yeast cells, insect cells, plant cells, and mammalian cells. Microorganisms and cells comprising polynucleotides of the invention can be used to express sufficient quantities of the chimeric Gag protein or peptides of the invention for purification purposes or industrial purposes.

Thus, the subject invention also provides methods reducing or inhibiting the formation of viral capsids in an individual by administration of pharmaceutical compositions containing one or more of the inhibitory peptides of the invention. The invention also provides methods of treating retroviral infections comprising the administration of inhibitory peptide compositions of the instant invention.

The subject invention also concerns isolated polyclonal and monoclonal antibodies that bind to inhibitory peptides of the invention and anti-idiotypic antibodies that mimic the inhibitory peptides of the instant invention. Antibodies that are immunospecific for peptides of the invention are specifically contemplated and the antibodies maybe naturally occurring or derivatized. Further, the antibodies and anti-idiotypic antibodies of the subject invention can be prepared using standard materials and methods known in the art (see, for example, *Monoclonal Antibodies: Principles and Practice,* 1983; *Monoclonal Hybridoma Antibodies: Techniques and Applications,* 1982; *Selected Methods in Cellular Immunology,* 1980; *Immunological Methods, Vol. II,* 1981; *Practical Immunology*; and Kohler et al. [1975] *Nature* 256:495).

The term "antibody" is used in the broadest sense and specifically covers monoclonal antibodies (including full-length monoclonal antibodies), polyclonal antibodies, multispecific antibodies (e.g., bispecific antibodies), and antibody fragments, so long as they exhibit the desired biological activity, particularly neutralizing activity. "Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody," as used herein, refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. [1975] *Nature* 256:495, or may be made by recombinant DNA methods (see, e.g., U.S. Pat. No.4,816,567). The "monoclonal antibodies" may also be isolated from phage antibody libraries using the techniques described in Clackson et al. [1991] *Nature* 352:624–628 and Marks et al. [1991] *J. Mol. Biol.* 222:581–597, for example.

The monoclonal antibodies, as used herein, specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No.4,816,567; and Morrison etal. [1984] Proc. Natl. Acad. Sci. USA 81:6851–6855).

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the VH and VL domains that enables the sFv to form the desired structure for antigen binding. For a review of sFv, see Pluckthun in *The Pharmacology of Monoclonal Antibodies* [1994] Vol. 113:269–315, Rosenburg and Moore, eds. Springer-Verlag, New York.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells, since at least one component of the antibody's natural environment will not be present. Ordinarily, however, isolated antibody will be prepared by at least one purification step.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally occurring nucleotides. The polynucleotide sequences include both the DNA strand sequence that is transcribed into RNA and the RNA sequence that is translated into protein. The polynucleotide sequences include both full-length sequences, as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention. The polynucleotide sequences falling within the scope of the subject invention further include sequences that specifically hybridize with the exemplified sequences. The polynucleotide includes both the sense and anti-sense strands as either individual strands or in the duplex. The invention also provides polynucleotides that are complementary to the disclosed polynucleotide sequences.

"Linkers" are synthesized palindromic nucleotide sequences that create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, KpnI, and Hind III, or which provide a blunt end such as EcoRV, SnaBI, and StuI.

"Control elements" or "regulatory sequences" are those nontranslated regions of the gene, or DNA such as enhancers, promoters, introns, and 3' untranslated regions that interact with cellular proteins to carry out replication, transcription, and translation. They may occur as boundary sequences or even split the gene. They function at the molecular level and along with regulatory genes are very important in development, growth, differentiation, and aging processes.

"Chimeric" molecules are polynucleotides or polypeptides that are created by combining one or more of nucleotide sequences with additional nucleic acid sequence(s). In the context of this invention, one embodiment of a "chimeric" molecule is a combination of a retroviral gag encoding nucleic acid, with at least a portion of the p12 domain of M-PMV or equivalent domain from another member of the genus Betaretrovirus. Other embodiments of the invention include a chimeric gag polynucleotide as described above with additional elements attached. Such elements include polyhistidine residues or AVITAGs. Chimeric polynucleotide sequences may be introduced into an appropriate vector and expressed to give rise to a chimeric polypeptide that may be expected to be different from the native molecule in one or more of the following characteristics: capsid assembly, cellular location, distribution, ligand-binding affinities, interchain affinities, degradation/turnover rate, signaling, etc.

"Naturally occurring" refers to a polypeptide produced by cells which have not been genetically engineered or which have been genetically engineered to produce the same sequence as that naturally produced. Specifically contemplated are various polypeptides that arise from post-transnational modifications. Such modifications of the polypeptide include, but are not limited to, acetylation, carboxylation, glycosylation, phosphorylation, sulfation, lipidation, ubiquitination, and acylation.

"Derivative", "derivatives", and "derivatized" refer to those polypeptides that have been chemically modified by such techniques as labeling, pegylation (derivatization with polyethylene glycol), and chemical insertion or substitution of amino acids, such as ornithine, which do not normally occur in proteins. "Derivative" peptides of the invention may be chemically modified to increase the stability of the peptide, when administered in vivo, according to methods well known in the art (see, for example, Veronese, F. M., et al. [1999] 54(8): 497–516).

As used herein, the term "polypeptide" refers to a polymer of amino acids and does not refer to a specific-length of the product; thus, peptides, oligopeptides, and proteins are included within the definition of polypeptide. This term also does not refer to or exclude post-expression modifications of the polypeptide, for example, glycosylations, acetylations, phosphorylations, and the like. Included within the definition are, for instance, polypeptides containing one or more analogs of an amino acid (e.g., unnatural amino acids, etc.), polypeptides with substituted linkages, as well as other modifications known in the art, both naturally occurring and non-naturally occurring. The term "domain" or "polypeptide domain" refers to that sequence of a polypeptide that folds into a single globular region in its native conformation, or that may exhibit discrete binding or functional properties.

"Recombinant polypeptide variant" refers to any polypeptide that differs from a naturally occurring peptide, polypeptide, or protein by amino acid insertions, deletions, and/or substitutions created using recombinant DNA techniques. Guidance in determining which amino acid residues may be replaced, added, or deleted without abolishing characteristics of interest may be found by comparing the sequence of the peptide, polypeptide, or protein with that of related polypeptides and minimizing the number of amino acid sequence changes made in highly-conserved regions.

Amino acid "substitutions" are defined as one-for-one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the sequence using recombinant DNA techniques.

A "signal or leader sequence" is a short amino acid sequence that can be used, when desired, to direct the polypeptide through a membrane of a cell. Such a sequence may be naturally present on the polypeptides of the present invention or provided from heterologous sources by recombinant DNA techniques. Such sequences include nuclear localization sequences (NLS) known in the art.

An "individual," as used herein, may be defined to include animals, such as cats, dogs, cows, horses, sheep, goats, chicken, fish, or any other animal that may be infected by retroviruses. The term also includes primates (e.g., chimpanzees) and humans.

Since the list of technical and scientific terms cannot be all encompassing, any undefined terms shall be construed to have the same meaning as is commonly understood by one of skill in the art to which this invention belongs. Furthermore, the singular forms "a", an and "the" include plural referents unless the context clearly dictates otherwise. For example, reference to a "restriction enzyme" or a "high fidelity enzyme" may include mixtures of such enzymes and any other enzymes fitting the stated criteria.

As a result of the degeneracy of the genetic code, a multitude of nucleotide sequences may be produced that are based upon the disclosed peptide, polypeptide, or protein sequences, or the amino acid sequences arising from the disclosed polynucleotide sequences. Some of these will bear only minimal homology to the sequence disclosed herein; however, this invention has specifically contemplated each and every possible variation of nucleotide sequence that could be made by selecting combinations based on possible codon choices. These combinations are made in accordance with the standard triplet genetic code as applied to the nucleotide sequence of a naturally occurring peptide, polypeptide, or protein, and all such variations are to be considered as being specifically disclosed.

Although the peptide, polypeptide, or protein-encoding nucleotide sequences and their derivatives or variants are preferably capable of hybridizing with the nucleotide sequence of the naturally-occurring peptide, polypeptide, or protein under optimized conditions, it may be advantageous to produce peptide, polypeptide, or protein-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence without altering the encoded amino acid sequence include the production of RNA transcripts having more desirable properties, such as a longer half-life, than transcripts produced from the naturally occurring sequence.

Nucleotide sequences encoding a peptide, polypeptide, or protein may be joined to a variety of other nucleotide sequences by means of well-established recombinant DNA techniques (Sambrook, J., et al. [1989] *Molecular Cloning: A Laboratory Manual*, Cold Spring Harbor Laboratory, Cold Spring Harbor, N.Y.; or Ausubel, F. M. et al. [1989] *Current Protocols in Molecular Biology*, John Wiley & Sons, New York City). Useful sequences include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease-sensitive sites, and selectable markers for one or more host cell systems.

The terms "hybridize" or "hybridizing" refer to the binding of two single-stranded nucleic acids via complementary base pairing. The phrase "hybridizing specifically to" refers to binding, duplexing, or hybridizing of a molecule to a nucleotide sequence under stringent conditions when that sequence is present in a preparation of total cellular DNA or RNA.

In addition to polynucleotide sequences specifically exemplified herein, the present invention also concerns polynucleotide sequences that hybridize to the subject sequences. Preferably, the sequences hybridize under stringent hybridization conditions. The term "stringent conditions" refers to conditions under which a polynucleotide molecule will hybridize to another sequence, but not to sequences having little or no homology to the polynucleotide. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.1 to 1.0 N sodium ion concentration at a pH of about 7.0 to 7.5, and the temperature is at least about 60° C. for long sequences (e.g., greater than about 50 nucleotides) and at least about 42° C. for shorter sequences (e.g., about 10 to 50 nucleotides).

The chimeric gag polynucleotides, chimeric gag polypeptides, and inhibitory peptides of this invention also encompass variant sequences containing mutations in the exemplified sequences; however, these variants must still retain the ability to assemble in vitro (in the case of the chimeric Gag polypeptides) and the inhibitory peptides must retain the ability to interact with Gag.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

M-PMV/HIV Chimeric Molecules

We have, surprisingly, found that the in vitro assembly of HIV capsids can be accomplished using chimeric M-PMV/HIV gag genes. A unique Gag domain of M-PMV (p12) is critical and required for chimeric Gag assembly in the in vitro translation system. We have found that the fusion of various portions of M-PMV Gag, including the p12 domain, with portions of HIV Gag, endows chimeric HIV Gag proteins with the ability to assemble in vitro.

We have constructed a number of chimeric gag genes, described below, with the purpose of endowing the HIV Gag precursor protein with the ability to assemble in our in vitro assay. As summarized in FIG. 1, the chimeric Gag polypeptides form assembled structures as assayed by gradient analysis.

Gag targets for association studies may also be constructed as a multivalent target protein. Bacterial expression vectors may be modified to contain an "Avitag" sequence in addition to the six-histidine tag. The "Avitag" is a 14-amino acid sequence that is specifically recognized and biotinylated by the *E. coli*. enzyme BirA (at either the carboxyl or amino terminus). When expressed in cells that contain this enzyme protein bearing the tag will be biotinylated in vivo. After purification under denaturing conditions on a nickel chelation column, Gag proteins are then coupled to soluble streptavidin to make a tetravalent target (FIG. 8).

Chimeric constructions containing the majority of HIV gag sequences, with the p12 region of M-PMV gag inserted, assemble in vitro. Depicted in FIGS. 2–4, chimeras 3a and 4 produce, in a manner similar to M-PMV, but unlike HIV, sedimentable material indicative of assembled particles (FIGS. 2 and 4). Furthermore, the formation of this material can be largely blocked by the addition of the hydrophobic compound bis-ANS (FIGS. 3 and 4). In contrast, bis-ANS has no effect upon the distribution of HIV Gag in sucrose gradients (FIG. 3). As shown in FIG. 5, bis-ANS and antibodies to p12 are also able to significantly reduce the formation of pelletable material by M-PMV Gag (i.e., immature M-PMV viral capsids) in a more rapid centrifugation assay. Additionally, Gag chimeras have undergone analysis by electron microscopy to confirm the formation of particles by these Gag proteins.

EXAMPLE 2

Chimera Constructions

All DNA manipulations and cloning procedures were performed according to standard techniques. Before construction of the chimeric genes described below, it was first necessary to remove the ribosomal frameshift signal within the HIV gag coding sequence. Site-directed mutagenesis was employed to introduce a silent substitution in the "shifty sequence" of HIV gag. The loss of frameshift function was confirmed in an in vitro translation system.

The frameshift signal sequence in HIV gag is AAU UUU UUA GGG (SEQ ID NO:1). To introduce the silent mutations, PCR was performed with forward primer, GGCCA-GATCTTCCCGAGGAAATTAGCCTG (SEQ ID NO:2), and reverse primer, ATAAGACAAGGACCAAAAG (SEQ ID NO:3). Plasmid pDAB72, obtained from the NIH AIDS Research and Reference Reagent Program, was used as the template. The PCR product was digested with Age I and Bgl II, and then ligated into similarly digested pDAB72. Clones were screened for the presence of an Ava I restriction site created by the introduced mutations. The resulting altered sequence is AAU UUC CUC GG (SEQ ID NO:4), which is unable to induce a ribosomal frameshift as analyzed by in vitro translation. This plasmid is designated pDAB72(FS-).

pDABCh3a (Chimera 3a)

Chimera 3a contains the coding sequences for human immunodeficiency virus (HIV) Gag, except for p1 and p6, fused to the coding sequence for the p12 domain of Mason-Pfizer monkey virus (M-PMV) Gag. Plasmid pDABCh3a was constructed by a combination of PCR amplification of gag sequences followed by restriction enzyme-mediated cloning. In the first step, the HIV gag sequences from within the CA domain through to the end of the NC domain were amplified using the forward primer MSHIV3, ATAAGA-CAAGGACCAAAGG (SEQ ID NO:5), and the reverse primer HIV CNC(-), ATTAGCCTGTCTCTCAG (SEQ ID NO:6). Plasmid pDAB72(FS-) was used as the template. Since the forward primer binds upstream of a unique Age I site in the CA domain, the resulting PCR product can be digested with this enzyme.

In the second step, the M-PMV p12 sequence was amplified using the forward primer M+Np12, GCGGTTGT-TAATCCAAAAGAGG (SEQ ID NO:7), and the reverse primer M–Cp12XmaI, ATCAACGGTCCCGGGCACTTA-GAAAATATCTTTTGG (SEQ ID NO:8). The forward primer anneals exactly to the 5' end of the p12 coding sequence, and the reverse primer anneals to the 3' end of p12, but also introduces a stop codon and an Xma I restriction site. Plasmid pSHRM15 (4) was used as the template. The resulting product can be digested with Xma I.

The third and final step was to ligate the two restriction-digested PCR products into the vector pDAB72(FS-) which had also been digested with Age I and Xma I. The insertion was performed by a "three-way" ligation in which all three pieces were included in the reaction at one time.

pDABCh3 (Chimera 3)

Chimera 3 contains the coding sequence of HIV Gag, except for p6, fused to the coding sequence for the p12 domain of M-PMV Gag. Construction began by amplifying the p12 region of M-PMV gag with forward primer M+Np12/Cp1, GGGGAGACCCGGGAATTTTGCGG TTGTTAATCCAAAAGAGGAGC (SEQ ID NO:9), and reverse primer M–Cp12XmaI. The forward primer is designed to anneal to the 5' region of M-PMV p12, but to also contain sequences that can anneal to the 3' sequence of HIV p1. The reverse primer is the same as that used for the construction of Chimera 3a.

In the second step, the product of the first PCR was used as a "megaprimer" to anneal to the 3' end of p1. In combination with forward primer MSHIV3 and reverse primer M–Cp12XmaI, the megaprimer reaction yielded a product which contained a portion of HIV CA, plus all of p2, NC, and p1 fused to M-PMV p12. This fragment was "T-A" cloned into pGEM (PGEM T-vector system, Promega). This system makes use of the fact that the Tac thermostable polymerase will terminally adenylate the PCR product. The "T-vector" contains 3' terminal thymidine overhangs that allow for complementary base pairing with the PCR product. After amplification of the pGEM vector in E. coli, the Gag fusion sequence was excised with Age I and Xma I, and ligated into the same sites in pDAB72(FS-) to yield pDABCh3.

pDABCh4 (Chimera 4)

Chimera 4 contains the coding sequence of HIV Gag protein fused to the coding sequence for the p12 domain of M-PMV Gag. Construction began by amplifying the p12 region of M-PMV gag with forward primer M+Np12/Cp6, GGCAACGACCCCTCGTCACAAGCGGTTGTT AATC-CAAAAGAGGAGC (SEQ ID NO:10), and reverse primer M–Cp12XmaI. The forward primer is designed to anneal to the 5' region of M-PMV p12, but to also contain sequences that can anneal to the 3' sequence of HIV p6. The reverse primer is the same as that used for the construction of Chimera 3a. In the second step, the product of the first PCR was used as a "megaprimer" to anneal to the 3' end of p6. In combination with forward primer MSHIV3 and reverse primer M–Cp12XmaI, the megaprimer reaction yielded a product that contained all of HIV Gag fused to M-PMV p12. This fragment was "T-A" cloned into pGEM (PGEM T-vector system, Promega). After amplification of the pGEM vector in E. Coli, the Gag fusion sequence was excised with Age I and Xma I, and ligated into the same sites in pDAB72(FS-) to yield pDABCh4.

EXAMPLE 3

Binding Peptide Screening Assays

There are a number of assays by which peptide inhibitors of the subject invention may be identified. One such assay utilizes the yeast two-hybrid system for the identification of binding peptides. The binding peptides of this invention may reduce or inhibit the assembly of Gag polypeptides into capsids.

Chimeric Gag protein is expressed as a fusion with the GAL4-DNA-binding domain, and will be co-expressed with the GAL4 activation domain fused to a random sequence library encoding a decameric peptide or a semi-random peptide library. This approach has been used successfully to select peptides from a random library that could bind the Rb protein (Yang, et al. (1995)).

Construction of GAL-4-Gag Plasmids

The chimeric gag genes are cloned into GAL4 expression vectors well-known in the art (see for example, Wim Van Criekinge, et al. [1999] Biological Procedures Online, 2(1): 1–38). For example, the complete chimeric gag gene from the initiating AUG to the terminator are cloned into a BamHI site placing the entire coding sequence in frame and downstream of the GAL4 coding sequences.

Construction of Peptide Library Expression Vectors

For construction of the GAL4 activation domain/peptide constructs, and for the peptide expression libraries, we will utilize two different approaches.

a. Random Peptide Library

For this library, a degenerate oligonucleotide will be synthesized in which the first two positions of each fully-degenerate codon will be made by adding an equimolar mixture of dA, dC, dG, and dT to the growing oligonucleotide chain; the third position will have an equal mixture of dG and dT. The resulting mixture of 32 triplets encodes all 20 amino acids (and only the amber termination codon). The degenerate 10-codon sequence will be flanked by nondegenerate sequences containing a 5' BamHI and a 3' EcoRI restriction enzyme site to allow both the annealing of PCR primers and subsequent cloning. The template will be PCR amplified using 5'-biotinylated primers corresponding to the flanking regions. After five cycles of amplification, aliquots of the DNA product are digested with the appropriate enzymes and the insert purified from unwanted digestion products on avidin-agarose beads. Inserts will be cloned via homologous restriction sites into a high-expression derivative of the GAL4 activation domain fusion plasmid. A similar 16-mer random peptide librarywas used successfully for selection of Rb-bindingpeptides (Yang, M., et al (1995), "Protein-peptide interactions analyzed with the yeast two-hybrid system," *Nucleic Acids Res* 23, pp. 1152–6) and is also available for the identification of peptide inhibitors.

b. Semi-Random Gag-Based Peptide Libraries

Because capsid assembly involves the homotypic interactions of multiple Gag molecules, peptides based upon the sequence of a retroviral Gag polypeptide itself, might be predicted to interact with the precursor in a competitive fashion to terminate the growth of capsid structures. A more comprehensive randomized approach in which the gag gene is digested with a non-specific endonuclease to produce a library of gene fragments may be used to identify peptide inhibitors of capsid assembly. These gene fragments will be cloned into the appropriate expression vector (such as a vector containing the Gal4 activation domain) and the resulting library screened in the two-hybrid assay for inhibition of assembly and binding to chimeric Gag proteins. The technology to produce such a library is commercially available as part of the Novatope Epitope Mapping System (Novagen, Inc.); the random degradation methodology is available as a separate "DNase Shotgun Cleavage Kit," which will be used to produce 1O-mer libraries based upon the HIV and M-PMV gag genes. Because the technology uses random cleavage and non-directional cloning, amino acid sequences identical to those of the exemplary Gag polypeptides will represent a subset of the total. This approach provides some of the benefits of chemically synthesized random libraries, which require sequencing by micro-Edman degradation, with the convenience of DNA sequencing. The theoretical number of clones required to achieve a given probability that a specific sequence will $$N=[ln(1-P)/ln(1-1/n)] \times 6$$

be present in the library is:

where N=the number of clones required, P=the probability desired, and 1/n=the fractional proportion of the total sequence represented by the peptide. Thus, for HIV Gag, a 500 amino acid protein, the number of clones necessary at a probability of 99% for a 10-amino acid peptide is approximately 1,400 clones. For the 657 amino acid M-PMV Gag protein, the number of clones is approximately 1,800. These are numbers that can be readily screened on a few plates.

To screen for interacting peptides, we will transform yeast cells (strain GGY1::171 for his and leu selection, or strain Y190 for trp and leu selection) that carry a GAL1-lacZ fusion integrated into the chromosome, using the high-efficiency method of Schiestl and Gietz (Schiestl, R. H., et al. (1989), "High efficiency transformation of intact yeast cells using single stranded nucleic acids as a carrier," *Curr Genet* 16, pp. 339–46) with the chimeric Gag/DNA binding domain plasmid, along with either the random or Gag-based peptide-library fused to the GAL4 activation domain. Prototrophic transformants will be screened for β-galactosidase expression by replica-plating colonies onto nitrocellulose filters which will be permneablized by exposure to liquid nitrogen, then soaked in buffer containing X-Gal, and incubated overnight at 30° C. Those colonies that turn blue will be selected. The library plasmids from the transformants that score as positive will be transformed into *E. coli* for amplification. These plasmids will then be reintroduced into the yeast strain used for screening either alone, with the GAL4 DNA-binding domain vector (with no insert) or with the chimeric Gag/GAL4 DNA-binding domain vector. These subsequent transformations are necessary to rule out non-specific activation of GAL4.

Plasmids exhibiting specificity in these secondary assays will be sequenced to determine the sequence of the encoded peptide. These peptides will be screened in vivo a second time in the competition assay described below prior to being synthesized and analyzed in the assembly assay.

EXAMPLE 4

Yeast Two-hybrid Competition/inhibition Assay

The in vivo yeast-two hybrid method may also be used to screen for peptides in both the random and Gag-based libraries that can inhibit the association of Gag molecules. We will establish yeast cell lines carrying the chimeric Gag/GAL4 DNA-binding domain (HIS3 selectable) and the GAL4 activation domain (LEU2 selectable) expression plasmids which will yield colonies that have the integrated GAL1-lacZ gene constitutively expressed.

In the competition assay, these cells will then be transformed by high-expression plasmids containing the random or Gag-based peptide libraries fused to a mutant GAL4 activation domain and with a TRP1 selectable marker. Peptide fusions that can efficiently compete for Gag-Gag interactions would be expected to yield an inactive GAL4 DNA-binding domain/activation domain complex, and thus would not be able to activate the lacZ gene. Colonies in which β-galactosidase expression is absent (white) or severely reduced will be selected and the library plasmids recovered. Following growth in a bacterial host, the ability of the peptide-activation domain fusion to compete with the chimeric Gag/GAL4 activation domain fusion will be confirmed by re-transformation and non-specific loss of one or the other components of the system.

The inhibition assay will be based on a similar competition principle, except in order to rule out the possibility that the activation domain of GALA might mask or interfere with some potential peptide interactions. We will construct a high level expression vector, which has the ADH1 promoter from pGAD GH to drive expression of the random and Gag-based peptides fused at the N terminus to the SV40 nuclear localization signal. This will allow the expression of high levels of soluble small peptides that can target the Gag-Gag interaction.

As in the case of the plasmids isolated from the direct two-hybrid screen, it will be possible to reciprocally test peptide-encoding sequences that act as competitors/inhibitors in the above assay, for their ability to directly bind to Gag and activate GAL4 in the two-hybrid system. The sequences of the peptides will be determined from the nucleotide sequences of the plasmids, and peptides will be synthesized for secondary binding and assembly inhibition assays.

EXAMPLE 5

In vitro Assembly Assays

In vitro assembly assays, such as that taught by Sakalian, M., et al. (1996), "Synthesis and assembly of retrovirus Gag precursors into immature capsids in vitro," *J Virol* 70, pp. 3706–15, hereby incorporated by reference in its entirety, maybe used to screen for inhibitors of capsid assembly. Briefly, in vitro transcription of chimeric gag -containing plasmids to produce capped RNA transcripts may be performed using the mMESSAGE MMACHINE kit (Ambion, Austin, Tex.), in accordance with the manufacturers instructions. Translation reactions may be performed in the presence of [$^{35}$S]methionine in commercially-available rabbit reticulocyte lysates, according to the instructions of the manufacturer (for example, Promega). Alternatively, transcription and translation reactions maybe performed simultaneously with the chimeric gag genes in the TNT Coupled Reticulocyte Lysate System (Promega). Inhibitors of retroviral Gag assembly, such as peptide libraries, are added about 30 minutes after incubation is initiated. The lysates are then assayed by sucrose gradients and SDS-PAGE for assembled products. Samples exhibiting no sedimentable material are indicative of inhibitors of Gag assembly, whereas samples that exhibit sedimentable material are indicative of assembled Gag particles.

Prior to fractionation on sucrose gradients, translation reactions were incubated for 10 minutes on ice with 1% Triton X-100. Detergent-treated lysates were then diluted to a total volume of 100 µl with 30% (wt/wt) sucrose in 20 mM Tris (pH 8.0)-100 mM NaCl-100 µM dithiothreitol-0.1% Triton X-100 (gradient buffer), and loaded onto 2.2-ml continuous 30 to 55% (wt/wt) sucrose gradients in gradient buffer. Gradients were centrifuged in a TLS-55 rotor (Beckman Instruments) for 2 hours at 55,000 rpm. Approximately 200-µl fractions were taken by hand with a Pipetman (Gibson) from the top of the gradient. The pellet was resuspended in 200 µl of 55% (wt/wt) sucrose in gradient buffer. Aliquots (5 or 10 µl ) of each fraction were dissolved in sodium dodecyl sulfate (SDS) sample buffer and then loaded onto an SDS-12.5% polyacrylamide gel. After polyacrylamide gel electrophoresis (PAGE), radioactive bands were visualized by fluorography of sodium salicylate-impregnated gels.

Particulate material present in in vitro translation reactions can be prepared for analysis by thin-section electron microscopy by dilution of the reaction two-fold into gradient buffer followed by centrifugation at 70,000 rpm for 30 minutes in a TLA-100.3 rotor (Beckman Instruments). For analysis of sucrose density-gradient material, fractions and the resuspended pellet were diluted two-fold into gradient buffer, and then loaded into Beckman microcentrifuge tubes containing a 20-µl plug of 0.8% agarose prepared in gradient buffer. Loaded tubes were centrifuged first at 30,000 rpm for 1 hour, and then immediately again, without a stop, at 70,000 rpm for 1 hour in a TLA-100.3 rotor with microcentrifuge tube inserts (Beckman Instruments).

All pellets were fixed overnight in 1% glutaraldehyde in phosphate-buffered saline (PBS), pH 7.0 at 4° C. After a rinse in PBS, pellets were post-fixed in 1% buffered osmium tetroxide for 1 hour. These pellets were rinsed once more and then dehydrated in a graded series of ethanol solutions beginning with 50% and ending with 100%. After dehydration, pellets were rinsed three times with propylene oxide and then embedded in Polybed. Ultrathin sections were acquired by using a Rechert-Jung Ultra Cut E ultramicrotome. After staining with uranyl acetate and lead citrate, sections were examined and photographed by using a Hitachi-7000 transmission electron microscope.

In vitro Peptide Synthesis

In order to program high-level synthesis of peptides in the in vitro translation/assembly system, PCR primers containing Msc I and Bgl II restriction sites, as well as flanking start and stop codons, will be prepared and the sequence amplified from plasmid DNA. These new restriction sites can then be used to clone each sequence into pCITE-4c(+) (Novagen) for efficient expression in vitro. The resulting peptide will, for a candidate decamer, have the sequence met-ala-thr-gly-gly-X10-gly-gly. Should one of the chosen restriction sites be present within the candidate peptide's DNA sequence, alternative sites are available in the plasmid; although, the length and composition of the N-terminal leader sequence will be altered.

EXAMPLE 6

Synthetic Peptide Libraries as Sources for Inhibitory Peptides

Synthetic peptide combinatorial libraries (SPCL) have a number of advantages over combinatorial libraries synthesized in vivo. SPCL can include both L and D amino acids, the peptides can be cyclized, or non-peptide polymeric subunits can be added along with a peptide decoding chain (Nikolaiev, V., et al. (1993), "Peptide-encoding for structure determination of nonsequenceable polymers within libraries synthesized and tested on solid-phase supports," *Pept Res* 6, pp. 161–70). In addition, analysis of a synthetic library in vitro eliminates the concerns created by the cellular environment.

The "one-bead/one-peptide" (Selectide) approach of Lam, K. S., et al (1991), "A new type of synthetic peptide library for identifying ligand-binding activity" [published errata appear in Nature 1992 Jul. 30;358(6385):434 and 1992 Dec. 24–31;360(6406): 768], *Nature* 354, pp. 82–4, is one example of SPCL suitable for the identification of peptide inhibitors of this invention. This process is based on a technique of random compound synthesis of oligomers produced by a solid phase chemical synthesis that, in turn, is conducted in such a way that each individual compound in the library is represented on a separate solid-phase resin bead where it was synthesized. This can be achieved by producing the compounds using standard solid phase peptide synthesis methods with the technique of split synthesis (Lam et al., 1991). Individual beads (approximately 120 µm in diameter) within a batch of resin used for synthesis are divided up into different reaction vessels, one for each amino acid to be added to a growing polymer. After each cycle of deprotection and building block addition (using Boc or Fmoc-protected amino acids and sufficient time to allow the reaction step to go to completion), the beads are recovered and pooled from the various vessels, washed and thoroughly mixed, and then redistributed into the vessels again for the next addition step. Addition of 5 amino acids to yield pentapeptide libraries using 19 amino acids (cysteine is omitted to eliminate disulfide cross-linking), can produce a total of up to 2,476,099 individual peptides of differing sequences with any one sequence represented on at least one solid-phase resin bead.

The target molecule, coupled to an enzyme such as alkaline phosphatase, is added in soluble form to the peptide bead library. hi previous work, Lam et al. (1991), found that a few beads stained intensely and were visible using a low-powered dissecting microscope against a background of colorless non-reactive beads. Using microforceps coupled to a micromanipulator, the intensely staining beads could be removed for analysis. After washing each bead with 8M guanidine hydrochloride to remove the target complex, the peptide sequence of the bead can be determined in a peptide microsequencer (Applied Biosystems). Salmon et al. (Salmon, S. E., et al. (1993), "Discovery of biologically active peptides in random libraries: solution-phase testing after staged orthogonal release from resin beads," *Proc Natl Acad Sci USA* 90, pp. 11708–12) have extended this concept to solution-phase screening with the use of staged orthogonal release linkers (Lebl, M., et al. (1993), "Multiple release of equimolar amounts of peptides from a polymeric carrier using orthogonal linkage-cleavage chemistry," *Int J Pept Protein Res* 41, pp. 201–3). In this way, one-third of the peptide on each bead can be released at neutral pH, and one-third at high pH, while the final third remains on the bead for sequencing. This modification allows for direct screening in solution of large random libraries, but since approximately 100 picamoles of peptide can be released from individual beads, the soluble peptide from each can be tested directly in a binding assay. We plan to utilize this approach in conjunction with our in vitro assembly assays to screen for peptides capable, not only of binding, but of inhibiting the assembly process.

EXAMPLE 7

Release of Individual Peptides

Orthogonal release linkers outlined previously may also be used to identify peptides that interact with Gag. Gag molecules (and possibly the diketopiperazine-linked peptide) may be removed with acidified 8M guanidine hydrochloride. A third of the initiallyconjugatedpeptide may then be removed by cleavage of the ester linkage at high pH (Salmon, S. E., et al. (1993), "Discovery of biologically active peptides in random libraries: solution-phase testing after staged orthogonal release from resin beads," *Proc Natl Acad Sci USA* 90, pp. 11708–12). This soluble peptide could then be used in the assay for inhibition in the in vitro translation/assembly system.

EXAMPLE 8

Assay of active peptides in infectivity assay

Niedrig et al. (Niedrig, M., et al. (1994), "Inhibition of infectious human immunodeficiency virus type 1 particle formation by Gag protein-derived peptides," *Journal of General Virology* 75, pp. 1469–74) demonstrated that peptides corresponding to regions of HIV Gag could inhibit the production of infectious virus from cells in culture, although these did not block assembly per se. Each of the interactive peptides identified by both the two-hybrid and Selectide techniques will therefore be examined for their ability to interfere with both the production of virus particles and the propagation of infectious virus. These studies will be carried out in a similar manner to the long-term inhibition experiments described by Wild et al. (Wild, C., et al. (1992), "A synthetic peptide inhibitor of human immunodeficiency virus replication: Correlation between solution structure and viral inhibition," *Proc. Natl. Acad. Sci. USA* 89, pp. 10537–41) for a synthetic peptide derived from gp41 (TM) of HIV. In addition, pulse-chase experiments will be carried out on gag -expressing cells in the presence and absence of varying amounts of peptide to determine whether Gag-polyproteins, synthesized during the pulse, are inhibited from assembling into new virions.

EXAMPLE 9

M-PMV p12 Deletion Mutants

DNA constructs. Plasmid pTFCG.M100A is a derivative of plasmid pTFCG, which contains the encephalomyocarditis virus cap-independent translation enhancer element and M-PMV gag, pro, and pol, flanked by a T7 promoter and a T7 terminator (Sakalian, M.; et al. [1996], *J. Virol.* 70:3706–3715). Plasmid pTFCG was modified to create pTFCG.M100A by replacing the methionine codon at position 100 with that for alanine. This was accomplished by substitution of the PacI-to-SacI fragment of pTFCG with the same fragment containing the modification form pGAG78, an infectious molecular clone of M-PMV based upon pSHRM15 (Rhee, S. S., et al. (1987), "Myristylation is required for intracellular transport but not for assembly of D-type retrovirus capsids," *J. Virol*, 61, pp. 1045–53). The phenotype of virus produced after transfection of pGAG78 into cells in culture was previously found to be indistinguishable from that of the wild type.

Plasmid pTFCG.R55W.M100A was constructed in the following manner: plasmid pTFCG was partially digested by Psp406I. Linear vector was isolated and then further digested with BsgI, and the desired 8.6-kb fragment was isolated. This fragment was then ligated with the 1.9-kb *Psp*1406I-to-*BsgI* fragment of pSHRMI5.R55W (Rhee, S. S., et al. (1990), "A single amino acid substitution within the matrix protein of a type D retrovirus converts its morphogenesis to that of a type C retrovirus," *Cell* 63, pp. 77–86; Rhee, S. S., et al. (1987), *J. Virol.* 61, pp. 1045–53the arginine-to-tryptophan codon substitution. The resulting plasmid, pTFCG.R55W, was then also modified, as described above for pTFCG, to introduce the M100A substitution. The presence of the two mutations was confirmed by sequencing.

Plasmids pTFCGΔ1-83, pTFCGΔ1-25, pTFCGΔ26-53, and pTFCGΔ54-83 were constructed by moving the 1.5- to 2.3-kb ScaI-to-BsgI fragment containing the p12 domain deletions from pSHRM15Δ8-58, pSHRM15Δ1-83, pSHRM15Δ1-25, pSHRM15Δ26-53, and pSHRM15Δ54-83 (Sommerfelt, M. A., et al. (1992), "Importance of the p112 protein in Mason-Pfizer monkey virus assembly and infectivity," *J. Virol.* 66, pp. 7005–11), respectively, into the corresponding position of pTFCG.M100A that had been digested with BsgI and partially digested with ScaI. The M100A substitution was retained by this strategy.

Plasmids pETΔ8-58, pETΔ1-83, pETΔ1-25, pETΔ26-53, and pETΔ54-83 were constructed by replacing the PacI-NdeI fragment of pETGagHis$_6$ with the corresponding fragments of pTFCGΔ8-58, pTFCGΔ1-83, pTFCGΔ1-25, pTFCGΔ26-53, and pTFCGΔ54-83, respectively. Plasmid pETGagHis$_6$ (a generous gift of Robert A. Weldon, Jr.) was constructed by PCR amplification and subjoining steps. First, the p12 and CA coding regions were amplified by PCR with the primers PR1141 (5'-GGCGGTTGTTAATCC (SEQ ID NO:11)), which was designed to anneal to gag sequences located just upstream of the p12 coding sequence, and p4XhoI (5'-CAGCTCGAGATACTTGTGTGG (SEQ ID NO: 12)), which was designed to insert an XhoI site at the 3' end of gag, such that six histidine codons would be placed directly adjacent to the last codon of gag. After PCR amplification of pSHRM15 with these primers, the SacI-XhoI fragment of the PCR product was cloned into corresponding sites of pET-21d (Novagen, Inc.). To subclone the 5' end of gag, the NcoI-SacI fragment of pSITGAGPP, a derivative of pSIT (1) containing gag, pro, and pol of M-PMV, was inserted into the homologous sites to finally construct pETGagHis$_6$. After each subjoining step, the plasmid DNAs were sequenced to ensure that unwanted mutations were not inadvertently created.

Plasmid pET.R55W.M100A was constructed by transfer, after digestion, of the 1.5-kb BssHI-to-PacI fragment of pET.ANC.R55W, which contains the 5' sequence of gag including the R55W substitution, into the 5.8-kb PacI-to-BssHI vector fragment of pET.M100A. Plasmid pET.M100A was constructed by first PCR-amplifying the MA-p12 coding regions of pGAG78 by using the primers Nco485 (5'-GATATACCATGGGGCAA (SEQ ID NO:13)), which contains an NcoI site, and RP 1179 (5'-TCCTCTAATTGAGCAA (SEQ ID NO: 14)). After digestion of the PCR product with NcoI and SacI, the resulting product was used to replace the NcoI-SacI fragment of pETGagHis$_6$.

EXAMPLE 10

Expression of Gag Species in Bacteria

Bacterial expression plasmids of the pET series were transfected into *Escherichia coli* strain BL2 1 (DE3), which had already been transformed with plasmid pBB 131, which contains the *Saccharomyces cerivisiae* gene for protein N-myristoyltransferase (plasmid pBB 131 was the kind gift of J. I. Gordon, Dept. of Molecular Biology and Pharmacology, Washington University School of Medicine, St. Louis, Mo.). Cells were grown in Luria broth containing 500 µM myristic acid. Production of both Gag and myristoyltransferase was induced with 500 µM isopropyl-□-D-thiogalactopyranoside (IPTG). Cells were harvested after 4 hours of induction by centrifugation at 14,000 rpm in an Eppendorf microcentrifuge (Brinkman). Expressed product was examined by sucrose gradient analysis and electron microscopy, as described above in Example 5.

Figure 6:
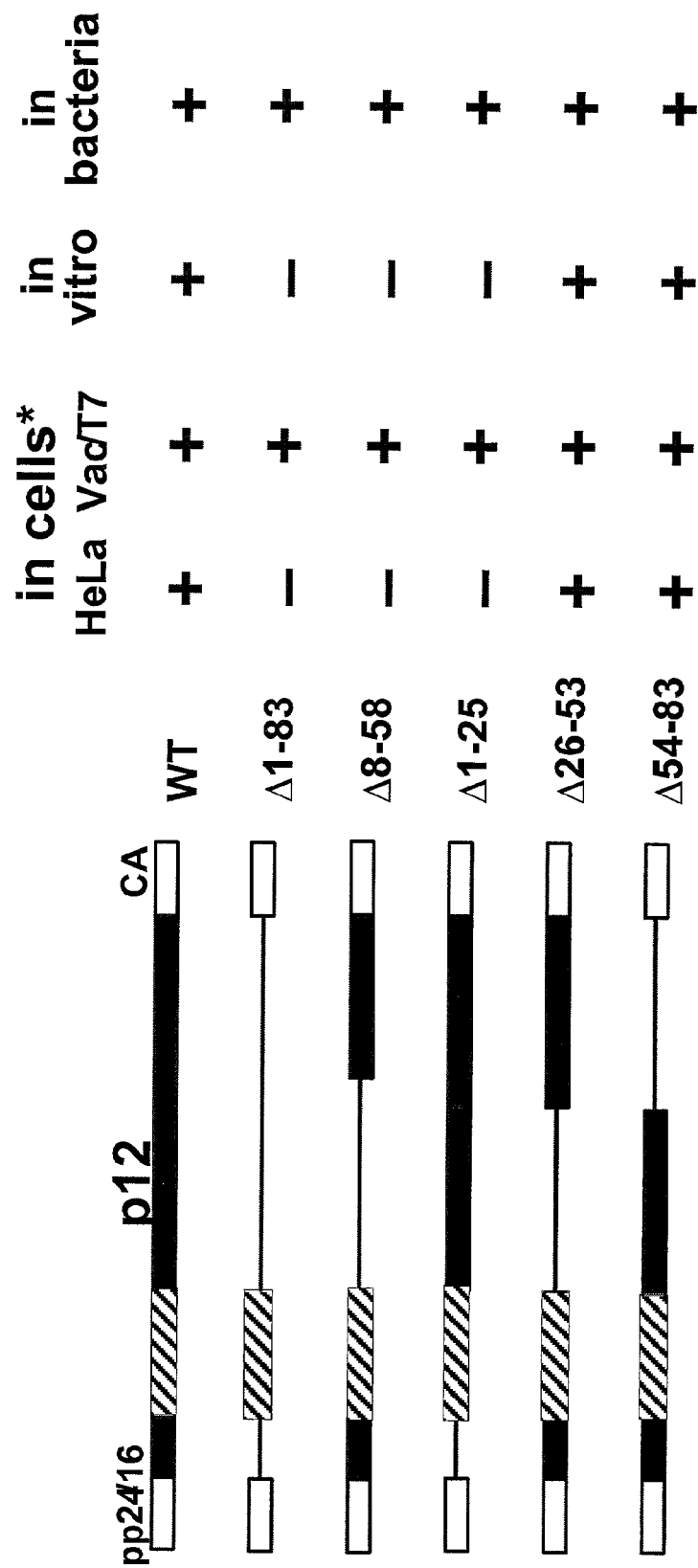
FIG. 6—Schematic of p12 domain deletion mutants of Gag are shown with those regions of the domain present being depicted in wide bars and deleted regions shown by thin lines. The cross hatched (////) region depicts the residues associated with Gag assembly under lower expression levels (i.e., those mimicking expression levels in vivo). HeLa and Vac/T7 refer to expression of Gag in provirus-transfected HeLa cells and over expression by the vaccinia virus/T7 polymerase system in CV-1 cells. Plus and minus signs indicate the presence or absence of assembled immature capsid structures.
Figure 7B:
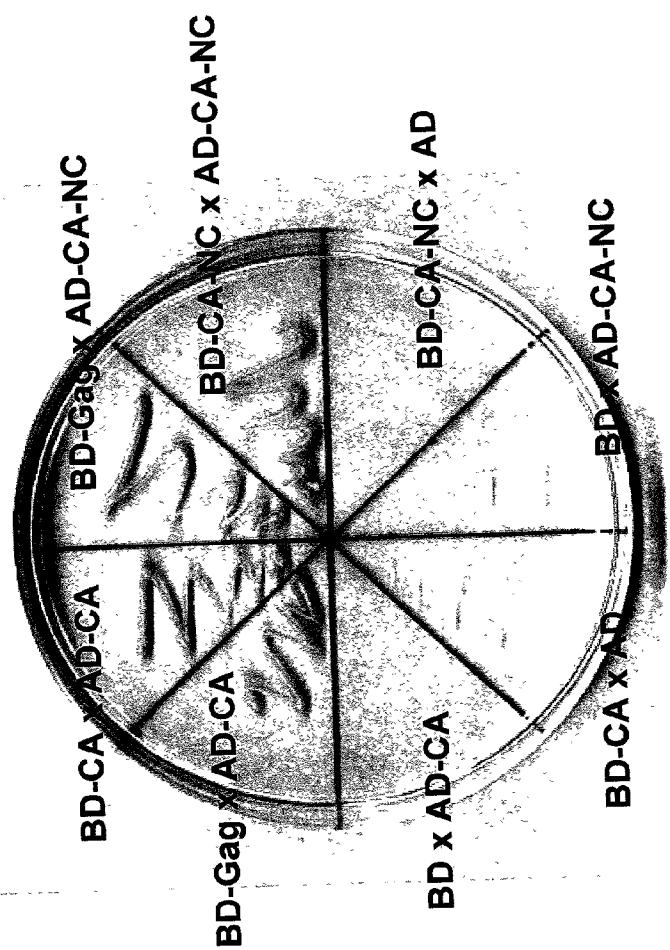
FIG. 7B: Interaction of Gag with CA-NC and CA induces growth. Single fusion controls fail to exhibit growth.
Figure 7A:
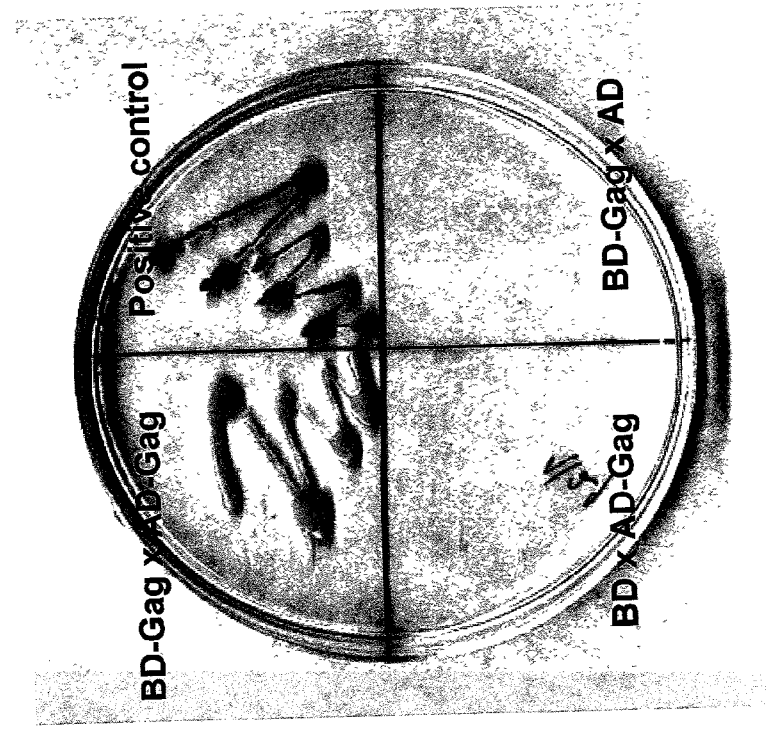
FIGS. 7A and B—Growth of yeast resulting from the interaction of Gag species in the Matchmaker Two-Hybrid System (Clontech, Inc., Palo Alto, Calif.). Left Panel.
Figure 8:
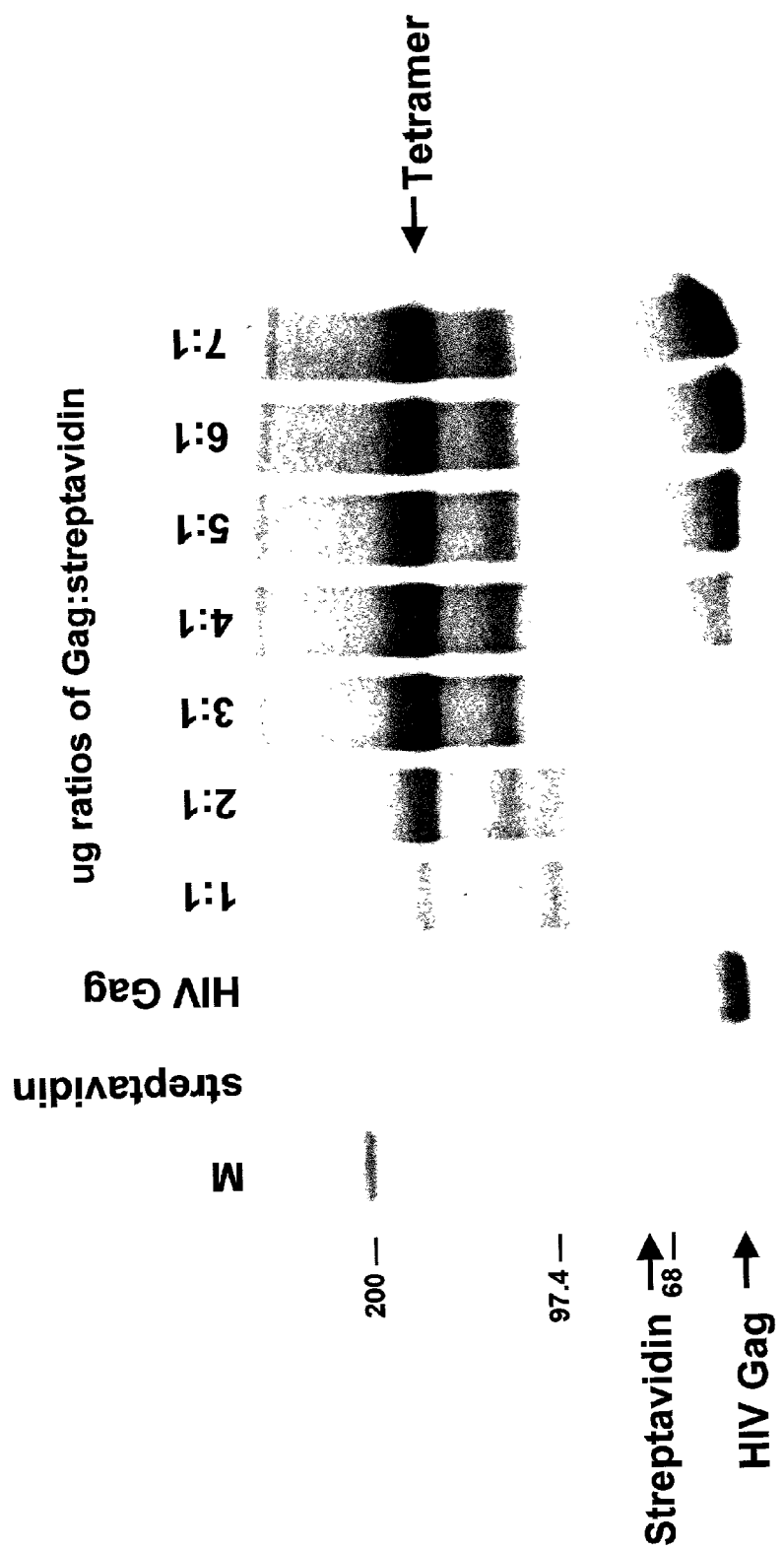
FIG. 8—Gag tetramers produced for a library screen were expressed from a vector containing both a six histidine tag and an "Avitag" (or BirA) biotinylation target sequence. Gag species were purified from 6M guanidine bacterial cell lysates by metal chelation chromatography on nickel agarose resin. After elution from nickel agarose with imidazole in 8M urea, Gag was added to a constant amount of streptavidin in buffer at a final concentration of 2M urea. The Gag/streptavidin complexes were analyzed by non-reducing SDS-PAGE and Coomassie-blue staining.
Figure 10A:
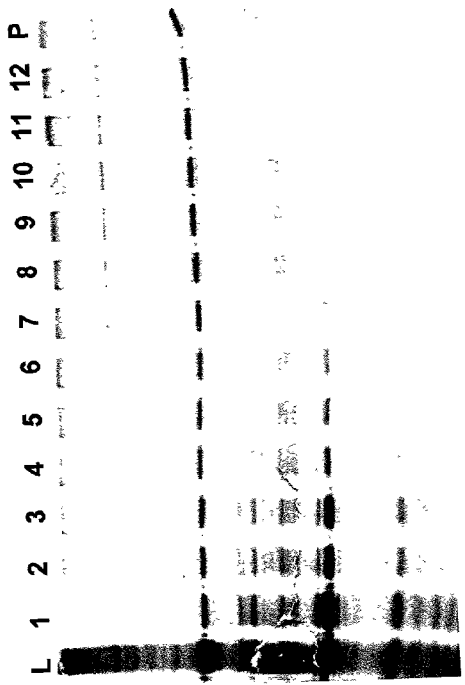
FIGS. 10A–B: An HIV Gag Sequence Mutation Renders a Chimera Assembly Defective: An assembly defective mutation within the CA domain of HIV Gag, M185A, was introduced into Chimera 4. Incorporation of this mutation results in a severe defect in the ability of Chimera 4 to assemble (FIG. 10B), indicated by the lack of a peak of sedimented material in fractions 8–11. This result shows that the HIV CA domain plays a necessary role in assembly in the context of this chimera and that the ability to form immature retrovirus-like structures is not solely the function of the introduced M-PMV Internal Scaffold Domain.
Figure 10B:
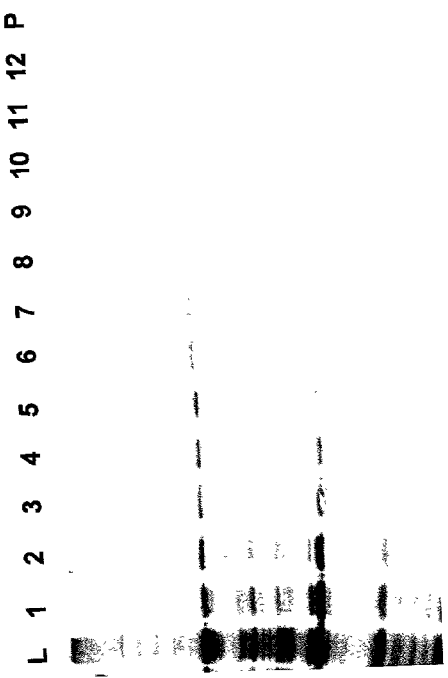

FIG. 6 depicts the summary of assembly by Gag p12 deletion mutants. The ability of various mutants to assemble in vitro and in bacteria was compared to the results of expression in tissue culture cell lines (Sakalian, et al. [1999]*, J. Virol.* 73(10):8073–8082, hereby incorporated by reference in its entirety). Schematics of the p12 domain of Gag are shown with those regions of the domain present being depicted in wide bars and deleted regions shown by thin lines. The cross-hatched region depicts the residues associated with Gag assembly under lower expression levels (i.e., those mimicking expression levels in vivo). HeLa and Vac/T7 refer to expression of Gag in provirus-transfected HeLa cells and over expression by the vaccinia virus/T7 polymerase system in CV-1 cells. Plus and minus signs indicate the presence or absence of assembled immature capsid structures.

---

We claim:

1. A chimeric Gag polypeptide comprising: (a) at least a portion of the Mason-Pfizer Monkey Virus (M-PMV) p12 domain comprising residues 1–25 of said M-PMV p12 domain; and (b) at least a portion of a heteroloaous retroviral Gag polypeptide comprising a functional CA domain, wherein said portion of said p12 domain has an N terminus adjacent to said heterologous retroviral Gag polypeptide, and wherein said portion of said p12 domain induces the spontaneous assembly of said chimeric Gag polypeptide into viral capsids within mammalian cells in vitro or under extra cellular in vitro conditions, in the absence of a capsid assembly inhibitor.

2. The chimeric Gag polypeptide according to claim 1, wherein said heterologous retroviral Gag polypeptide is obtained from human immunodeficiency virus (HIV).

3. The chimeric Gag polypeptide according to claim 2, wherein said human immunodeficiency virus is HIV-1.

4. The chimeric Gag polypeptide according to claim 2, wherein said human immunodeficiency virus is HIV-2.

5. The chimeric Gag polypeptide according to claim 1, further comprising at least one tag.

6. The chimeric Gag polypeptide according to claim 5, wherein said tag is a polyhistidine tag, a biotin tag, or a combination of polyhistidine and biotin tags.

7. The chimeric Gag polypeptide according to claim 1, further comprising a biotinylation recognition sequence.

8. A chimeric Gag polypeptide comprising: (a) a Mason-Pfizer Monkey Virus (M-PMV) p12 domain; and (b) at least a portion of a heterologous retroviral Gag polypeptide comprising a functional CA domain, wherein said p12 domain has an N terminus adjacent to said heterolocious retroviral Gag polypeptide, and wherein said M-PMV p12 domain induces the spontaneous assembly of said chimeric Gag polypeptide into viral capsids within mammalian cells in vitro or under extra cellular in vitro conditions, in the absence of a capsid assembly inhibitor.

9. A composition comprising a carrier and a chimeric Gag polypeptide, wherein said chimeric Gag polypeptide comprises: (a) comprising at least a portion of the Mason-Pfizer Monkey Virus (M-PMV) p12 domain comprising residues 1–25 of said M-PMV p12 domain; and (b) at least a portion of a heteroloaous retroviral Gag polypeptide comprising a functional CA domain, wherein said portion of said p12 domain has an N terminus adjacent to said heterolopous retroviral Gag polypeptide, and wherein said portion of said p12 domain, induces the spontaneous assembly of said chimeric Gag polypeptide into viral capsids within mammalian cells in vitro or under extra cellular in vitro conditions, in the absence of a capsid assembly inhibitor.

10. The composition of claim 9, wherein said composition further comprises a capsid assembly inhibitor, wherein said capsid assembly inhibitor inhibits the assembly of said chimeric Gag polypeptide into viral capsids.

11. The composition of claim 10, wherein said capsid assembly inhibitor is selected from the group consisting of an antibody, an antibody fragment, a peptide, and a hydrophobic compound.

12. A composition comprising a carrier and a chimeric Gag polypeptide, wherein said chimeric Gag polypeptide comprises: (a) a Mason-Pfizer Monkey Virus (M-PMV) p12 domain; and (b) at least a portion of a heteroloaous retroviral Gag polypeptide comprising a functional CA domain, wherein said p12 domain has an N terminus adjacent to said heterolopous retroviral Gag polypeptide, and wherein said M-PMV p12 domain induces the spontaneous assembly of said chimeric Gag polypeptide into viral capsids within mammalian cells in vitro or under extra cellular in vitro conditions, in the absence of a capsid assembly inhibitor.

13. The composition of claim 12, wherein said composition further comprises a capsid assembly inhibitor, wherein said capsid assembly inhibitor inhibits the assembly of said chimeric Gag polypeptide into viral capsids.

14. The composition of claim 13, wherein said capsid assembly inhibitor is selected from the group consisting of an antibody, an antibody fragment, a peptide, and a hydrophobic compound.

15. The chimeric Gag polypeptide according to claim 1, wherein said viral capsids are crescent-shaped when viewed in cross-section during assembly by electron microscopy.

16. The chimeric Gag polypeptide according to claim 8, wherein said heterologous retroviral Gag polypeptide is obtained from human immunodeficiency virus (HIV).

17. The chimeric Gag polypeptide according to claim 16, wherein said human immunodeficiency virus is HIV-1 or HIV-2.

18. The chimeric Gag polypeptide according to claim 8, wherein said viral capsids are crescent-shaped when viewed in cross-section during assembly by electron microscopy.

19. The composition of claim 9, wherein said viral capsids are crescent-shaped when viewed in cross-section during assembly by electron microscopy.

20. The composition of claim of claim 12, wherein said viral capsids are crescent-shaped when viewed in cross-section during assembly by electron microscopy.

21. An chimeric Gag polypeptide comprising the amino acid sequence of SEQ ID NO:17.

22. A composition comprising a chimeric Gag polypeptide and a carrier, wherein said chimeric Gag polypeptide comprises the amino acid sequence of SEQ ID NO:17.

23. A viral capsid comprising assembled chimeric Gag polypeptides: wherein said chimeric Gag polypeptides comprise: (a) at least a portion of the Mason-Pfizer Monkey Virus (M-PMV) p12 domain comprising residues 1–25 of said M-PMV p12 domain; and (b) at least a portion of a heteroloaous retroviral Gag polypeptide comprising a functional CA domain, wherein said portion of said p12 domain has an N terminus adjacent to said heterologous retroviral Gag polypeptide, and wherein said portion of said p12 domain induces the spontaneous assembly of said chimeric Gag polypeptide into viral capsids within mammalian cells in vitro or under extra cellular in vitro conditions, in the absence of a capsid assembly inhibitor.

24. The viral capsid of claim 23, wherein said viral capsid comprises all of said M-PMV p12 domain.

25. A viral capsid comprising assembled chimeric Gag polypeptides comprising the amino acid sequence of SEQ ID NO:17.

26. The composition of claim 9, wherein said heterologous retroviral Gag polypeptide is obtained from human immunodeficiency virus (HIV).

27. The viral capsid of claim 23, wherein said heterologous retroviral Gag polypeptide is obtained from human immunodeficiency virus (HIV).

* * * * *

UNITED STATES PATENT AND TRADEMARK OFFICE
CERTIFICATE OF CORRECTION

PATENT NO. : 7,148,325 B2
APPLICATION NO. : 09/968355
DATED : December 12, 2006
INVENTOR(S) : Michael Sakalian and Eric Hunter It is certified that error appears in the above-identified patent and that said Letters Patent is hereby corrected as shown below:

Title page, (57) Abstract,
Line 5, "retrovrial capsid" should read --retroviral capsid--.

Column 1,
Lines 66 and 67, "Kraiusslich, H.-G., et al." should read --Kräusslich, H.-G., et al.--.

Column 2,
Line 6, "Pr160 gag-pol" should read --Pr160gag-pol--.

Column 3,
Line 63, "three-stranded P-sheet" should read --three-stranded β-sheet--.

Column 6,
Lines 51-52, "(K8, R20, R22" should read --(K18, R20, R22--.
Lines 52-53, "for inter with" should read --for interaction with--.

Column 14,
Line 22, "sequences maybe obtained" should read --sequences may be obtained--.

Column 17,
Line 33, "antibodies maybe naturally" should read --antibodies may be naturally--.

Column 18,
Line 28, "VH and VL domains" should read --$V_H$ and $V_L$ domains--.

Column 23,
Line 66, "(PGEM T-vector system" should read --(pGEM T-vector system--.

Column 24,
Lines 24-25, "(PGEM T-vector system" should read --(pGEM T-vector system--.

Column 25,
Line 11, "peptide librarywas used" should read --peptide library was used--.
Line 12, "of Rb-bindingpeptides" should read --of Rb-binding peptides--.
Line 33, "produce 1O-mer libraries" should read --produce 10-mer libraries--.
Line 66, "permneablized" should read --permeabilized--.

UNITED STATES PATENT AND TRADEMARK OFFICE
CERTIFICATE OF CORRECTION

| | | |
|---|---|---|
| PATENT NO. | : 7,148,325 B2 | |
| APPLICATION NO. | : 09/968355 | |
| DATED | : December 12, 2006 | |
| INVENTOR(S) | : Michael Sakalian and Eric Hunter | |

It is certified that error appears in the above-identified patent and that said Letters Patent is hereby corrected as shown below:

Column 26,
Line 43, "domain of GALA might" should read --domain of GAL4 might--.

Column 27,
Line 1, "maybe used to screen" should read --may be used to screen--.
Line 4, "mMESSAGE MMACHINE kit" should read --mMESSAGE mMACHINE kit--.
Line 10, "reactions maybe performed" should read --reactions may be performed--.

Column 28,
Line 57, "library. hi previous" should read --library. In previous--.

Column 29,
Line 27, "initiallyconjugatedpeptide" should read --initially conjugated peptide--.

Column 30,
Line 8, "form pGAG78," should read --from pGAG78,--.
Line 21, "fragment of pSHRMI5.R55W" should read --fragment of pSHRM15.R55W--.
Lines 25-26, "1045-53the arginine-to-tryptophan" should read
         --1045-53 containing the arginine-to-tryptophan--.
Line 36, "the p112" should read --the p12--.
Line 48, "and subjoining steps." should read --and subcloning steps.--.
Line 59, "To subdlone the" should read --To subclone the--.
Line 63, "each subjoining step," should read --each subcloning step,--.

Column 31,
Line 1, "pET.ANC.R55W," should read --pET.ΔNC.R55W,--.
Line 7, "RP 1179" should read --RP1179--.
Line 17, "strain BL2 1 (DE3)," should read --strain BL21 (DE3),--.

Column 32,
Line 1, "isopropyl-☐-D-" should read --isopropyl-β-D- --.

UNITED STATES PATENT AND TRADEMARK OFFICE
CERTIFICATE OF CORRECTION

PATENT NO. : 7,148,325 B2
APPLICATION NO. : 09/968355
DATED : December 12, 2006
INVENTOR(S) : Michael Sakalian and Eric Hunter It is certified that error appears in the above-identified patent and that said Letters Patent is hereby corrected as shown below:

Column 71,
Line 6, "heteroloaous retroviral" should read --heterologous retroviral--.
Line 8, "heterolopous retroviral" should read --heterologous retroviral--.
Line 25, "heteroloaous retroviral" should read --heterologous retroviral--.
Line 28, "heterolopous retroviral" should read --heterologous retroviral--.

Column 72,
Line 14, "An chimeric" should read --A chimeric--.
Line 25, "heteroloaous retroviral" should read --heterologous retroviral--.

Signed and Sealed this

Twenty-fourth Day of June, 2008

JON W. DUDAS
*Director of the United States Patent and Trademark Office*